(12) United States Patent
Weinschenk et al.

(10) Patent No.: US 8,895,514 B2
(45) Date of Patent: *Nov. 25, 2014

(54) COMPOSITION OF TUMOR-ASSOCIATED PEPTIDES AND RELATED ANTI-CANCER VACCINE FOR THE TREATMENT OF GLIOBLASTOMA (GBM) AND OTHER CANCERS

(71) Applicant: Immatics Biotechnologies GmbH, Tuebingen (DE)

(72) Inventors: Toni Weinschenk, Aichwald (DE); Oliver Schoor, Tuebingen (DE); Claudia Trautwein, Wuelfrath (DE); Norbert Hilf, Kirchentellinsfurt (DE); Steffan Walter, Reutlingen (DE); Harpreet Singh, Tuebingen (DE)

(73) Assignee: Immatics Biotechnologies GmbH, Tuebingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/841,013

(22) Filed: Mar. 15, 2013

(65) Prior Publication Data

US 2013/0309193 A1 Nov. 21, 2013

Related U.S. Application Data

(60) Division of application No. 13/588,206, filed on Aug. 17, 2012, now Pat. No. 8,653,035, which is a division of application No. 12/571,602, filed on Oct. 1, 2009, now Pat. No. 8,318,677, which is a continuation of application No. PCT/EP2009/006979, filed on Sep. 28, 2009.

(60) Provisional application No. 61/105,970, filed on Oct. 16, 2008.

(30) Foreign Application Priority Data

Oct. 1, 2008 (EP) .................................... 08017305

(51) Int. Cl.
*A61K 38/00* (2006.01)
*A61K 39/00* (2006.01)
*C07K 7/06* (2006.01)
*C07K 7/08* (2006.01)

(52) U.S. Cl.
CPC .............. *A61K 39/0011* (2013.01); *C07K 7/06* (2013.01); *C07K 7/08* (2013.01); *A61K 2039/5154* (2013.01); *A61K 2039/53* (2013.01)

USPC .......... 514/19.2; 530/324; 530/325; 530/326; 530/327; 530/328

(58) Field of Classification Search
None
See application file for complete search history.

(56) References Cited

U.S. PATENT DOCUMENTS

2010/0158929 A1 6/2010 Lewandrowski et al.

FOREIGN PATENT DOCUMENTS

| EP | 1760089 A1 | 3/2007 |
|----|-----------|--------|
| WO | 02074237 A2 | 9/2002 |
| WO | 2005116051 A2 | 12/2005 |
| WO | 07/047796 A2 | 4/2007 |
| WO | 2008109757 A2 | 9/2008 |

OTHER PUBLICATIONS

Murphy et al.; Janeway's Immunobiology; 7th Ed.; Chapter 3; pp. 123-140 (Garland Sci., Nov. 27, 2007).
Murphy et al.; Janeway's immunobiology, 7th Ed.; Chapter 5, pp. 181-214 (Garland Sci., Nov. 27, 2007).
Lund et al.; Web-based Tools for Vaccine Design, pp. 45-51 in HIV Molecular Immunology 2002 (Published by Theoretical Biology and Biophysics Group, 2002), available at http://www.cbs.dtu.dk/researchgroups/immunology/webreview.html (last accessed Feb. 14, 2012).
Extended EP Search Report for EP 08 01 7305 dated Jun. 24, 2009 (13 pages).
Partial EP Search Report for EP 0801 7305 dated Feb. 18, 2009 (5 pages).
Prakash, et al.; "Gastrintestinal stromal tumors in children and young adults: a clinicopathologic, molecular, and genomic study of 15 cases and review of the literature"; Journal of Pediatric Hematology/Oncology: Official Journal of the American Society of Pediatric Hematology/Oncology; Apr. 2005; vol. 27; No. 4; pp. 179-187.
Pazona et al.; "Neuroligin 4 isoform Y: A novel marker for prostate cancer"; Journal of Urology; vol. 177; No. 4; Supp. S; Apr. 2007; pp. 538-539; AUA Annual Meeting 2007.
International Preliminary Report on Patentability of PCT/EP2009/006979 dated Apr. 14, 2011.

*Primary Examiner* — Sheela J Huff
(74) *Attorney, Agent, or Firm* — Miles & Stockbridge, PC

(57) ABSTRACT

The present invention relates to immunotherapeutic peptides and their use in immunotherapy, in particular the immunotherapy of cancer. The present invention discloses tumor-associated T-helper cell peptide epitopes, alone or in combination with other tumor-associated peptides that serve as active pharmaceutical ingredients of vaccine compositions which stimulate anti-tumor immune responses. In particular, the composition of the peptides of the present invention can be used in vaccine compositions for eliciting anti-tumor immune responses against gliomas.

20 Claims, 7 Drawing Sheets

COMPOSITION OF TUMOR-ASSOCIATED PEPTIDES AND RELATED ANTI-CANCER VACCINE FOR THE TREATMENT OF GLIOBLASTOMA (GBM) AND OTHER CANCERS

CROSS REFERENCE TO RELATED APPLICATIONS

This application is a Divisional of U.S. application Ser. No. 13/588,206, filed Aug. 17, 2012, which is a Divisional of U.S. application Ser. No. 12/571,602, filed Oct. 1, 2009, now U.S. Pat. No. 8,318,677, which issued Nov. 27, 2012, which claims priority to PCT/EP2009/006979, filed Sep. 28, 2009, which claims priority to European Application No. 08017305.7, filed Oct. 1, 2008, and U.S. Provisional Application No. 61/105,970, filed on Oct. 16, 2008, each of which is hereby incorporated by reference in their entireties.

BACKGROUND

1. Field of the Invention

The present invention relates to immunotherapeutic peptides and their use in immunotherapy, in particular the immunotherapy of cancer. The present invention discloses tumor-associated T-helper cell peptide epitopes, alone or in combination with other tumor-associated peptides that serve as active pharmaceutical ingredients of vaccine compositions which stimulate anti-tumor immune responses. In particular, the composition of the peptides of the present invention can be used in vaccine compositions for eliciting anti-tumor immune responses against gliomas.

For the purposes of the present invention, all references as cited herein are incorporated by reference in their entireties.

2. Description of Related Art

Gliomas are brain tumors originating from glial cells in the nervous system. Glial cells, commonly called neuroglia or simply glia, are non-neuronal cells that provide support and nutrition, maintain homeostasis, form myelin, and participate in signal transmission in the nervous system. The two most important subgroups of gliomas are astrocytomas and oligodendrogliomas, named according to the normal glial cell type from which they originate (astrocytes or oligodendrocytes, respectively). Belonging to the subgroup of astrocytomas, glioblastoma multiforme (referred to as glioblastoma hereinafter) is the most common malignant brain tumor in adults and accounts for approx. 40% of all malignant brain tumors and approx. 50% of gliomas. It aggressively invades the central nervous system and is ranked at the highest malignancy level (grade IV) among all gliomas. Although there has been steady progress in their treatment due to improvements in neuroimaging, microsurgery, diverse treatment options, such as temozolomide or radiation, glioblastomas remain incurable. The lethal rate of this brain tumor is very high: the average life expectancy is 9 to 12 months after first diagnosis. The 5-year survival rate during the observation period from 1986 to 1990 was 8.0%. To date, the five-year survival rate following aggressive therapy including gross tumor resection is still less than 10%. Accordingly, there is a strong medical need for an alternative and effective therapeutic method.

Tumor cells of glioblastomas are the most undifferentiated ones among brain tumors, so the tumor cells have high potential of migration and proliferation and are highly invasive, leading to very poor prognosis. Glioblastomas lead to death due to rapid, aggressive, and infiltrative growth in the brain. The infiltrative growth pattern is responsible for the unresectable nature of these tumors. Glioblastomas are also relatively resistant to radiation and chemotherapy, and, therefore, post-treatment recurrence rates are high. In addition, the immune response to the neoplastic cells is rather ineffective in completely eradicating all neoplastic cells following resection and radiation therapy.

Glioblastoma is classified into primary glioblastoma (de novo) and secondary glioblastoma, depending on differences in the gene mechanism during malignant transformation of undifferentiated astrocytes or glial precursor cells. Secondary glioblastoma occurs in a younger population of up to 45 years of age. During 4 to 5 years, on average, secondary glioblastoma develops from lower-grade astrocytoma through undifferentiated astrocytoma. In contrast, primary glioblastoma predominantly occurs in an older population with a mean age of 55 years. Generally, primary glioblastoma occurs as fulminant glioblastoma characterized by tumor progression within 3 months from the state with no clinical or pathological abnormalities.

Glioblastoma migrates along myelinated nerves and spreads widely in the central nervous system. In most cases surgical treatment shows only limited sustainable therapeutic effect.

Malignant glioma cells evade detection by the host's immune system by producing immunosuppressive agents that impair T cell proliferation and production of the immune-stimulating cytokine IL-2.

Intracranial neoplasms can arise from any of the structures or cell types present in the CNS, including the brain, meninges, pituitary gland, skull, and even residual embryonic tissue. The overall annual incidence of primary brain tumors in the United States is 14 cases per 100,000. The most common primary brain tumors are meningiomas, representing 27% of all primary brain tumors, and glioblastomas, representing 23% of all primary brain tumors (whereas glioblastomas account for 40% of malignant brain tumor in adults). Many of these tumors are aggressive and of high grade. Primary brain tumors are the most common solid tumors in children and the second most frequent cause of cancer death after leukemia in children.

The search for effective treatment of glioblastomas in patients is still ongoing today. Immunotherapy or treatment via recruitment of the immune system, to fight these neoplastic cells has been investigated. First encouraging results were obtained by Northwest Therapeutics using "DCVax Brain" for the treatment of glioblastoma in immuno-therapeutic studies in humans, in which antigen-specific CTL responses could be induced leading to prolonged median survival times compared to that obtained applying standard treatment accompanied by minimal toxicity (Heimberger et al., 2006).

Colorectal Carcinoma

According to the American Cancer Society, colorectal cancer (CRC) is the third most common cancer in the US, afflicting more than 175,000 new patients each year. In the US, Japan, France, Germany, Italy Spain and the UK, it affects more than 480,000 patients. It is one of the most common causes of cancer mortality in developed countries. Research suggests that the onset of colorectal cancer is the result of interactions between inherited and environmental factors. In most cases adenomatous polyps appear to be precursors to colorectal tumors; however the transition may take many years. The primary risk factor for colorectal cancer is age, with 90% of cases diagnosed over the age of 50 years. Other risk factors for colorectal cancer according to the American Cancer Society include alcohol consumption, a diet high in fat and/or red meat and an inadequate intake of fruits and vegetables. Incidence continues to rise, especially in areas such as Japan, where the adoption of westernised diets with excess fat and meat intake and a decrease in fiber intake may be to blame. However, incidence rates are rising not as fast as previously which may be due to increasing screening and polyp removal, thus preventing progression of polyps to cancer.

As in most solid tumors, first line treatment is surgery, however, its benefits remain confined to early-stage patients, yet a significant proportion of patients are diagnosed in advanced stages of the disease. For advanced colorectal cancer chemotherapy regimens based on fluorouracil-based regimens are standard of care. The majority of these regimens are the so-called FOLFOX (infusional 5-FU/leucovorin plus oxaliplatin) and FOLFIRI (irinotecan, leucovorin, bolus and continuous-infusion 5-FU) protocols.

The introduction of third-generation cytotoxics such as irinotecan and oxaliplatin has raised the hope of significantly improving efficacy, but prognosis is still relatively poor, and the survival rate generally remains at approximately 20 months in metastatic disease and, as a result, the unmet needs in the disease remain high.

Recently, a novel generation of drugs, molecular-targeted agents, such as Avastin (bevacizumab) and Erbitux (cetuximab), became available, and about 40 compounds are in late-stage clinical development for different stages of colorectal cancer. Combinations of several of these compounds increase the number of potential treatment options to be expected for the future. The vast majority of substances are in phase 2, with EGFR addressed by these compounds more often than by any other drug in development for colorectal cancer, which is due to the fact that in ~80% of patients with colorectal cancer EGFR expression is upregulated.

Clinical trials with stage II patients combining chemotherapy with the recently approved monoclonal antibodies (mAbs) (cetuximab+irinotecan or FOLFOX4; bevacizumab as a single-agent or together with FOLFOX4) are currently conducted. Three to four year observation periods are expected for statistically significant results from these trials.

Monoclonal antibodies (mAbs) presently used in oncology in general have an excellent chance of not interfering with active immunotherapy. In fact, there is preclinical evidence suggesting that depletion of VEGF (by bevacizumab) contributes positively to DC-mediated activation of T-cells.

Prostate Carcinoma and Other Tumors

With an estimated 27,050 deaths in 2007, prostate cancer is a leading cause of cancer death in men. Although death rates have been declining among white and African American men since the early 1990s, rates in African American men remain more than twice as high as those in white men. Prostate cancer is the most frequently diagnosed cancer in men. For reasons that remain unclear, incidence rates are significantly higher in African American men than in white men. Incidence rates of prostate cancer have changed substantially over the last 20 years: rapidly increasing from 1988-1992, declining sharply from 1992-1995, and increasing modestly since 1995. These trends in large part reflect increased prostate cancer screening with the prostate-specific antigen (PSA) blood test. Moderate incidence increases in the last decade are most likely attributable to widespread PSA screening among men younger than 65. Prostate cancer incidence rates have leveled off in men aged 65 years and older. Rates peaked in white men in 1992 (237.6 per 100,000 men) and in African American men in 1993 (342.8 per 100,000 men).

Treatment for prostate cancer may involve watchful waiting, surgery, radiation therapy, High Intensity Focused Ultrasound (HIFU), chemotherapy, cryosurgery, hormonal therapy, or some combination. Which option is best depends on the stage of the disease, the Gleason score, and the PSA level. Other important factors are the man's age, his general health, and his feelings about potential treatments and their possible side effects. Because all treatments can have significant side effects, such as erectile dysfunction and urinary incontinence, treatment discussions often focus on balancing the goals of therapy with the risks of lifestyle alterations.

If the cancer has spread beyond the prostate, treatment options significantly change, so most doctors who treat prostate cancer use a variety of nomograms to predict the probability of spread. Treatment by watchful waiting, HIFU, radiation therapy, cryosurgery, and surgery are generally offered to men whose cancer remains within the prostate. Hormonal therapy and chemotherapy are often reserved for disease which has spread beyond the prostate. However, there are exceptions: radiation therapy may be used for some advanced tumors, and hormonal therapy is used for some early stage tumors. Cryotherapy, hormonal therapy, and chemotherapy may also be offered if initial treatment fails and the cancer progresses.

In a significant number of patients with prostate carcinoma who undergo radical prostatectomy because of clinically suspected organ-limited growth, a definitive histological workup of the surgical preparation shows a locally extensive tumor extending beyond the borders of the organ. These patients have a high risk for early local recurrence, usually detectable as an increasing PSA level in terms of a biochemical relapse. Therapeutic options in this situation include external radiotherapy and hormone ablation; however, the value of these therapeutic approaches, especially with respect to prolonging the patient's long-term survival, must not be regarded as proven. In addition, possible treatment-associated complications such as the development of urethral strictures (radiotherapy), loss of libido and impotence, the risk of a reduction in skeletal calcium salts in terms of osteoporosis, and a markedly increased risk of pathologic bone fractures (hormone ablation) must be considered.

More than 90% of all prostate cancers are discovered in the local and regional stages; the 5-year relative survival rate for patients whose tumors are diagnosed at these stages approaches 100%. Over the past 25 years, the 5-year survival rate for all stages combined has increased from 69% to nearly 90%. According to the most recent data, relative 10-year survival is 93% and 15-year survival is 77%. The dramatic improvements in survival, particularly at 5 years, are partly attributable to earlier diagnosis and improvements in treatment. Nevertheless, the survival rate drops significantly after the spreading to other tissues and organs.

Lung Cancer

Estimated 210,000 new cases are expected in 2007 in the USA, accounting for about 15% of cancer diagnoses. The incidence rate is declining significantly in men, from a high of 102 cases per 100,000 in 1984 to 78.5 in 2003. In women, the rate is approaching a plateau after a long period of increase. Lung cancer is classified clinically as small cell (13%) or non-small cell (87%) for the purposes of treatment.

Lung cancer accounts for the most cancer-related deaths in both men and women. An estimated 160,390 deaths, accounting for about 29% of all cancer deaths, are expected to occur in 2007. Since 1987, more women have died each year from lung cancer than from breast cancer. Death rates have continued to decline significantly in men from 1991-2003 by about 1.9% per year. Female lung cancer death rates are approaching a plateau after continuously increasing for several decades. These trends in lung cancer mortality reflect the decrease in smoking rates over the past 30 years.

Treatment options are determined by the type (small cell or non-small cell) and stage of cancer and include surgery, radiation therapy, chemotherapy, and targeted biological therapies such as bevacizumab (Avastin®) and erlotinib (Tarceva®). For localized cancers, surgery is usually the treatment of choice. Recent studies indicate that survival with early-stage, non-small cell lung cancer is improved by chemotherapy following surgery. Because the disease has usually spread by the time it is discovered, radiation therapy and chemotherapy are often used, sometimes in combination with surgery. Chemotherapy alone or combined with radiation is the usual treatment of choice for small cell lung cancer; on this regimen, a large percentage of patients experience remission, which is long lasting in some cases.

The 1-year relative survival for lung cancer has slightly increased from 37% in 1975-1979 to 42% in 2002, largely due to improvements in surgical techniques and combined therapies. However, the 5-year survival rate for all stages combined is only 16%. The survival rate is 49% for cases detected when the disease is still localized; however, only 16% of lung cancers are diagnosed at this early stage.

groups of the adjacent amino acids. The length of the oligopeptide is not critical to the invention, as long as the correct epitope or epitopes are maintained therein. The oligopeptides are typically less than about 30 amino acid residues in length, and greater than about 14 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus an "immunogen" within the present invention), if it is capable of inducing an immune response. In the case of the present invention, immunogenicity is more specifically defined as the ability to induce a T-cell response. Thus, an "immunogen" would be a

TABLE 1

Estimated new cancer cases and deaths by sex for the US in 2007 (American Cancer Society. Cancer Facts & Figures 2007. Atlanta: American Cancer Society; 2007.)

| Sites | Estimated New Cases | | | Estimated Deaths | | |
|---|---|---|---|---|---|---|
| | Both Sexes | Male | Female | Both Sexes | Male | Female |
| Glioma and Brain | 20,500 | 11,170 | 9,330 | 12,740 | 7,150 | 5,590 |
| Breast | 180,510 | 2,030 | 178,480 | 40,910 | 450 | 40,460 |
| Prostate | 218,890 | 218,890 | | 27,050 | 27,050 | |
| Esophagus | 15,560 | 12,130 | 3,430 | 13,940 | 10,900 | 3,040 |
| Colon | 112,340 | 55,290 | 57,050 | 52,180 | 26,000 | 26,180 |
| Renal | 51,190 | 31,590 | 19,600 | 12,890 | 8,080 | 4,810 |
| Pancreas | 37,170 | 18,830 | 18,340 | 33,370 | 16,840 | 16,530 |
| Squamous cell carcinomas; Keratinocytic neoplasms of the skin | 1,000,000 | n.d. | n.d. | n.d. | n.d. | n.d. |
| Leukemia | 44,240 | 24,800 | 19,440 | 21,790 | 12,320 | 9,470 |
| Lung | 213,380 | 114,760 | 98,620 | 160,390 | 89,510 | 70,880 |
| Non-Hodgkin Lymphoma | 63,190 | 34,210 | 28,990 | 18,660 | 9,600 | 9,060 |
| Ovarian | 22,430 | | 22,430 | 15,280 | | 15,280 |
| Melanoma | 59,940 | 33,910 | 26,030 | 8,110 | 5,220 | 2,890 |

There thus remains a need for new efficacious and safe treatment option for glioblastoma, prostate tumor, breast cancer, esophageal cancer, colorectal cancer, clear cell renal cell carcinoma, lung cancer, CNS, ovarian, melanoma, pancreatic cancer, squamous cell carcinoma, leukemia and medulloblastoma and other tumors which show an overexpression of survivin, enhancing the well-being of the patients without using chemotherapeutic agents or other agents which may lead to severe side effects.

DETAILED DESCRIPTION OF THE INVENTION

As used herein and except as noted otherwise all terms are defined as given below. The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, 13, 14, 15, 16, 17 or 18 amino acids in length.

The term "oligopeptide" is used herein to designate a series of amino acid residues, connected one to the other typically by peptide bonds between the alpha-amino and carbonyl molecule that is capable of inducing an immune response, and in the case of the present invention, a molecule capable of inducing a T-cell response.

A T cell "epitope" requires a short peptide that is bound to a class I or II MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length. T cell epitopes that bind to MHC class II molecules are typically 12-30 amino acids in length. In the case of peptides that bind to MHC class II molecules, the same peptide and the corresponding T cell epitope may share a common core segment, but differ in the overall length due to flanking sequences of differing lengths upstream of the amino-terminus of the core sequence and downstream of its carboxy-terminus, respectively. MHC class II receptors have a more open conformation, peptides bound to MHC class II receptors are correspondingly not completely buried in the structure of the MHC class II molecule peptide-binding cleft as they are in the MHC class I molecule peptide-binding cleft. Surprisingly this is not the case for the peptide according to SEQ ID NO:1, as small variations in the length of the peptide lead to an extreme decrease of activity (see below).

In humans there, are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-A*11 are examples of different MHC class I alleles that can be expressed from these loci.

There are three different loci in the human genome for MHC class II genes: HLA-DR, HLA-DQ, and HLA-DP. MHC class II receptors are heterodimers consisting of an alpha and a beta chain, both anchoring in the cell membrane via a transmembrane region. HLA-DRB1*04, and HLA-DRB1*07 are two examples of different MHC class II beta alleles that are known to be encoded in these loci. Class II alleles are very polymorphic, e.g. several hundred different HLA-DRB1 alleles have been described. For HLA-A*02 and most frequent HLA-DR serotypes, expression frequencies in different populations are shown in Table 2.

TABLE 2

Expression frequencies F of HLA*A02 and the most frequent HLA-DR serotypes. Frequencies are deduced from haplotype frequencies Gf within the American population adapted from Mori et al. (Mori et al., 1997) employing the Hardy-Weinberg formula $F = 1 - (1 - Gf)^2$. Combinations of A*02 with certain HLA-DR alleles might be enriched or less frequent than expected from their single frequencies due to linkage disequilibrium. For details refer to Chanock et al. (Chanock et al., 2004).

| HLA Allele | Expression frequencies of HLA*02 and HLA-DR serotypes within North American subpopulations | | | |
|---|---|---|---|---|
| | Caucasian American | African American | Asian American | Latin American |
| A*02 | 49.1% | 34.1% | 43.2% | 48.3% |
| DR1 | 19.4% | 13.2% | 6.8% | 15.3% |
| DR2 | 28.2% | 29.8% | 33.8% | 21.2% |
| DR3 | 20.6% | 24.8% | 9.2% | 15.2% |
| DR4 | 30.7% | 11.1% | 28.6% | 36.8% |
| DR5 | 23.3% | 31.1% | 30.0% | 20.0% |
| DR6 | 26.7% | 33.7% | 25.1% | 31.1% |
| DR7 | 24.8% | 19.2% | 13.4% | 20.2% |
| DR8 | 5.7% | 12.1% | 12.7% | 18.6% |
| DR9 | 2.1% | 5.8% | 18.6% | 2.1% |

Therefore, for therapeutic and diagnostic purposes a peptide that binds with appropriate affinity to several different HLA class II receptors is highly desirable. A peptide binding to several different HLA class II molecules is called a promiscuous binder.

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence. The term "coding region" refers to that portion of a gene which either naturally or normally codes for the expression product of that gene in its natural genomic environment, i.e., the region coding in vivo for the native expression product of the gene.

The coding region can be from a normal, mutated or altered gene, or can even be from a DNA sequence, or gene, wholly synthesized in the laboratory using methods well known to those of skill in the art of DNA synthesis.

The term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

The term "expression product" means the polypeptide or protein that is the natural translation product of the gene and any nucleic acid sequence coding equivalents resulting from genetic code degeneracy and thus coding for the same amino acid(s).

The term "fragment," when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal nontranslated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'OH end at which a DNA polymerase starts synthesis of a deoxyribonucleotide chain.

The term "promoter" means a region of DNA involved in binding of RNA polymerase to initiate transcription.

The term "open reading frame (ORF)" means a series of triplets coding for amino acids without any termination codons and is a sequence (potentially) translatable into protein.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, the claimed polypeptide which has a purity of preferably 99.999%, or at least 99.99% or 99.9%; and even desirably 99% by weight or greater is expressly contemplated.

The nucleic acids and polypeptide expression products disclosed according to the present invention, as well as expression vectors containing such nucleic acids and/or such polypeptides, may be in "enriched form." As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form.

The term "active fragment" means a fragment that generates an immune response (i.e., has immunogenic activity) when administered, alone or optionally with a suitable adjuvant, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. This means that any such fragment will necessarily contain as part of its amino acid sequence a segment, fragment or portion, that is substantially identical, if not exactly identical, to a sequence of SEQ ID NO:1 to 20, which correspond to the naturally occurring, or "parent" proteins of the SEQ ID NO:1 to 20. When used in relation to polynucleotides, such terms refer to the products produced by treatment of said polynucleotides with any of the common endonucleases.

In accordance with the present invention, the term "percent identity" or "percent identical," when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

Percent Identity=100[$I-(C/R)$]

wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference;

and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated Percent Identity is less than the specified Percent Identity.

The original peptides disclosed herein can be modified by the substitution of one or more residues at different, possibly selective, sites within the peptide chain, if not otherwise stated. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, amino acids possessing non-standard R groups (i.e., R groups other than those found in the common 20 amino acids of natural proteins) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would simultaneously be substituted.

The term "T-cell response" means the specific proliferation and activation of effector functions induced by a peptide in vitro or in vivo. For MHC class I restricted CTLs, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation. For MHC class II-restricted T helper cells, effector functions may be peptide induced secretion of cytokines, preferably, IFN-gamma, TNF-alpha, IL-4, IL5, IL-10, or IL-2, or peptide-induced degranulation. Possible effector functions for CTLs and T helper cells are not limited to this list.

Immunotherapeutic Approaches for Treatment

Stimulation of an immune response is dependent upon the presence of antigens recognised as foreign by the host immune system. The discovery of the existence of tumor associated antigens has now raised the possibility of using a host's immune system to intervene in tumor growth. Various mechanisms of harnessing both the humoral and cellular arms of the immune system are currently explored for cancer immunotherapy.

Specific elements of the cellular immune response are capable of specifically recognising and destroying tumor cells. The isolation of cytotoxic T-cells (CTL) from tumor-infiltrating cell populations or from peripheral blood suggests that such cells play an important role in natural immune defences against cancer. CD8-positive T-cells in particular, which recognise class I molecules of the major histocompatibility complex (MHC)-bearing peptides of usually 8 to 10 residues derived from proteins or defect ribosomal products (DRIPS) (Schubert U, Antón L C, Gibbs J, Norbury C C, Yewdell J W, Bennink J R.; Rapid degradation of a large fraction of newly synthesized proteins by proteasomes; Nature 2000; 404(6779):770-774) located in the cytosols, play an important role in this response. The MHC-molecules of the human are also designated as human leukocyte-antigens (HLA).

There are two classes of MHC-molecules: MHC class I molecules that can be found on most cells having a nucleus which present peptides that result from proteolytic cleavage of mainly endogenous, cytosolic or nuclear proteins, DRIPS, and larger peptides. However, peptides derived from endosomal compartments or exogenous sources are also frequently found on MHC class I molecules. This non-classical way of class I presentation is referred to as cross-presentation in literature. MHC class II molecules can be found predominantly on professional antigen presenting cells (APCs), and present predominantly peptides of exogenous proteins that are taken up by APCs during the course of endocytosis, and are subsequently processed. As for class I, alternative ways of antigen processing are described that allow peptides from endogenous sources to be presented by MHC class II molecules (e.g. autophagocytosis). Complexes of peptide and MHC class I molecule are recognised by CD8-positive cytotoxic T-lymphocytes bearing the appropriate TCR, complexes of peptide and MHC class II molecule are recognised by CD4-positive helper T-cells bearing the appropriate TCR.

CD4-positive helper T-cells play an important role in orchestrating the effector functions of anti-tumor T-cell responses and for this reason the identification of CD4-positive T-cell epitopes derived from tumor associated antigens (TAA) may be of great importance for the development of pharmaceutical products for triggering anti-tumor immune responses (Gnjatic, S., D. Atanackovic, E. Jäger, M. Matsuo, A. Selvakumar, N. K. Altorki, R. G. Maki, B. Dupont, G. Ritter, Y. T. Chen, A. Knuth, and L. J. Old. Survey of naturally occurring CD4+ T-cell responses against NY-ESO-1 in cancer patients: Correlation with antibody responses. Proc. Natl. Acad. Sci. U.S.A. 2003, 100 (15): 8862-7) CD4+ T cells can lead to locally increased levels of IFN-gamma (IFN-γ).

It was shown in mammalian animal models, e.g., mice, that even in the absence of CTL effector cells (i.e., CD8-positive T lymphocytes), CD4-positive T-cells are sufficient for inhibiting manifestation of tumors via inhibition of angiogenesis by secretion of interferon-gamma (IFNγ) (Qin, Z. and T. Blankenstein. CD4+ T-cell-mediated tumor rejection involves inhibition of angiogenesis that is dependent on IFN gamma receptor expression by nonhematopoietic cells. Immunity. 2000, 12:677-686). Additionally, it was shown that CD4-positive T-cells recognizing peptides from tumor-associated antigens presented by HLA class II molecules can counteract tumor progression via the induction of an antibody (Ab) responses (Kennedy, R. C., M. H. Shearer, A. M. Watts, and R. K. Bright. CD4+ T lymphocytes play a critical role in antibody production and tumor immunity against simian virus 40 large tumor antigen. Cancer Res. 2003, 63:1040-1045). In contrast to tumor-associated peptides binding to HLA class I molecules, only a small number of class II ligands of TAA have been described so far (www.cancerimmunity.org, www.syfpeithi.de).

Since the constitutive expression of HLA class II molecules is usually limited to cells of the immune system the possibility of isolating class II peptides directly from primary tumors was not considered possible. However, the inventors were recently successful in identifying a number of MHC class II epitopes directly from tumors (EP 1642905, EP 1760088; Dengjel J, Nastke M D, Gouttefangeas C, Gitsioudis G, Schoor O, Altenberend F, Müller M, Krämer B, Missiou A, Sauter M, Hennenlotter J, Wernet D, Stenzl A, Rammensee H G, Klingel K, Stevanović S.; Unexpected abundance of HLA class II presented peptides in primary renal cell carcinomas; Clin Cancer Res. 2006; 12:4163-4170).

In the absence of inflammation, expression of MHC class II molecules is mainly restricted to cells of the immune system, especially APCs, e.g., monocytes, monocyte-derived cells, macrophages, dendritic cells. In tumor patients, cells of the tumor have surprisingly been found to express MHC class II molecules (Dengjel J, Nastke M D, Gouttefangeas C, Gitsioudis G, Schoor O, Altenberend F, Müller M, Krämer B, Missiou A, Sauter M, Hennenlotter J, Wernet D, Stenzl A, Rammensee H G, Klingel K, Stevanović S.; Unexpected abundance of HLA class II presented peptides in primary renal cell carcinomas; Clin Cancer Res. 2006; 12:4163-4170)

For a peptide to trigger (elicit) a cellular immune response, it must bind to an MHC-molecule. This process is dependent on the allele of the MHC-molecule and specific polymorphisms of the amino acid sequence of the peptide. MHC-class-1-binding peptides are usually 8-10 amino acid residues in length and usually contain two conserved residues ("anchor") in their sequence that interacts with the corresponding binding groove of the MHC-molecule. In this way each MHC allele has a "binding motif" determining which peptides can bind specifically to the binding groove (Rammensee H G, Bachmann J, Stevanović S. MHC ligands and peptide motifs, Landes Bioscience, USA, 1997).

In MHC dependent immune reaction, peptides not only have to be able to bind to certain MHC molecules expressed by tumor cells, they also have to be recognised by T-cells bearing specific T-cell receptors (TCR).

The antigens that are recognised by the tumor specific T-lymphocytes, that is, their epitopes, can be molecules derived from all protein classes, such as enzymes, receptors, transcription factors, etc. Furthermore, tumor-associated antigens, for example, can also be present in tumor cells only, for example as products of mutated genes. Another important class of tumor-associated antigens are tissue-specific antigens, such as CT ("cancer testis")-antigens that are expressed in different kinds of tumors and in healthy tissue of the testis.

Various tumor-associated antigens have been identified. Further, much research effort is expended to identify additional tumor associated antigens. Some groups of tumor-associated antigens, also referred to in the art as tumor-specific antigens, are tissue specific. Examples include, but are not limited to, tyrosinase for melanoma, PSA and PSMA for prostate cancer and chromosomal cross-overs (translocations) such as bcr/abl in lymphoma. However, many tumor-associated antigens identified occur in multiple tumor types, and some, such as oncogenic proteins and/or tumor suppressor genes (tumor suppressor genes are, for example reviewed for renal cancer in Linehan W M, Walther M M, Zbar B. The genetic basis of cancer of the kidney. J. Urol. 2003 December; 170 (6Pt1):2163-72) which actually cause the transformation event, occur in nearly all tumor types. For example, normal cellular proteins that control cell growth and differentiation, such as p53 (which is an example for a tumor suppressor gene), ras, c-met, myc, pRB, VHL, and HER-2/neu, can accumulate mutations resulting in upregulation of expression of these gene products thereby making them oncogenic (McCartey et al. Cancer Research, 1998, 15:58 2601-5; Disis et al. Ciba Found. Symp. 1994, 187:198-211). These mutant proteins can also be a target of a tumor-specific immune response in multiple types of cancer.

Immunotherapy in cancer patients aims at activating cells of the immune system specifically, especially the so-called cytotoxic T-cells (CTL, also known as "killer cells", also known as CD8-positive T-cells), against tumor cells but not against healthy tissue. Tumor cells differ from healthy cells by the expression of tumor-associated proteins. HLA molecules on the cell surface present the cellular content to the outside, thus enabling a cytotoxic T cell to differentiate between a healthy and a tumor cell. This is realized by breaking down all proteins inside the cell into short peptides, which are then attached to HLA molecules and presented on the cell surface (Rammensee et al., 1993). Peptides that are presented on tumor cells, but not or to a far lesser extent on healthy cells of the body, are called tumor-associated peptides (TUMAPs).

For proteins to be recognised by cytotoxic T-lymphocytes as tumor-specific or -associated antigens, and to be used in a therapy, particular prerequisites must be fulfilled. The antigen should be expressed mainly by tumor cells and not by normal healthy tissues or in comparably small amounts. It is furthermore desirable, that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to a function e.g. in cell cycle control or apoptosis. Additionally, downstream targets of the proteins directly causative for a transformation may be upregulated and thus be indirectly tumor-associated. Such indirectly tumor-associated antigens may also be targets of a vaccination approach. Essential is in both cases the presence of epitopes in the amino acid sequence of the antigen, since such peptide ("immunogenic peptide") that is derived from a tumor associated antigen should lead to an in vitro or in vivo T-cell-response.

Basically, any peptide able to bind a MHC molecule may function as a T-cell epitope. A prerequisite for the induction of an in vitro or in vivo T-cell-response is the presence of a T-cell with a corresponding TCR and the absence of tolerance for this particular epitope. T-helper cells play an important role in orchestrating the effector function of CTLs in anti-tumor immunity. T-helper cell epitopes that trigger a T-helper cell response of the TH1 type support effector functions of CD8-positive killer T-cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions which stimulate anti-tumor immune responses.

Since both types of response, CD8 and CD4 dependent, contribute jointly and synergistically to the anti-tumor effect, the identification and characterization of tumor-associated antigens recognised by either CD8+ CTLs (MHC class I molecule) or by CD4-positive CTLs (MHC class II molecule) is important in the development of tumor vaccines. It is therefore an object of the present invention, to provide compositions of peptides that contain peptides binding to MHC complexes of either class.

First clinical trials using tumor-associated peptides have started in the mid-1990s by Boon and colleagues mainly for the indication melanoma. Clinical responses in the best trials have ranged from 10% to 30%. Severe side effects or severe autoimmunity have not been reported in any clinical trial using peptide-based vaccine monotherapy. Mild forms of vitiligo have been reported for some patients who had been treated with melanoma-associated peptides.

However, priming of one kind of CTL is usually insufficient to eliminate all tumor cells. Tumors are very mutagenic and thus able to respond rapidly to CTL attacks by changing their protein pattern to evade recognition by CTLs. To counter-attack the tumor evasion mechanisms a variety of specific peptides is used for vaccination. In this way a broad simultaneous attack can be mounted against the tumor by several CTL clones simultaneously. This may decrease the chances of the tumor to evade the immune response. This hypothesis has been recently confirmed in a clinical study treating late-stage melanoma patients. With only few exceptions, patients that had at least three distinct T-cell responses, showed objective clinical responses or stable disease (Banchereau et al., 2001) as well as increased survival (personal communication with J. Banchereau), while the vast majority of patients with less than three T-cell responses were diagnosed with progressive disease.

A study of the applicants showed a similar effect when patients suffering from renal cell carcinoma were treated with a vaccine composed of 13 different peptides (H. Singh-Jasuja, S. Walter, T. Weinschenk, A. Mayer, P. Y. Dietrich, M. Staehler, A. Stenzl, S. Stevanovic, H. Rammensee, J. Frisch; Correlation of T-cell response, clinical activity and regulatory T-cell levels in renal cell carcinoma patients treated with IMA901, a novel multi-peptide vaccine; ASCO Meeting 2007 Poster #3017; M. Staehler, A. Stenzl, P. Y. Dietrich, T. Eisen, A. Haferkamp, J. Beck, A. Mayer, S. Walter, H. Singh, J. Frisch, C. G. Stief; An open label study to evaluate the safety and immunogenicity of the peptide based cancer vaccine IMA901, ASCO meeting 2007; Poster #3017).

SUMMARY OF THE INVENTION

A major task in the development of a tumor vaccine was therefore not only the identification and characterisation of novel tumor associated antigens and immunogenic T-helper epitopes derived thereof, but also the combination of different epitopes to increase the likelihood of a response to more than one epitope for each patient. It was therefore an object of the present invention to provide combinations of amino acid sequences of such peptides that have the ability to bind to a molecule of the human major histocompatibility complex (MHC) class-I (HLA class I) or II (HLA class II). It was a further object of the present invention, to provide an effective anti-cancer vaccine that is based on a combination of the peptides.

In the present invention, the inventors did isolate and characterise peptides binding to HLA class I or II molecules directly from mammalian tumors, i.e. primary samples of mainly glioblastoma patients, but also from primary tissue samples of colorectal cancers, renal cell carcinoma, lung cancers, pancreatic cancers, malignant melanoma, and cancer of the stomach.

The present invention provides peptides that stem from antigens associated with tumorigenesis, and have the ability to bind sufficiently to MHC (HLA) class II molecules for triggering an immune response of human leukocytes, especially lymphocytes, especially T lymphocytes, especially CD4-positive T lymphocytes, especially CD4-positive T lymphocytes mediating TH1-type immune responses.

The present invention also provides peptides that stem from antigens associated with tumorigenesis, and have the ability to bind sufficiently to MHC (HLA) class I molecules for triggering an immune response of human leukocytes, especially lymphocytes, especially T lymphocytes, especially CD8-positive cytotoxic T-lymphocytes as well as combinations of the two that are particularly useful for vaccination of patients that suffer from cancer.

According to the present invention, these and other objects can be solved, for example, by providing a pharmaceutical composition comprising at least two peptides containing an amino acid sequence selected from the group consisting of SEQ ID NO:1 to SEQ ID NO:8, and/or containing a variant amino acid sequence that is at least 80% homologous to that of SEQ ID NO:1 to SEQ ID NO:8, and/or a polynucleotide containing a nucleic acid encoding SEQ ID NO:1 to SEQ ID NO:8 or the variant amino acid sequence, and a pharmaceutically acceptable carrier. Pharmaceutical compositions of the present invention may also further comprise at least one additional peptide containing an amino acid sequence selected from the group consisting of SEQ ID NO:9 to SEQ ID NO:20, or containing a variant amino acid sequence that is at least 80% identical to that of SEQ ID NO:9 to SEQ ID NO:20, or polynucleotide containing a nucleic acid encoding SEQ ID NO:9 to SEQ ID NO:20 or the variant amino acid sequence. The peptides may have an overall length of between 8 and 100, preferably between 8 and 30, and most preferably between 8 and 17 amino acids. The peptides may also have non-peptide bonds.

DETAILED DESCRIPTION OF A PREFERRED EMBODIMENT

Figure 1:
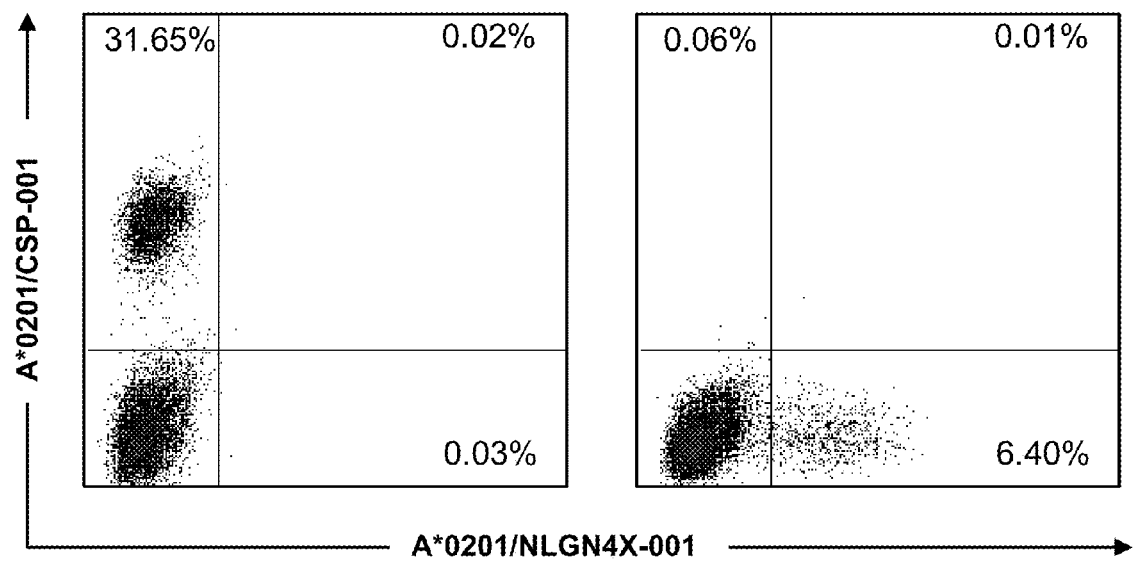
FIGS. 1, 2, 3, 4A, 4B, 5A, and 5B depict various embodiments of the present invention.

As described herein below, the peptides with the exception of MET-005 that form the basis of the present invention have all been identified as presented by MHC class I or II bearing cells. Thus, these particular peptides as well as other peptides containing the sequence (i.e. derived peptides) all elicit a specific T-cell response, although the extent to which such response will be induced might vary from individual peptide to peptide and from individual patient to patient. Differences, for example, could be caused due to mutations in the peptides. The person of skill in the present art is well aware of methods that can be applied to determine the extent to which a response is induced by an individual peptide, in particular with reference to the examples herein and the respective literature.

Preferably the variants of the invention will induce T-cells cross-reacting with the respective peptide of the invention.

The peptides stem from tumor-associated antigens, especially tumor-associated antigens with functions in, e.g., proteolysis, angiogenesis, cell growth, cell cycle regulation, cell division, regulation of transcription, regulation of translation, tissue invasion, etc. Table 3 provides the peptides and the function of the protein the peptides are derived from.

TABLE 3

Peptides of the present invention and function of the parent protein

| SEQ ID NO | Peptide ID | Sequence | Gene Symbol | Function | binds to MHC |
|---|---|---|---|---|---|
| 1 | CSP-001 | TMLARLASA | CSPG4 | transmembrane proteoglycan involved in neovascularization | HLA-A*02 |
| 2 | FABP7-001 | LTFGDVVAV | FABP7 | CNS-specific fatty acid binding protein | HLA-A*02 |
| 3 | NLGN4X-001 | NLDTLMTYV | NLGN4X | Cell-adhesion molecule | HLA-A*02 |
| 4 | TNC-001 | AMTQLLAGV | TNC | extracellular matrix protein | HLA-A*02 |
| 5 | NRCAM-001 | GLWHHQTEV | NRCAM | Neuronal cell-adhesion molecule | HLA-A*02 |
| 6 | IGF2BP3-001 | KIQEILTQV | IGF2BP3 | mRNA binding protein | HLA-A*02 |
| 7 | BCA-002 | ALWAWPSEL | BCAN | proteoglycan | HLA-A*02 |
| 8 | MET-005 | TFSYVDPVITSISPKYG | MET | growth factor receptor | elongated HLA class I TUMAP |

Chondroitin Sulfate Proteoglycan 4 (CSPG4)

CSPG4 (chondroitin sulfate proteoglycan) represents an integral membrane chondroitin sulfate proteoglycan. It is known as an early cell surface melanoma progression marker implicated in stimulating tumor cell proliferation, migration and invasion. CSPG4 is strongly expressed on >90% of human melanoma lesions. Although CSPG4 is not strictly tumor specific, tumor-reactive CD4+ T-cell responses in melanoma patients and healthy individuals recognize CSPG4$_{693-709}$ on HLA-DR11-expressing melanoma cells in the absence of autoimmunity (Erfurt et al., 2007).

Expression of CSPG4 enhances integrin-mediated cell spreading, FAK (focal adhesion kinase) phosphorylation, and activation of ERK1/2 (extracellular signal-regulated kinase) (Yang et al., 2004). Furthermore, there is accumulating evidence from in vitro data that CSPG4 plays an important role in tumor angiogenesis. Thus, CSPG4-positive tumors have been found to have significantly increased neovascularization rates and vascular volumes, and CSPG4 has been shown to sequester angiostatin, which normally inhibits endothelial cell proliferation and angiogenesis. Immature vessels also contain CSPG4-positive pericytes, suggesting a role for this cell population in modulating endothelial cell proliferation by blocking the inhibitory effects of angiostatin during vessel development (Chekenya et al., 2002b).

CSPG4 expression has also been described in some normal tissues besides activated pericytes such as endothelial cells, chondrocytes, smooth muscle cells, certain basal keratinocytes within the epidermis, as well as cells within the hair follicle (Campoli et al., 2004).

During angiogenesis and in response to CNS pathologies, the highly motile CSPG4 cells undergo rapid morphological changes and are recruited to sites where vessel growth and repair are occurring. CSPG4 is over-expressed by both tumor cells and pericytes on the blood vessels of malignant brain tumors (Chekenya and Pilkington, 2002). By implanting cells from an CSPG4-positive human glioma cell line into immunodeficient nude rat brains it was shown that these tumors had a higher microvascular density in comparison to controls implying that CSPG4 expression regulates both the function and the structure of the host-derived tumor vasculature (Brekke et al., 2006). In a xenograft experiment of implantation of GBM biopsy material into nude rats, CSPG4 was identified to be mainly associated with blood vessels on both the pericyte and basement membrane components of the tumor vasculature and the expression was also associated with areas of high cellular proliferation (Chekenya et al., 2002a). Furthermore, CSPG4 expression paralleled progression of the tumor in a glioma implantation model (Wiranowska et al., 2006). Malignant progression is maintained by cross-talk between the tumor and its stroma, where the activated stroma nurtures the proliferative and invasive neoplastic cells, by providing neovasculature, extracellular matrix components, and stimulatory growth factors. In this context, CSPG4 plays a major role in tumor-stroma activation through alterations in cellular adhesion, migration, proliferation, and vascular morphogenesis (Chekenya and Immervoll, 2007).

CSPG4 is differentially expressed in human gliomas with higher expression in high compared to low-grade gliomas (Chekenya et al., 1999). High expression of CSPG4 correlates with multidrug resistance mediated by increased activation of α3β1 integrin/PI3K signaling and their downstream targets, promoting cell survival (Chekenya et al., 2008).

Fatty Acid Binding Protein 7, Brain (IMA-FABP7-001)

Fatty acid-binding proteins (FABPs) are cytosolic 14-15 kDa proteins, which are supposed to be involved in fatty acid (FA) uptake, transport, and targeting. They are thought to increase the solubility of FAs in the cytoplasm when transporting FAs between membrane compartments, and bring FAs to their nuclear targets (Glatz et al., 2002). FABPs may modulate FA concentration and in this way influence various cellular functions such as enzymatic activity, gene expression, cellular growth and differentiation (Glatz and Storch, 2001).

Nervous tissue contains four of the nine known FABP types with a distinct spatio-temporal distribution (Veerkamp and Zimmerman, 2001). FABP7 is highly expressed in radial glial cells throughout the developing central nervous system and gradually declines in the adult (Feng and Heintz, 1995; Shimizu et al., 1997). It is required for neuron-induced glial differentiation and subsequent migration of neurons along the glial processes, but has no effect on cell proliferation and adhesion (Feng et al., 1994; Kurtz et al., 1994). In Schwann cells, FABP7 expression is downstream of the Ras-independent EGFR signaling pathway, and it regulates interactions between Schwann cells and axons in normal peripheral nerves and peripheral nerve tumors (Miller et al., 2003).

FABP7 mRNA is expressed in tissues of neuroepithelial origin as well as in malignant glioma tumors (WHO grade III and IV). The gene was mapped to chromosome band 6q22-23, a region which also contains the proto-oncogene c-myc and frequently undergoes loss of heterozygosity in malignant glioma. Analysis of malignant glioma cell lines showed that FABP7 is often co-expressed with the glial fibrillary acidic protein (GFAP) suggesting that the cell of origin of malignant glioma may be an astrocytic precursor cell that has the potential of expressing both proteins normally or as the result of tumor formation (Godbout et al., 1998). FABP7 protein shows moderate to strong nuclear and cytoplasmic expression in GBM. FABP7-transfected glioma cells display 5-fold greater migration than control cells. Thus, the shorter overall survival associated with FABP7 over-expression especially in GBM may be due to increased migration and invasion of tumor cells into the surrounding brain parenchyma (Liang et al., 2005). Further analysis of FABP7 distribution in astrocytoma tumors indicates elevated levels of FABP7 in infiltrating regions of the tumors proposing an important role for FABP7 in driving the infiltration of malignant cells into adjacent brain tissues (Mita et al., 2007). FABP7 demonstrates variable expression levels and subcellular localization in glial tissues and all grades of astrocytoma. Nevertheless, especially nuclear localization of FABP7 seems to be associated with the infiltrative phenotype of glioma cells and EGFR pathways, as its nuclear translocation is detected after EGFR activation and is associated with poor prognosis in EGFR-positive GBM. Moreover, no nuclear FABP7 immunoreactivity can be observed in grade I astrocytoma (Liang et al., 2006; Kaloshi et al., 2007).

Neuroligin 4, X-Linked (IMA-NLGN4X-001)

Neuroligin 4, X-linked is a member of a cell adhesion protein family that appears to play a role in the maturation and function of neuronal synapses. The members of the neuroligin family have a related structural organization, with an N-terminal signal peptide, the esterase-like domain with two sites of alternative splicing, a small linker region of low sequence identity in front of the transmembrane domain, and a short cytosolic part with a highly conserved C-Terminus. Highest relative neuroligin 4 mRNA levels were found in heart. Lower expression was detected in liver, skeletal muscle and pancreas, whereas in brain, placenta, lung and kidney, neuroligin 4 mRNA was hardly detectable (Bolliger et al., 2001).

Mutations in the X-linked NLGN4 gene are a potential cause of autistic spectrum disorders, and mutations have been reported in several patients with autism, Asperger syndrome, and mental retardation (Jamain et al., 2003; Laumonnier et al., 2004; Lawson-Yuen et al., 2008).

Few associations of NLGN4X with cancer have been described: In gastrointestinal stromal tumors, over-expression of NLGN4X has been found in pediatric and young adult versus older adult cases (Prakash et al., 2005).

Tenascin C (Hexabrachion) (IMA-TNC-001)

The extracellular matrix surrounding tumor cells is different from the extracellular matrix in normal tissues. Tenascin-C (TNC) is an extracellular matrix protein that is highly up-regulated in processes that are closely associated with elevated migratory activity such as embryonic development (Bartsch et al., 1992), wound healing (Mackie et al., 1988) and neoplastic processes (Chiquet-Ehrismann, 1993; Chiquet-Ehrismann and Chiquet, 2003). Furthermore, TNC is over-expressed in tumor vessels that have a high proliferative index which indicates that TNC is involved in neoplastic angiogenesis (Kim et al., 2000). In normal human brain, the expression of TNC is detected only rarely whereas it is expressed at high levels in malignant gliomas (Bourdon et al., 1983). TNC-expression can be induced by hypoxia (Lal et al., 2001), by TGF-beta1, providing a mechanism for the invasion of high-grade gliomas into healthy parenchyma (Hau et al., 2006), or by gastrin, which significantly modulates the migration of human GBM cells (Kucharczak et al., 2001). TNC down-regulates tropomyosin-1 and thus destabilizes actin stress fibers. It additionally causes down-regulation of the Wnt inhibitor Dickkopf1. As reduced tropomyosin-1 expression and increased Wnt signaling are closely linked to transformation and tumorigenesis, TNC specifically modulates these signaling pathways to enhance proliferation of glioma cells (Ruiz et al., 2004).

Perivascular staining of TNC around tumor-supplying blood vessels is observed in GBM tissues, whereas it is less frequent in WHO grade II and III gliomas, indicating that the intensity of TNC staining correlates with the tumor grade and the strongest staining indicates poor prognosis (Herold-Mende et al., 2002). TNC also contributes to the generation of a stem cell niche within the subventricular zone (SVZ), acting to orchestrate growth factor signaling to accelerate neural stem cell development. The predominant effect of TNC on cells in the SVZ is the regulation of developmental progression (Garcion et al., 2004). TNC is the strongest inducer of directed human neural stem cell (NSC) migration. The tumor-produced ECM thus provides a permissive environment for NSC tropism to disseminated tumor cells (Ziu et al., 2006).

Neuronal Cell Adhesion Molecule (IMA-NRCAM-001)

NRCAM (neuronal cell adhesion molecule) is a neuronal transmembrane cell adhesion molecule with multiple immunoglobulin-like C2-type and fibronectin type-III domains. It is involved in the guidance, outgrowth, and fasciculation of neuronal cells (Grumet et al., 1991; Morales et al., 1993; Stoeckli and Landmesser, 1995; Perrin et al., 2001; Sakurai et al., 2001) by forming homophilic, as well as heterophilic interactions with other IgCAMs (Volkmer et al., 1996; Sakurai et al., 1997; Zacharias et al., 1999). The ankyrin-binding NRCAM (Davis and Bennett, 1994) is upregulated in tube forming endothelial cells suggesting a possible role in tube formation and angiogenesis (Aitkenhead et al., 2002).

NRCAM is a target gene of the β-catenin and plakoglobin-LEF/TCF complex that contributes to oncogenesis (Conacci-Sorrell et al., 2002). The NRCAM ectodomain can be shed from the cell surface by metalloprotease-like activities. This shed domain is able to activate various signaling pathways, enhances cell motility, and confers tumorigenesis in mice (Conacci-Sorrell et al., 2005).

NRCAM is upregulated in anaplastic astrocytomas and GBM tumor tissues as compared to normal brain, and increased levels are correlated with the invasive behavior (Sehgal et al., 1998). Antisense RNA against NRCAM decreases the tumorigenic capacity of human GBM cells (Sehgal et al., 1999).

Insulin-like Growth Factor 2 mRNA Binding Protein 3 (IMA-IGF2BP3-001)

IGF2BP3 is a member of the insulin-like growth factor-II mRNA-binding protein family, implicated in mRNA localization, turnover and translational control. The protein contains several KH (K-homologous) domains, which are important in RNA binding and are known to be involved in RNA synthesis and metabolism. Expression occurs mainly during embryonic development and has been described for some tumors. Thus, IGF2BP3 is considered to be an oncofetal protein (Liao et al., 2005). The presence of high transcript levels of IGF2BP3 in numerous cancer tissues as compared to control tissues indicates that the IGF2BP3 protein might play a functional role in proliferating transformed cells. This hypothesis is supported by the finding that the only non-malignant human tissue expressing the IGF2BP3 transcript is human placenta, a tissue characterized by cell growth and proliferation (Mueller-Pillasch et al., 1997).

There is no specific information about IGF2BP3 expression in GBM in the scientific literature, but the protein has been described as over-expressed in several other malignancies.

For example IGF2BP3 is expressed in clear cell RCC specimen and its expression is associated with advanced stage and grade of primary tumors. Furthermore, positive IGF2BP3 expression is associated with a 5-10 fold increased risk of distant metastases and with a 42%-50% increase in the risk of death from RCC (Hoffmann et al., 2008; Jiang et al., 2006; Jiang et al., 2008). IGF2BP3 expression was also detectable in malignant melanoma in comparison to benign nevi, where no expression was apparent, even in the presence of dysplastic features (Pryor et al., 2008). In patients suffering from esophageal squamous cell carcinoma, T-cells specific for an HLA-A*2402-restricted epitope peptide from IGF2BP3 could be observed in tumor infiltrating lymphocytes (TILs), regional lymph node lymphocytes and peripheral blood lymphocytes in 40% of all cases (Mizukami et al., 2008).

IGF2BP3 is also highly expressed in pancreatic carcinomas. In 2 studies >90% of pancreatic tumor tissue samples showed IGF2BP3 expression after immunostaining whereas non-neoplastic pancreatic tissues were negative for IGF2BP3. Furthermore, the expression increased progressively with tumor stage (Yantiss et al., 2005; Yantiss et al., 2008).

IGF2BP3 expression was also found to be significantly increased in high-grade urothelial tumors while it is generally not expressed in benign urothelium or low-grade urothelial tumors. Moreover, patients with IGF2BP3-positive tumors have a much lower progression-free survival and disease-free survival rate than those with IGF2BP3-negative tumors (Li et al., 2008; Sitnikova et al., 2008; Zheng et al., 2008).

BCAN—Brevican (IMA-BCA-002)

Brevican (BCAN) is a brain-specific member of the lectican family of chondroitin sulfate proteoglycans. Two BCAN isoforms have been reported: a full-length isoform that is secreted into the extracellular matrix and a shorter isoform with a sequence that predicts a glycophosphatidylinositol (GPI) anchor. The secreted isoform is highly expressed from birth through 8 years of age and is downregulated by 20 years of age to low levels that are maintained in the normal adult cortex. The GPI isoform is expressed at uniformly low levels throughout development (Gary et al., 2000). BCAN belongs to a family of proteoglycans usually described as barrier molecules that prevent cell and neurite motility in the adult nervous system (Viapiano and Matthews, 2006). In vivo, BCAN is expressed around the boundaries of the rostral migratory stream (Jaworski and Fager, 2000) and is a major upregulated component of the glial scar after neural injury (Jaworski et al., 1999).

BCAN shows dramatic upregulation in gliomas, where an approximately seven-fold increase in expression over normal levels can be detected (Gary et al., 2000; Gary et al., 1998). Expression is detectable at the invasive borders of experimentally induced tumors (Glass et al., 2005) and is increased in tumors with high infiltrative profiles (Phillips et al., 2006). Clinically, BCAN upregulation correlates with poor survival of patients with high-grade gliomas (Liang et al., 2005). In addition to upregulation of BCAN in glioma, proteolytic processing of the full-length protein may also contribute to invasion (Gary et al., 1998; Nutt et al., 2001). Cleavage of BCAN by metalloproteases of the ADAMTS family is a necessary step in mediating its pro-invasive effect in glioma. By generating a site-specific mutant form which is resistant to ADMATS cleavage it was shown that this "uncleavable" BCAN is unable to enhance glioma cell invasion in vitro and tumor progression in vivo (Zhang et al., 1998; Viapiano et al., 2008). At the molecular level, BCAN promotes EGFR activation, increases the expression of cell-adhesion molecules, and promotes the secretion of fibronectin (Hu et al., 2008).

BCAN mRNA was not detected in samples of adult human cortex from individuals who died without neurological complications. In sharp contrast, BCAN mRNA was detected in every one of 27 surgical samples of human glioma thus proposing that BCAN might be a unique and selective marker in glioma (Jaworski et al., 1996).

BCAN up-regulation in glioma not only leads to a generally increased expression but also to a glioma-specific expression of differentially glycosylated isoforms. Thus, B/bΔg is a full-length product of BCAN mRNA that arises from an incomplete or reduced glycosylation of the core protein. B/bΔg is expressed at very low levels during the second half of prenatal and first days of postnatal development, disappears by the first year of age, and is absent from the normal adult brain but is found in high-grade glioma samples. In one study it could be shown that B/bΔg was present in every sample of high-grade glioma, grades 3 and 4, accounting for half of the total over-expression above control levels for non-cleaved BCAN. Samples that were negative for B/bΔg corresponded to patients diagnosed with low-grade tumors (Viapiano et al., 2005). This high-grade glioma-specific expression could therefore represent a reactivation of early developmental programs, a mechanism that has been implicated in glioma progression (Seyfried, 2001). IMA-BCA-002 contains a potential glycosylation site within its sequence. It has been shown to be very immunogenic in comparison to another peptide derived from BCAN (IMA-BCA-001) that has no glycosylation site. Furthermore, BCAN has been described as selectively over-expressed in a type of GBM-cancer stem cells which show the highest pluripotency and tumorigenicity in vivo (Gunther et al., 2008).

Met Proto-oncogene (Hepatocyte Growth Factor Receptor) (IMA-MET-005)

The MET proto-oncogene c-Met encodes a transmembrane tyrosine kinase receptor that has the capacity to modulate cell proliferation, differentiation, motility, adhesion and invasion. It is activated by the hepatocyte growth factor (HGF) (Giordano et al., 1989; Trusolino and Comoglio, 2002).

c-Met signaling is involved in organ regeneration—as demonstrated for liver and kidney, embryogenesis, haematopoiesis, muscle development, and in the regulation of migration and adhesion of normally activated B cells and monocytes (Naldini et al., 1991; Mizuno et al., 1993; Bladt et al., 1995; Schmidt et al., 1995; Zarnegar and Michalopoulos, 1995; van der Voort et al., 1997; Beilmann et al., 2000).

Studies in various tumor types have demonstrated several mechanisms for c-Met activation, including HGF/c-Met autocrine loop, activating point mutations, TPR-Met fusion protein, and failure to cleave c-MET into the α and β chains (Park et al., 1986; Mondino et al., 1991; Ebert et al., 1994; Schmidt et al., 1997; Olivero et al., 1999; Park et al., 1999; Di Renzo et al., 2000). Constitutive c-Met activation through phosphorylation has also been identified as an important mechanism of oncogenesis in human clear-cell RCC (Nakaigawa et al., 2006).

Furthermore, numerous studies indicated the involvement of c-Met over-expression in malignant transformation and invasiveness of malignant cells. c-Met mediates the multi-functional and potentially oncogenic activities of HGF (Bottaro et al., 1991; Rubin et al., 1993; Zarnegar and Michalopoulos, 1995). By binding to the receptor, HGF induces autophosphorylation of c-Met and activates downstream signaling events including the ras, phosphatidylinositol 3'-kinase, phospholipase C, and mitogen-activated protein kinase-related pathways (Naldini et al., 1991; Ponzetto et al., 1993; Montesano et al., 1998; Furge et al., 2000; Dong et al., 2001; Furge et al., 2001). The c-Met gene is expressed predominantly in epithelial cells and is over-expressed in several malignant tissues and cell lines (Di Renzo et al., 1995; Ferracini et al., 1995; Tuck et al., 1996; Koochekpour et al., 1997; Fischer et al., 1998; Ramirez et al., 2000; Li et al., 2001; Maulik et al., 2002; Qian et al., 2002).

c-Met over-expression, often induced by tumor hypoxia, leads to constitutive activation of the receptor and correlates with poor prognosis. Silencing the endogenous c-MET gene, results in impairment of the execution of the full invasive growth program in vitro, lack of tumor growth and decreased generation of experimental metastases in vivo (Corso et al., 2008).

c-MET overexpression has been described in GBM (Tso et al., 2006). c-Met is correlated with the histological grade of the tumor suggesting that the creation of HGF/c-MET autocrine loop occurs along with the progression of astrocytic brain tumors. Therefore, HGF is thought to exhibit potent migration/invasion-inducing activity for GBM cells bearing the c-Met receptor (Moriyama et al., 1999). The c-Met promoter contains hypoxia inducible factor-1 binding sites, thus hypoxia was shown to activate the c-Met promoter and upregulate its expression. Approximately half of all human GBMs are thought to respond to hypoxia with an induction of c-Met, which can enhance the stimulating effect of HGF on tumor cell migration (Eckerich et al., 2007) and may attract neural stem cells to the tumor (Kendall et al., 2008). c-Met and EGFR are frequently co-expressed in malignant astrocytoma (Reznik et al., 2008). It was shown that the activating phosphorylation site on the c-Met receptor is highly responsive to EGFRvIII levels proposing a crosstalk between EGFRvIII and the c-Met receptor in glioblastoma (Huang et al., 2007a; Huang et al., 2007b). MET has been suggested as a marker for cancer stem cells in GBM (Nam et al., 2008). Another study showed, that MET was selectively over-expressed in a distinct subtype of GBM-derived cancer stem cells (Gunther et al., 2008).

Intermediate results of a phase II study in patients with recurrent GBM using AMG102, a human neutralizing antibody against HGF, suggest that in some patients the disease may be dependent on the c-MET:HGF signaling pathway as out of 18 patients treated, 1 had a partial response, 1 had a minor response and 2 had stable disease (Reardon et al., 2008).

Interestingly, there is some evidence for interactions of MET signalling with the Wnt/beta-catenin pathway frequently upregulated in colon cancer. MET can be activated by Prostaglandin E2 (PGE2) and PGE2-activated c-Met associates with β-catenin and increases its tyrosine phosphorylation thereby inducing colon cancer cell invasiveness (Pai et al., 2003). Recently, mutual activation of MET and beta-catenin has been described, resulting in a positive feedback loop between these two key players in colorectal tumorigenesis (Rasola et al., 2007).

The c-Met mRNA expression level in primary CRC tumors (n=36) is an important predictive marker for early-stage invasion and regional disease metastasis, thus correlating directly with colon cancer stage (Takeuchi et al., 2003). Another analysis of c-Met expression of 130 CRC samples showed overexpression (T/N>2.0) of c-Met in 69% primary CRC and significantly higher c-Met levels in CRC with blood vessel invasion (P=0.04), and in advanced stage (P=0.04) supporting the role for c-Met in human CRC progression and metastasis (Zeng et al., 2004). In another study 69% and 48% of 60 colon adenocarcinomas showed a greater than 2- and greater than 10-fold elevation in c-Met mRNA, respectively, compared to adjacent normal mucosa (Kammula et al., 2007). Thus, increased c-Met signalling is a common occurrence in early stage CRC, but with even greater expression occurring in advanced and metastatic disease.

lates signaling pathways that control diverse cellular functions including cell morphology, migration, endocytosis and cell cycle progression. CDC42 was found to be highly overexpressed in glioblastoma.

WO 2004/067023 describes MHC Class I-restricted peptides derived from the tumor associated antigen survivin, which peptides are capable of binding to Class I HLA molecules at a high affinity.

Secreted phosphoprotein 1 (SPP1), also known as bone sialoprotein I (BSP-1), early T-lymphocyte activation (ETA-1), and most commonly as osteopontin (OPN), is a human gene product, which is also conserved in other species. Osteopontin has been implicated as an important factor in bone remodeling. Specifically, research suggests it plays a role in anchoring osteoclasts to the mineral matrix of bones. The organic part of bone is about 20% of the dry weight, and counts in, other than osteopontin, collagen type I, osteocalcin, osteonectin, bone sialo protein and alkaline phosphatase. Collagen type I counts for 90% of the protein mass.

OPN binds to several integrin receptors including α4β1, α9β1, and α9β4 expressed by leukocytes. These receptors have been well-established to function in cell adhesion, migration, and survival in these cells. Therefore, recent research efforts have focused on the role of OPN in mediating such responses.

Osteopontin is expressed in a range of immune cells, including macrophages, neutrophils, dendritic cells, and T and B cells, with varying kinetics. OPN is reported in act as an immune modulator in a variety of manners. Firstly, it has chemotactic properties, which promote cell recruitment to

TABLE 4

Additional immunogenic peptides useful in a composition of the invention

| SEQ ID NO | Peptide ID | Sequence | Gene Symbol | Function | binds to MHC |
|---|---|---|---|---|---|
| 9 | PTP-003 | AIIDGVESV | PTPRZ1 | | HLA-A*02 |
| 10 | PTP-005 | KVFAGIPTV | PTPRZ1 | | HLA-A*02 |
| 11 | CHI-001 | SLWAGVVVL | CHI3L2 | | HLA-A*02 |
| 12 | BIR-002 | TLGEFLKLDRERAKN | BIRC5 | | HLA-DR and HLA-A*02 |
| 13 | (HBV-001) | FLPSDFFPSV | | control peptide | |
| 14 | CDC42-001 | DDPSTIEKLAKNKQKP | CDC42 | | HLA-DR |
| 15 | CDC42-002 | NKQKPITPETAEKLARD | CDC42 | | HLA-DR |
| 16 | SPP1-001 | NGAYKAIPVAQDLNAPS | SPP1 | | HLA-DR |
| 17 | BIR-002a | TLGEFLKLDRERAKD | Survivin | | HLA-DR and HLA-A*02 |
| 18 | BIR-002b | FTELTLGEF | Survivin | | HLA-A1 |
| 19 | BIR-002c | LMLGEFLKL | Survivin | | HLA-A2 |
| 20 | BIR-002d | EPDLAQCFY | Survivin | | HLA-B35 |

SEQ ID NO:14, SEQ ID:NO 15 and SEQ ID NO:16 are disclosed in WO 2007/028574, CDC42 (cell division cycle 42) is a protein involved in regulation of the cell cycle. The protein is a small GTPase of the Rho-subfamily, which reguinflammatory sites. It also functions as an adhesion protein, involved in cell attachment and wound healing. In addition, OPN mediates cell activation and cytokine production, as well as promoting cell survival by regulating apoptosis.

Activated T cells are promoted by IL-12 to differentiate towards the Th1 type, producing cytokines including IL-12 and IFNγ. OPN inhibits production of the Th2 cytokine IL-10, which leads to enhanced Th1 response. OPN influences cell-mediated immunity and has Th1 cytokine functions. It enhances B cell immunoglobulin production and proliferation. Recent studies in 2008 suggest that OPN also induces mast cell degranulation. [Nagasaka A, Matsue H, Matsushima H, et al. (February 2008). "Osteopontin is produced by mast cells and affects IgE-mediated degranulation and migration of mast cells". Eur. J. Immunol. 38 (2): 489-99] The researchers observed that IgE-mediated anaphylaxis was significantly reduced in OPN knock-out mice compared to wild type mice. The role of OPN in activation of macrophages has also been implicated in a cancer study, when researchers discovered that OPN-producing tumors were able to induce macrophage activation compared to OPN-deficient tumors.

OPN is an important anti-apoptotic factor in many circumstances. OPN blocks the activation-induced cell death of macrophages and T cells as well as fibroblasts and endothelial cells exposed to harmful stimuli. OPN prevents non-programmed cell death in inflammatory colitis.

The fact that OPN interacts with multiple cell surface receptors which are ubiquitously expressed makes it an active player in many physiological and pathological processes including wound healing, bone turnover, tumorigenesis, inflammation, ischemia and immune responses. Therefore, manipulation of plasma OPN levels may be useful in the treatment of autoimmune diseases, cancer metastasis, osteoporosis and some forms of stress.

It has been shown that OPN drives IL-17 production; OPN is overexpressed in a variety of cancers, including lung cancer, breast cancer, colorectal cancer, stomach cancer, ovarian cancer, melanoma and mesothelioma; OPN contributes both glomerulonephritis and tubulointerstitial nephritis; and OPN is found in atheromatous plaques within arteries. Thus, manipulation of plasma OPN levels may be useful in the treatment of autoimmune diseases, cancer metastasis, osteoporosis and some forms of stress.

Protein Tyrosine Phosphatase, Receptor-Type, Zetal (PTPRZ1, PTP-ξ)

PTPRZ1 is a member of the receptor type protein tyrosine phosphatase family and encodes a single-pass type I membrane protein with two cytoplasmic tyrosine-protein phosphatase domains, an alpha-carbonic anhydrase domain and a fibronectin type-III domain. Expression of this gene is induced in gastric cancer cells (Wu et al., 2006), in breast cancer (Perez-Pinera et al., 2007), in the remyelinating oligodendrocytes of multiple sclerosis lesions (Harroch et al., 2002), and in human embryonic kidney cells under hypoxic conditions (Wang et al., 2005).

Both the protein and transcript are overexpressed in glioblastoma cells, promoting their haptotactic migration (Lu et al., 2005), and genomic DNA amplification in glioblastoma (Mulholland et al., 2006).

Chitinase 3-Like 2 (CHI3L2)

CHI3L2 was originally identified from chondrocytes and is upregulated e.g. in osteoarthritis (Steck et al., 2002). Although the protein is not well characterized yet, it is most likely secreted into the extracellular space. It has been frequently described as a target antigen in rheumatoid arthritis. Experimental anti-angiogenesis induction by siRNA transfection (VEGF-A) of a human glioma cell line caused upregulation of CHI3L2.

Survivin (BIRC5)

Expression of BIRC5 (survivin), a member of the inhibitor of apoptosis protein (IAP) family, is elevated in fetal tissues and in various human cancers. Survivin seems to be capable of regulating both cellular proliferation and apoptotic cell death. Especially in glioblastoma, very high levels of survivin expression are detectable (Angileri et al., 2008). It is suggested that survivin overexpression in brain gliomas might play an important role in malignant proliferation, anti-apoptosis and angiogenesis (Zhen et al., 2005; Liu et al., 2006). Especially for glioblastoma, but also for other tumor entities, survivin expression was significantly associated with malignancy grade (with highest survivin expression in glioblastoma) and shorter overall survival times compared with patients who had survivin-negative tumors (Kajiwara et al., 2003; Saito et al., 2007; Uematsu et al., 2005; Mellai et al., 2008; Grunda et al., 2006; Xie et al., 2006; Sasaki et al., 2002; Chakravarti et al., 2002).

Hepatitis B Core Antigen

For the Hepatitis B virus (HBV) core protein HBc immunogenic peptides are well known (Bertoletti et al., 1993; Livingston et al., 1997). A ten-amino acid peptide from HBc may be included as a positive control for patients' immunocompetence and successful immunizations into cancer vaccines based on the present disclosure.

In a preferred embodiment of the invention the pharmaceutical composition comprises at least two peptides containing an amino acid sequence according to SEQ ID NO:1 and an amino acid sequence according to SEQ ID NO:12 or SEQ ID NO:17.

In a preferred embodiment of the invention the pharmaceutical composition comprises at least two peptides containing an amino acid sequence according to SEQ ID NO:1 and an amino acid sequence according to SEQ ID NO:2 and/or SEQ ID NO:17.

In a preferred embodiment of the invention the pharmaceutical composition comprises at least two peptides containing an amino acid sequence according to SEQ ID NO:SEQ ID NO:3 and an amino acid sequence according to SEQ ID NO:2 and/or SEQ ID NO:17.

In a preferred embodiment of the invention the pharmaceutical composition comprises at least two peptides containing an amino acid sequence according to SEQ ID NO:SEQ ID NO:1 and an amino acid sequence according to SEQ ID NO:7 and optionally SEQ ID NO:17.

In a preferred embodiment of the invention the pharmaceutical composition comprises at least two peptides containing an amino acid sequence according to SEQ ID NO:SEQ ID NO:2 and an amino acid sequence according to SEQ ID NO:7 and optionally SEQ ID NO:17.

In a preferred embodiment of the invention the pharmaceutical composition comprises at least two peptides containing an amino acid sequence according to SEQ ID NO:SEQ ID NO:3 and an amino acid sequence according to SEQ ID NO:7 and optionally SEQ ID NO:17.

In an even more preferred embodiment the pharmaceutical composition comprises at least one more peptide containing an amino acid sequence selected from the group consisting of SEQ ID NO:2 to SEQ ID NO:11 and SEQ ID NO:14 to SEQ ID NO:20 and/or an amino acid sequence that is at least 80% identical to that of SEQ ID NO:2 to SEQ ID NO:11 or SEQ ID NO:14 to SEQ ID NO:20 and/or a polynucleotide containing a nucleic acid encoding SEQ ID NO:2 to SEQ ID NO:11 or SEQ ID NO:14 to SEQ ID NO:20 or the variant amino acid sequence, and a pharmaceutically acceptable carrier.

Further preferred embodiments of the invention comprise at least 3, 4, 5, 6, 7, 8, 9, 10, 11 12, 13, 14, 15, 16, 17 or 18 peptides containing an amino acid sequence selected from the group consisting of SEQ ID NO:1 to SEQ ID NO:12 and SEQ ID NO:14 to SEQ ID NO:20 and/or an amino acid sequence that is at least 80% identical to that of SEQ ID NO:1 to SEQ ID NO:12 and/or a polynucleotide containing a nucleic acid encoding SEQ ID NO:1 to SEQ ID NO:12 and SEQ ID NO:14 to SEQ ID NO:20 or the variant amino acid sequence, and a pharmaceutically acceptable carrier.

The pharmaceutical composition can furthermore contain additional peptides and/or excipients to be more effective, as will be further explained below.

By a "variant amino acid sequence" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence. For example, a peptide may be modified so that it at least maintains, if not improves, the ability to interact with and bind a suitable MHC molecule, such as HLA-A or -DR, and so that it at least maintains, if not improves, the ability to generate activated CTL which can recognise and kill cells which express a polypeptide containing an amino acid sequence as defined in the aspects of the invention. As can be derived from the database, certain positions of HLA-A binding peptides are typically anchor residues forming a core sequence fitting to the binding motif of the HLA binding groove.

Those amino acid residues that are not essential to interact with the T-cell receptor can be modified by replacement with another amino acid whose incorporation does not substantially affect T-cell reactivity and does not eliminate binding to the relevant MHC. Thus, apart from the proviso given, the peptide of the invention may be any peptide (by which term the inventors include oligopeptide or polypeptide) which includes the amino acid sequences or a portion or variant thereof as given.

It is furthermore known for MHC-class II presented peptides that these peptides are composed of a "core sequence" having a certain HLA-specific amino acid motif and, optionally, N- and/or C-terminal extensions which do not interfere with the function of the core sequence (i.e. are deemed as irrelevant for the interaction of the peptide and the T-cell). The N- and/or C-terminal extensions can, for example, be between 1 to 10 amino acids in length, respectively. These peptide can be used either directly to load MHC class II molecules or the sequence can be cloned into the vectors according to the description herein below. As these peptides form the final product of the processing of larger peptides within the cell, longer peptides can be used as well. The peptides of the invention may be of any size, but typically they may be less than 100,000 in molecular weight, preferably less than 50,000, more preferably less than 10,000, more preferably less than 5,000, more preferably less than 2,500 and typically about 1000 to 2000. In terms of the number of amino acid residues, the peptides of the invention may have fewer than 1000 residues, preferably fewer than 500 residues, more preferably fewer than 100 residues. Accordingly the present invention provides also compositions of peptides and variants thereof wherein the peptide or variant has an overall length of between 8 and 100, preferably between 8 and 30, and most preferred between 8 and 17, namely 8, 9, 10, 11, 12, 13, 14, 15 or 16 amino acids. Preferred are peptides with a core sequence selected from a group consisting of SEQ ID NO:8, SEQ ID NO:12 and SEQ ID NO:14 to SEQ ID NO:20 with extensions of 1 to 10 amino acids on the C-terminal and/or the N-terminal, more preferred the overall number of these flanking amino acids is 1 to 12, more preferred 1 to 10, more preferred 1 to 8, more preferred 1 to 6, wherein the flanking amino acids can be distributed in any ratio to the C-terminus and the N-terminus (for example all flanking amino acids can be added to one terminus, or the amino acids can be added equally to both termini or in any other ratio), provided that the peptide is still able to bind to an HLA molecule in the same way as said peptide according to any of the SEQ ID NO:8, SEQ ID NO:12 and SEQ ID NO:14 to SEQ ID NO:20.

Correspondingly, variants that induce T-cells cross-reacting with a peptide of the invention are often length variants.

If a peptide is longer than around 12 amino acid residues is used directly to bind to a MHC class II molecule, it is preferred that the residues that flank the core HLA binding region do not substantially affect the ability of the peptide to bind specifically to the binding groove of the MHC class II molecule or to present the peptide to the CTL. However, as already indicated above, it will be appreciated that larger peptides may be used, especially when encoded by a polynucleotide, since these larger peptides may be fragmented by suitable antigen-presenting cells. Furthermore the flanking amino acids can reduce the speed of peptide degradation in vivo so that the amount of the actual peptide available to the CTLs is higher compared to the peptide without flanking amino acids.

It is also possible, that MHC class I epitopes, although usually between 8-10 amino acids long, are generated by peptide processing from longer peptides or proteins that include the actual epitope. Similar to MHC class II epitopes, it is preferred that the flanking residues of elongated precursor peptides upstream and/or downstream of the N- and C-terminus, of the actual epitope do not substantially affect the presentation of the peptide to the CTL nor mask the sites for proteolytic cleavage necessary to yield the actual epitope mediated by processing of the elongated peptide.

Preferred are peptides with a core sequence consisting of SEQ ID NO:1 to SEQ ID NO:7 and SEQ ID 9 to SEQ ID 11 with extensions of 1 to 10 amino acids on the C-terminal and/or the N-terminal, more preferred the overall number of these flanking amino acids is 1 to 12, more preferred 1 to 10, more preferred 1 to 8, more preferred 1 to 6, wherein the flanking amino acids can be distributed in any ratio to the C-terminus and the N-terminus (for example all flanking amino acids can be added to one terminus, or the amino acids can be added equally to both termini or in any other ratio), provided that the peptide is still able to bind to an HLA molecule in the same way as said peptide according to any of the of SEQ ID NO:1 to SEQ ID NO:7 and SEQ ID NO:9 to SEQ ID NO:11.

Accordingly the present invention also provides peptides and variants of MHC class I epitopes having an overall length of between 8 and 100, preferably between 8 and 30, and most preferred between 8 and 18 namely 8, 9, 10, 11, 12, 13, 14, 15, 16 or 17 amino acids.

Of course, the peptide or variant according to the present invention will have the ability to bind to a molecule of the human MHC class I or II. Binding of a peptide or a variant to a MHC complex may be tested by methods known in the art, for example those described in the examples of the present invention below or those described in the literature for different MHC class II alleles (e.g. Vogt A B, Kropshofer H, Kalbacher H, Kalbus M, Rammensee H G, Coligan J E, Martin R; Ligand motifs of HLA-DRB5*0101 and DRB1*1501 molecules delineated from self-peptides; J. Immunol. 1994; 153 (4):1665-1673; Malcherek G, Gnau V, Stevanović S, Rammensee H G, Jung G, Melms A; Analysis of allele-specific contact sites of natural HLA-DR17 ligands; J. Immunol. 1994; 153(3):1141-1149; Manici S, Sturniolo T, Imro M A, Hammer J, Sinigaglia F, Noppen C, Spagnoli G, Mazzi B, Bellone M, Dellabona P, Protti M P; Melanoma cells present a MAGE-3 epitope to CD4(+) cytotoxic T cells in association with histocompatibility leukocyte antigen DR11; J Exp Med. 1999; 189(5): 871-876; Hammer J, Gallazzi F, Bono E, Karr R W, Guenot J, Valsasnini P, Nagy Z A, Sinigaglia F; Peptide binding specificity of HLA-DR4 molecules: correlation with rheumatoid arthritis association; J. Exp Med. 1995 181(5): 1847-1855; Tompkins S M, Rota P A, Moore J C, Jensen P E; A europium fluoroimmunoassay for measuring binding of antigen to class II MHC glycoproteins; J Immunol Methods. 1993; 163(2): 209-216; Boyton R J, Lohmann T, Londei M, Kalbacher H, Halder T, Frater A J, Douek D C, Leslie D G, Flavell R A, Altmann D M; Glutamic acid decarboxylase T lymphocyte responses associated with susceptibility or resistance to type I diabetes: analysis in disease discordant human twins, non-obese diabetic mice and HLA-DQ transgenic mice; Int Immunol. 1998 (12):1765-1776).

Additional N- and/or C-terminally located stretches of amino acids that are not necessarily forming part of the peptide that functions as the actual epitope for MHC molecules but may, nevertheless, be important to provide for an efficient introduction of the peptide according to the present invention into the cells (see above). In one embodiment of the present invention, the peptide of the present invention is a fusion protein which comprises, for example, the 80 N-terminal amino acids of the HLA-DR antigen-associated invariant chain (p33, in the following "Ii") as derived from the NCBI, GenBank Accession-number X00497 (Strubin, M., Mach, B. and Long, E. O. The complete sequence of the mRNA for the HLA-DR-associated invariant chain reveals a polypeptide with an unusual transmembrane polarity EMBO J. 3 (4), 869-872 (1984)).

Preferred are pharmaceutical compositions, wherein the peptides have an overall length of between 8 and 100, preferably between 8 and 30, and most preferred between 8 and 17 or 9, 10, 11, 12, 13, 14, 15, or 16 amino acids.

In addition, the peptide or variant may be modified further to improve stability and/or binding to MHC molecules to elicit a stronger immune response. Methods for such an optimisation of a peptide sequence are well known in the art and include, for example, the introduction of reverse peptide bonds or non-peptide bonds.

Thus, according to another aspect the invention provides a pharmaceutical composition, wherein at least one peptide or variant includes non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) J. Immunol. 159, 3230-3237, incorporated herein by reference. This approach involves making pseudopeptides containing changes involving the backbone, and not the orientation of side chains. Meziere et al (1997) show that for MHC and T helper cell responses, these pseudopeptides are useful. Retro-inverse peptides, containing NH—CO bonds instead of CO—NH peptide bonds, are much more resistant to proteolysis.

A non-peptide bond is, for example, —CH2—NH, —CH2S—, —CH2CH2—, —CH=CH—, —COCH2—, —CH(OH)CH2—, and —CH2SO—. U.S. Pat. No. 4,897,445 provides a method for the solid phase synthesis of non-peptide bonds (—CH2—NH) in polypeptide chains that involves polypeptides synthesised by standard procedures and the non-peptide bond synthesised by reacting an amino aldehyde and an amino acid in the presence of NaCNBH3.

Peptides comprising the sequences of the invention described above may be synthesized with additional chemical groups present at their amino and/or carboxy termini, to enhance, for example, the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxy-carbonyl group may be placed at the peptides' amino termini. Additionally, e.g. the hydrophobic group, t-butyloxycarbonyl, or an amido group may be added to the peptides' carboxy termini.

Further, all peptides of the invention may be synthesised to alter their steric configuration. For example, the D-isomer of one or more of the amino acid residues of the peptide may be used, rather than the usual L-isomer. Still further, at least one of the amino acid residues of the peptides of the invention may be substituted by one of the well known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarised e.g. in R. Lundblad, Chemical Reagents for Protein Modification, 3rd ed. CRC Press, 2005, which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulfonic acid (TNBS), amide modification of carboxyl groups and sulfhydryl modification by performic acid oxidation of cysteine to cysteic acid, formation of mercurial derivatives, formation of mixed disulfides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley & Sons NY 1995-2000) for more extensive methodology relating to chemical modification of proteins.

Successful modification of therapeutic proteins and peptides with PEG is often associated with an extension of circulatory half-life while cross-linking of proteins with glutaraldehyde, polyethyleneglycol diacrylate and formaldehyde is used for the preparation of hydrogels. Chemical modification of allergens for immunotherapy is often achieved by carbamylation with potassium cyanate.

Generally, peptides and variants (at least those containing peptide linkages between amino acid residues) may be synthesised e.g. using the Fmoc-polyamide mode of solid-phase peptide synthesis as disclosed by Lu et al (1981) J. Org. Chem. 46, 3433 and references therein.

Purification may be effected by any one, or a combination of, techniques such as recrystallization, size exclusion chromatography, ion-exchange chromatography, hydrophobic interaction chromatography and (usually) reverse-phase high performance liquid chromatography using e.g. acetonitril/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

A further aspect of the invention provides a nucleic acid (e.g. polynucleotide) encoding a peptide or variant of the invention. The polynucleotide may be e.g. DNA, cDNA, PNA, CNA, RNA, either single- and/or double-stranded, or native or stabilised forms of polynucleotides, such as e.g. polynucleotides with a phosphorothioate backbone, or combinations thereof and it may or may not contain introns so long as it codes for the peptide. Of course, it is only peptides containing naturally occurring amino acid residues joined by naturally occurring peptide bonds are encodable by a polynucleotide. A still further aspect of the invention provides an expression vector capable of expressing a polypeptide according to the invention. Expression vectors for different cell types are well known in the art and can be selected without undue experimentation.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Guidance can be found e.g. in Sambrook et al (1989) Molecular Cloning, A Laboratory Manual, Cold Spring Harbor Laboratory, Cold Spring Harbor, N.Y.

In a particularly preferred embodiment of the invention, however, the pharmaceutical composition comprises at least two peptides consisting of amino acid sequences according to SEQ ID NO:1 to SEQ ID NO:12.

The optimum amount of each peptide to be included in the vaccine and the optimum dosing regimen can be determined by one skilled in the art without undue experimentation. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred routes of peptide injection are s.c., i.d., i.p., i.m., and i.v. Preferred routes of DNA injection are i.d., i.m., s.c., i.p. and i.v. Doses of e.g. between 1 and 500 mg 50 µg and 1.5 mg, preferably 125 µg to 500 µg, of peptide or DNA may be given and will depend from the respective peptide or DNA. Doses of this range were successfully used in previous trials (Brunsvig P F, Aamdal S, Gjertsen M K, Kvalheim G, Markowski-Grimsrud C J, Sve I, Dyrhaug M, Trachsel S, Møller M, Eriksen J A, Gaudernack G; Telomerase peptide vaccination: a phase I/II study in patients with non-small cell lung cancer; Cancer Immunol Immunother. 2006; 55(12):1553-1564; M. Staehler, A. Stenzl, P. Y. Dietrich, T. Eisen, A. Haferkamp, J. Beck, A. Mayer, S. Walter, H. Singh, J. Frisch, C. G. Stief; An open label study to evaluate the safety and immunogenicity of the peptide based cancer vaccine IMA901, ASCO meeting 2007; Abstract No 3017)

The inventive pharmaceutical composition may be compiled such that the selection, number and/or amount of peptides present in the composition is/are tissue, cancer, and/or patient-specific. For instance the exact selection of peptides can be guided by expression patterns of the parent proteins in a given tissue to avoid side effects. The selection may be dependent from the specific type of cancer that the patient to be treated is suffering from as well as the status of the disease, earlier treatment regimens, the immune status of the patient, and, of course, the HLA-haplotype of the patient. Furthermore, the vaccine according to the invention can contain individualised components, according to personal needs of the particular patient. Examples are different amounts of peptides according to the expression of the related TAAs in the particular patient, unwanted side-effects due to personal allergies or other treatments, and adjustments for secondary treatments following a first round or scheme of treatment.

For compositions to be used as a vaccine for GBM for example, peptides whose parent proteins are expressed in high amounts in normal tissues will be avoided or be present in low amounts in the composition of the invention. On the other hand, if it is known that the tumor of a patient expresses high amounts of a certain protein the respective pharmaceutical composition for treatment of this cancer may be present in high amounts and/or more than one peptide specific for this particular protein or pathway of this protein may be included. The person of skill will be able to select preferred combinations of immunogenic peptides by testing, for example, the generation of T-cells in vitro as well as their efficiency and overall presence, the proliferation, affinity and expansion of certain T-cells for certain peptides, and the functionality of the T-cells, e.g. by analysing the IFN-gamma production (see also examples below). Usually, the most efficient peptides are then combined as a vaccine for the purposes as described above.

A suitable vaccine will preferably contain between 1 and 20 peptides, more preferably 2, 3, 4, 5, 6, 7, 8, 9, 10, 11, 12, 13, 14, 15, 16, 17, 18, 19, or 20 different peptides, further preferred 6, 7, 8, 9, 10 11, 12, 13, or 14 different peptides, and most preferably 10, 11, 12, 13 or 14 different peptides. The length of the peptide for use in a cancer vaccine may be any suitable peptide. In particular, it may be a suitable 9-mer peptide or a suitable 8-mer or 9-mer or 10-mer or 11-mer peptide or 12-mer, 13-mer, 14-mer or 15-mer. Longer peptides may also be suitable, 9-mer or 10-mer peptides as described in the attached Tables 1 and 2 are preferred for MHC class I-peptides, while 12- to 15-mers are preferred for MHC class II peptides.

The peptide(s) constitute(s) a tumor or cancer vaccine. It may be administered directly into the patient, into the affected organ or systemically, or applied ex vivo to cells derived from the patient or a human cell line which are subsequently administered to the patient, or used in vitro to select a sub-population from immune cells derived from the patient, which are then re-administered to the patient.

The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and Longenecker et al (1993) Ann. NY Acad. Sci. 690, 276-291). The peptide may also be tagged, or be a fusion protein, or be a hybrid molecule. The peptides whose sequence is given in the present invention are expected to stimulate CD4 T cells or CD8 CTL. However, stimulation is more efficient in the presence of help provided by T-cells positive for the opposite CD. Thus, for MHC Class II epitopes which stimulate CD4 T cells the fusion partner or sections of a hybrid molecule suitably provide epitopes which stimulate CD8-positive T-cells. On the other hand, for MHC Class I epitopes which stimulate CD8 CTL the fusion partner or sections of a hybrid molecule suitably provide epitopes which stimulate CD4-positive T cells. CD4- and CD8-stimulating epitopes are well known in the art and include those identified in the present invention.

Pharmaceutically acceptable carriers are well known and are usually liquids, in which an active therapeutic agent is formulated. The carrier generally does not provide any pharmacological activity to the formulation, though it may provide chemical and/or biological stability, release characteristics, and the like. Exemplary formulations can be found, for example, in Alfonso R. Gennaro. Remington: The Science and Practice of Pharmacy, 20th Edition. Baltimore, Md.: Lippincott Williams & Wilkins, 2000 and include, but are not limited to, saline, water, buffered water, 0.3% glycine, hyaluronic acid, dextrose and the like. Recently, it was found that certain fat emulsions, which have been in use for many years for intravenous nutrition of human patients, can also act as a vehicle for peptides. Two examples of such emulsions are the available commercial fat emulsions known as Intralipid and Lipofundin. "Intralipid" is a registered trademark of Kabi Pharmacia, Sweden, for a fat emulsion for intravenous nutrition, described in U.S. Pat. No. 3,169,094. "Lipofundin" is a registered trademark of B. Braun Melsungen, Germany. Both contain soybean oil as fat (100 or 200 g in 1,000 ml distilled water: 10% or 20%, respectively). Egg-yolk phospholipids are used as emulsifiers in Intralipid (12 g/l distilled water) and egg-yolk lecithin in Lipofundin (12 g/l distilled water). Isotonicity results from the addition of glycerol (25 g/l) both in Intralipid and Lipofundin.

To elicit an immune response it is usually necessary to include adjuvants that render the composition more immunogenic. Thus in a preferred embodiment of the invention the pharmaceutical composition further comprises at least one suitable adjuvant.

Adjuvants are substances that non-specifically enhance or potentiate the immune response (e.g., immune responses mediated by CTLs and helper-T (TH) cells to an antigen, and would thus be considered useful in the medicament of the present invention. Suitable adjuvants include, but are not limited to 1018 ISS, aluminium salts, Amplivax, AS15, BCG, CP-870,893, CpG7909, CyaA, Mologen's dSLIM, GM-CSF, IC30, IC31, Imiquimod, ImuFact IMP321, interferon-alpha or -beta, IS Patch, ISS, ISCOMs, Juvlmmune, LipoVac, MF59, monophosphoryl lipid A, and other non-toxic LPS derivatives, Montanide IMS 1312, Montanide ISA 206, Montanide ISA 50V, Montanide ISA-51, OK-432, OM-174, OM-197-MP-EC, ONTAK, PepTel® vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil, or Superfos. Adjuvants such as Imiquimod, Resiquimod, incomplete Freund's, interferon-alpha or GM-CSF are preferred. Several immunological adjuvants (e.g., MF59) specific for dendritic cells and their preparation have been described previously (Dupuis M, Murphy T J, Higgins D, Ugozzoli M, van Nest G, Ott G, McDonald D M; Dendritic cells internalize vaccine adjuvant after intramuscular injection; Cell Immunol. 1998; 186(1):18-27; Allison AC; The mode of action of immunological adjuvants; Dev Biol Stand. 1998; 92:3-11). Also cytokines may be used. Several cytokines have been directly linked to influencing dendritic cell migration to lymphoid tissues (e.g., TNF-α), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, Cunningham H T, Carbone D P; IL-12 and mutant P53 peptide-pulsed dendritic cells for the specific immunotherapy of cancer; J Immunother Emphasis Tumor Immunol. 1996 (6):414-418).

CpG immunostimulatory oligonucleotides have also been reported to enhance the effects of adjuvants in a vaccine setting. Without bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T-cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nano particles, lipid emulsions or similar formulations, which are especially necessary for inducing a strong response when the antigen is relatively weak. They also accelerate the immune response and enabled the antigen doses to be reduced by approximately two orders of magnitude, with comparable antibody responses to the full-dose vaccine without CpG in some experiments (Arthur M. Krieg, Therapeutic potential of Toll-like receptor 9 activation, Nature Reviews, Drug Discovery, 2006, 5, 471-484). U.S. Pat. No. 6,406,705 B1 describes the combined use of CpG oligonucleotides, non-nucleic acid adjuvants and an antigen to induce an antigen-specific immune response. A commercially available CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), Poly (I:C) (e.g. polyI:C12U), non-CpG bacterial DNA or RNA as well as immunoactive small molecules and antibodies such as imidazoquinolines, cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab and SC58175, which may act therapeutically and/or as an adjuvant. The amounts and concentrations of adjuvants and additives useful in the context of the present invention can readily be determined by the skilled artisan without undue experimentation.

Preferred adjuvants are dSLIM, BCG, OK432, imiquimod, resiquimod, GM-CSF, interferon-alpha, PeviTer and Juvlmmune or combinations thereof.

In a preferred embodiment the pharmaceutical composition according to the invention the adjuvant is selected from the group consisting of colony-stimulating factors, such as Granulocyte Macrophage Colony Stimulating Factor (GM-CSF, sargramostim), imiquimod, resiquimod, and interferon-alpha.

In a preferred embodiment of the pharmaceutical composition according to the invention, the adjuvant is imiquimod or resiquimod. In a preferred embodiment of the pharmaceutical composition according to the invention, the adjuvant is the combination of GM-CSF and imiquimod.

This composition is used for parenteral administration, such as subcutaneous, intradermal, intramuscular, intraperitoneal or for oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavours, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients, 3rd Ed. 2000, American Pharmaceutical Association and pharmaceutical press. The composition can be used for a prevention, prophylaxis and/or therapy of adenomatous or cancerous diseases, preferably CRC.

Cytotoxic T-cells (CTLs) recognise an antigen in the form of a peptide bound to an MHC molecule rather than the intact foreign antigen itself. The MHC molecule itself is located at the cell surface of an antigen presenting cell. Thus, an activation of CTLs is only possible if a trimeric complex of peptide antigen, MHC molecule, and APC is present. Correspondingly, it may enhance the immune response if not only the peptide is used for activation of CTLs but if additionally APCs with the respective MHC molecule are added.

Therefore, in a preferred embodiment the pharmaceutical composition according to the present invention additionally contains at least one antigen presenting cell.

The antigen-presenting cell (or stimulator cell) typically has an MHC class I or II molecule on its surface and in one embodiment is substantially incapable of itself loading the MHC class I or II molecule with the selected antigen. As is described in more detail below, the MHC class I or II molecule may readily be loaded with the selected antigen in vitro.

Preferably the mammalian cell lacks or has a reduced level or has reduced function of the TAP peptide transporter. Suitable cells which lack the TAP peptide transporter include T2, a human peptide loading deficient cell line that is available from the American Type Culture Collection, 12301 Parklawn Drive, Rockville, Md. 20852, USA under Catalogue No CRL 1992; TAP-deficient cell lines such as T2 can be used as APCs, and due to the lack of TAP nearly all peptides presented by MHC class I will be the peptides under scrutiny used for externally loading the empty MHC class I molecules of these cell lines, hence all effects will clearly attribute to the used peptides.

Preferably, the antigen presenting cells are dendritic cells. Suitably, the dendritic cells are autologous dendritic cells which are pulsed with an antigenic peptide. The antigenic peptide may be any suitable antigenic peptide which gives rise to an appropriate T-cell response. T-cell therapy using autologous dendritic cells pulsed with peptides from a tumor associated antigen is disclosed in Murphy et al (1996) The Prostate 29, 371-380, and Tjua et al (1997) The Prostate 32, 272-278.

Thus, in a preferred embodiment of the present invention the pharmaceutical composition containing at least one antigen presenting cell is pulsed or loaded with the peptide, for instance by the method of example 4.

As an alternative the antigen presenting cell comprises an expression construct encoding the peptide. The polynucleotide may be any suitable polynucleotide and it is preferred that it is capable of transducing the dendritic cell thus resulting in the presentation of a peptide and induction of immunity.

Conveniently, a nucleic acid of the invention may be comprised in a viral polynucleotide or virus. For example, adenovirus-transduced dendritic cells have been shown to induce antigen-specific antitumor immunity in relation to MUC1 (see Gong et al (1997) Gene Ther. 4, 1023-1028). Similarly, adenovirus-based systems may be used (see, for example, Wan et al (1997) Hum. Gene Ther. 8, 1355-1363); retroviral systems may be used (Specht et al (1997) J. Exp. Med. 186, 1213-1221 and Szabolcs et al (1997) Blood particle-mediated transfer to dendritic cells may also be used (Tuting et al (1997) Eur. J. Immunol. 27, 2702-2707); and RNA may also be used (Ashley et al (1997) J. Exp. Med. 186, 1177 1182).

Generally, a pharmaceutical composition of the invention containing (a) nucleic acid(s) of the invention can be administered in a similar manner as those containing peptide(s) of the invention, e.g. intravenously, intra-arterially, intra-peritoneally, intramuscularly, intradermally, intratumorally, orally, dermally, nasally, buccally, rectally, vaginally, by inhalation, or by topical administration.

Due to evasion mechanisms a tumor often develops resistance to the drug it is treated with. The drug resistance may occur during treatment and manifests itself in metastases and recurring tumors. To avoid such a drug resistance a tumor is commonly treated by a combination of drugs and metastases and tumors recurring after a disease free period of time often require a different combination. Therefore, in one aspect of the invention the pharmaceutical composition is administered in conjunction with a second anticancer agent. The second agent may be administered before after or simultaneously with the pharmaceutical composition of the invention. A simultaneous administration can e.g. be achieved by mixing the pharmaceutical composition of the invention with the second anticancer agent if chemical properties are compatible. Another way of a simultaneous administration is the administration of the composition and anticancer agent on the same day independently from the route of administration such that the pharmaceutical composition of the invention may be e.g. injected while the second anticancer agent is for instance given orally. The pharmaceutical composition and second anticancer agent may also be administered within the same treatment course but on different days and/or within separate treatment courses.

In another aspect the present invention provides a method for treating or preventing a cancer in a patient comprising administering to the patient a therapeutically effective amount any one of the pharmaceutical compositions of the invention.

A therapeutically effective amount will be an amount sufficient to induce an immune response, in particular an activation of a subpopulation of CTLs. A person skilled in the art may easily determine whether an amount is effective by using standard immunological methods, such as those provided in the examples of the present specifications. Another way of monitoring the effect of a certain amount of the pharmaceutical composition is to observe the growth of the tumor treated and/or its recurrence.

In a particularly preferred embodiment of the present invention the pharmaceutical composition is used as an anticancer vaccine.

The composition containing peptides or peptide-encoding nucleic acids can also constitute a tumor or cancer vaccine. It may be administered directly into the patient, into the affected organ or systemically, or applied ex vivo to cells derived from the patient or a human cell line which are subsequently administered to the patient, or used in vitro to select a subpopulation from immune cells derived from the patient, which are then re-administered to the patient.

The composition of the invention may be used in a method for treating of or used as a vaccine for cancer. The cancer may be of the buccal cavity and pharynx, cancer of the digestive tract, cancer of the colon, rectum, and anus, cancer of the respiratory tract, breast cancer, cancer of the cervix uteri, vagina, and vulva, cancer of the uterine corpus and ovary, cancer of the male genital tract, cancer of the urinary tract, cancer of the bone and soft tissue, and kaposi sarcoma, melanoma of the skin, eye melanoma, and non-melanoma eye cancer, cancer of the brain and central nervous system, cancer of the thyroid and other endocrine glands, Hodgkin Lymphoma, Non-Hodgkin Lymphoma, and myeloma, preferably renal cancer, colorectal cancer, lung cancer, breast cancer, pancreatic cancer, prostate cancer, gastric cancer, brain cancer, GIST or glioblastoma, preferably brain tumors and even more preferred glioblastomas.

In the most preferred embodiment of the method of treatment or vaccine according to the invention, the vaccine is a multiple peptide tumor vaccine for treatment of GBM. Preferably, the vaccine comprises a set of tumor-associated peptides selected from SEQ ID No. 1 to SEQ ID No. 12 which are located and have been identified on primary glioblastoma cells. This set includes HLA class I and class II peptides. The peptide set can also contain at least one peptide, such as from HBV core antigen, used as a positive control peptide serving as immune marker to test the efficiency of the intradermal administration. In one particular embodiment, the vaccine consists of 14 individual peptides (according to SEQ ID No. 1 to SEQ ID No. 12) with between about 1500 μg to about 75 μg, preferably between about 1000 μg to about 175 μg and more preferred between about 500 μg to about 600 μg, and most preferred about 578 μg of each peptide, all of which may be purified by HPLC and ion exchange chromatography and appear as a white to off-white powder. The lyophilisate is preferably dissolved in sodium hydrogen carbonate, and is used for intradermal injection within 30 min after reconstitution at room temperature. According to the present invention, preferred amounts of peptides can vary between about 0.1 and 100 mg, preferably between about 0.1 to 1 mg, and most preferred between about 300 μg to 800 μg per 500 μL of solution. Herein, the term "about" shall mean +/−10 percent of the given value, if not stated differently. The person of skill will be able to adjust the actual amount of peptide to be used based on several factors, such as, for example, the immune status of the individual patient and/or the amount of TUMAP that is presented in a particular type of cancer. The peptides of the present invention might be provided in other suitable forms (sterile solutions, etc.) instead of a lyophilisate.

The pharmaceutical compositions comprise the peptides either in the free form or in the form of a pharmaceutically acceptable salt.

As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment the pharmaceutical compositions comprise the peptides as salts of acetic acid (acetates), ammonium or hydrochloric acid (chlorides).

In another embodiment, a pharmaceutical composition of the present invention may include sugars, sugar alcohols, amino acids such as glycine, arginine, glutamic acid and others as framework former. The sugars may be mono-, di- or trisaccharide. These sugars may be used alone, as well as in combination with sugar alcohols. Examples of sugars include glucose, mannose, galactose, fructose or sorbose as monosaccharides, saccharose, lactose, maltose or trehalose as disaccharides and raffinose as a trisaccharide. A sugar alcohol may be, for example, mannitose. Preferred ingredients are saccharose, lactose, maltose, trehalose, mannitol and/or sorbitol, and more preferably, mannitol.

Furthermore pharmaceutical compositions of the present invention may include physiological well tolerated excipients (see Handbook of Pharmaceutical Excipients, 5th ed., edited by Raymond Rowe, Paul Sheskey and Sian Owen, Pharmaceutical Press (2006)), such as antioxidants like ascorbic acid or glutathione, preserving agents such as phenol, m-cresol, methyl- or propylparaben, chlorobutanol, thiomersal (thimerosal) or benzalkoniumchloride, stabilizer, framework former such as saccharose, lactose, maltose, trehalose, mannitose, mannitol and/or sorbitol, mannitol and/or lactose and solubilizer such as polyethyleneglycols (PEG), i.e. PEG 3000, 3350, 4000 or 6000, or cyclodextrins, i.e. hydroxypropyl-β-cyclodextrin, sulfobutylethyl-β-cyclodextrinor γ-cyclodextrin, or dextrans or poloxamers, i.e. poloxamer 407, poloxamer 188, or Tween 20, Tween 80. In a preferred embodiment pharmaceutical compositions of the present invention include one or more well tolerated excipients, selected from the group consisting of antioxidants, framework formers and stabilizers.

The acceptable pH-range is pH 2-12 for intravenous and intramuscular administration, but subcutaneously the range is reduced to 2.7-9.0 as the rate of in vivo dilution is reduced resulting in more potential for irradiation at the injection site. Strickley Robert G., Pharm. Res., 21, NO:2, 201-230 (2004).

The pharmaceutical preparation of the present invention comprising peptides, and/or nucleic acid(s) according to the invention is administered to a patient that suffers from an adenomatous or cancerous disease that is associated with the respective peptide or antigen. By this, a T cell-mediated immune response can be triggered.

Preferred is a pharmaceutical composition according to the invention, wherein the amount of (in particular tumor associated) peptide(s), of nucleic acid(s) according to the invention or expression vector(s) according to the invention as present in the composition is/are tissue, cancer, and/or patient-specific.

In another embodiment of the invention the vaccine is a nucleic acid vaccine. It is known that inoculation with a nucleic acid vaccine, such as a DNA vaccine, encoding a polypeptide leads to a T-cell response. It may be administered directly into the patient, into the affected organ or systemically, or applied ex vivo to cells derived from the patient or a human cell line which are subsequently administered to the patient, or used in vitro to select a subpopulation from immune cells derived from the patient, which are then re-administered to the patient. If the nucleic acid is administered to cells in vitro, it may be useful for the cells to be transfected so as to co-express immune-stimulating cytokines, such as interleukin-2 or GM-CSF. The nucleic acid(s) may be substantially pure, or combined with an immune-stimulating adjuvant, or used in combination with immune-stimulatory cytokines, or be administered with a suitable delivery system, for example liposomes. The nucleic acid vaccine may also be administered with an adjuvant such as those described for peptide vaccines above. It is preferred if the nucleic acid vaccine is administered without adjuvant.

The polynucleotide may be substantially pure, or contained in a suitable vector or delivery system. Suitable vectors and delivery systems include viral, such as systems based on adenovirus, vaccinia virus, retroviruses, herpes virus, adeno-associated virus or hybrids containing elements of more than one virus. Non-viral delivery systems include cationic lipids and cationic polymers as are well known in the art of DNA delivery. Physical delivery, such as via a "gene-gun", may also be used. The peptide or peptide encoded by the nucleic acid may be a fusion protein, for example with an epitope from tetanus toxoid which stimulates CD4-positive T-cells.

Suitably, any nucleic acid administered to the patient is sterile and pyrogen free. Naked DNA may be given intramuscularly or intradermally or subcutaneously. Conveniently, the nucleic acid vaccine may comprise any suitable nucleic acid delivery means. The nucleic acid, preferably DNA, may also be delivered in a liposome or as part of a viral vector delivery system. It is preferred if the nucleic acid vaccine, such as DNA vaccine, is administered into the muscle, whilst peptide vaccines are preferably administered s.c. or i.d. It is also preferred if the vaccine is administered into the skin.

It is believed that uptake of the nucleic acid and expression of the encoded polypeptide by professional antigen presenting cells such as dendritic cells may be the mechanism of priming of the immune response; however, dendritic cells may not be transfected but are still important since they may pick up expressed peptide from transfected cells in the tissue ("cross-priming", e.g., Thomas A M, Santarsiero L M, Lutz E R, Armstrong T D, Chen Y C, Huang L Q, Laheru D A, Goggins M, Hruban R H, Jaffee E M. Mesothelin-specific CD8(+) T cell responses provide evidence of in vivo cross-priming by antigen-presenting cells in vaccinated pancreatic cancer patients. J Exp Med. 2004 Aug. 2; 200(3):297-306).

Polynucleotide-mediated immunisation therapy of cancer is described in Conry et al (1996) Seminars in Oncology 23, 135-147; Condon et al (1996) Nature Medicine 2, 1122-1127; Gong et al (1997) Nature Medicine 3, 558-561; Zhai et al (1996) J. Immunol. 156, 700-710; Graham et al (1996) Int J. Cancer 65, 664-670; and Burchell et al (1996) 309-313 In: Breast Cancer, Advances in biology and therapeutics, Calvo et al (Eds), John Libbey Eurotext, all of which are incorporated herein by reference in their entireties.

It may also be useful to target the vaccine to specific cell populations, for example antigen presenting cells, either by the site of injection, use of targeting vectors and delivery systems, or selective purification of such a cell population from the patient and ex vivo administration of the peptide or nucleic acid (for example dendritic cells may be sorted as described in Zhou et al (1995) Blood 86, 3295-3301; Roth et al (1996) Scand. J. Immunology 43, 646-651). For example, targeting vectors may comprise a tissue- or tumor-specific promoter which directs expression of the antigen at a suitable place.

Finally, the vaccine according to the invention can be dependent from the specific type of cancer that the patient to be treated is suffering from as well as the status of the disease, earlier treatment regimens, the immune status of the patient, and, of course, the HLA-haplotype of the patient. Furthermore, the vaccine according to the invention can contain individualised components, according to personal needs of the particular patient. Examples are different amounts of peptides according to the expression of the related TAAs in the particular patient, unwanted side-effects due to personal allergies or other treatments, and adjustments for secondary treatments following a first round or scheme of treatment.

In addition to being useful for treating cancer, the peptides of the present invention are also useful as diagnostics. Since the peptides were generated from glioblastoma and since it was determined that these peptides are not present in normal tissues, these peptides can be used to diagnose the presence of a cancer.

The presence of the peptides of the present invention on tissue biopsies can assist a pathologist in diagnosis of cancer. Detection of certain peptides of the present invention by means of antibodies, mass spectrometry or other methods known in the art can tell the pathologist that the tissue is malignant or inflamed or generally diseased. Presence of groups of peptides of the present invention can enable classification or subclassification of diseased tissues.

The detection of the peptides of the present invention on diseased tissue specimen can enable the decision about the benefit of therapies involving the immune system, especially if T lymphocytes are known or expected to be involved in the mechanism of action. Loss of MHC expression is a well described mechanism by which infected of malignant cells escape immunosurveillance. Thus, presence of the peptides of the present invention shows that this mechanism is not exploited by the analyzed cells.

The peptides of the present invention might be used to analyze lymphocyte responses against those peptides of the present invention, such as T cell responses or antibody responses against the peptides of the present invention or the peptides of the present invention complexed to MHC molecules. These lymphocyte responses can be used as prognostic markers for decision on further therapy steps. These responses can also be used as surrogate markers in immunotherapy approaches aiming to induce lymphocyte responses by different means, e.g. vaccination of protein, nucleic acids, autologous materials, adoptive transfer of lymphocytes. In gene therapy settings, lymphocyte responses against the peptides of the present invention can be considered in the assessment of side effects. Monitoring of lymphocyte responses might also be a valuable tool for follow-up examinations of transplantation therapies, e.g. for the detection of graft versus host and host versus graft diseases.

In yet another aspect thereof, the present invention relates to a kit comprising (a) a container that contains a pharmaceutical composition as described above, in solution or in lyophilized form; (b) optionally, a second container containing a diluent or reconstituting solution for the lyophilized formulation; and (c) optionally, instructions for (i) use of the solution or (ii) reconstitution and/or use of the lyophilized formulation. The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contains instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, a anti-angiogenesis agent or inhibitor, a apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The pharmaceutical formulation of the present invention is one that is suitable for administration of the peptides by any acceptable route such as oral (enteral), nasal, ophthalmic, subcutaneous, intradermal, intramuscular, intravenous or transdermal. Preferably the administration is s.c., and most preferably, i.d. Administration may be by infusion pump.

It should be understood that the features of the invention as disclosed and described herein can be used not only in the respective combination as indicated but also in a singular fashion without departing from the intended scope of the present invention. For the purposes of the present invention, all references as cited herein are incorporated by reference in their entireties.

The invention will now be described in more detail by reference to the following Figures, the Sequence listing, and the Examples. The following examples are provided for illustrative purposes only and are not intended to limit the invention.

DESCRIPTION OF THE FIGURES

FIG. 1: Tetramer analysis of microsphere driven proliferation of CSP-001 and NLGN4X-001 specific CD8+ lymphocytes from peripheral blood of a healthy donor. 1×106 CD8+ enriched PBMCs per well were stimulated weekly with microspheres coupled to anti-CD28 plus high density tumor antigen A*0201/CSP-001 (left panel) or anti-CD28 plus high density tumor antigen A*0201/NLGN4X-001 (right panel). After three stimulations in vitro, all cells were stained with antibody CD8 FITC, and fluorescently-labeled tetramers A*0201/CSP-001 and A*0201/NLGN4X-001. Cells are gated on CD8+ lymphocytes; numbers represent percentage of cells in the indicated quadrant among CD8+ lymphocytes.

Figure 2:
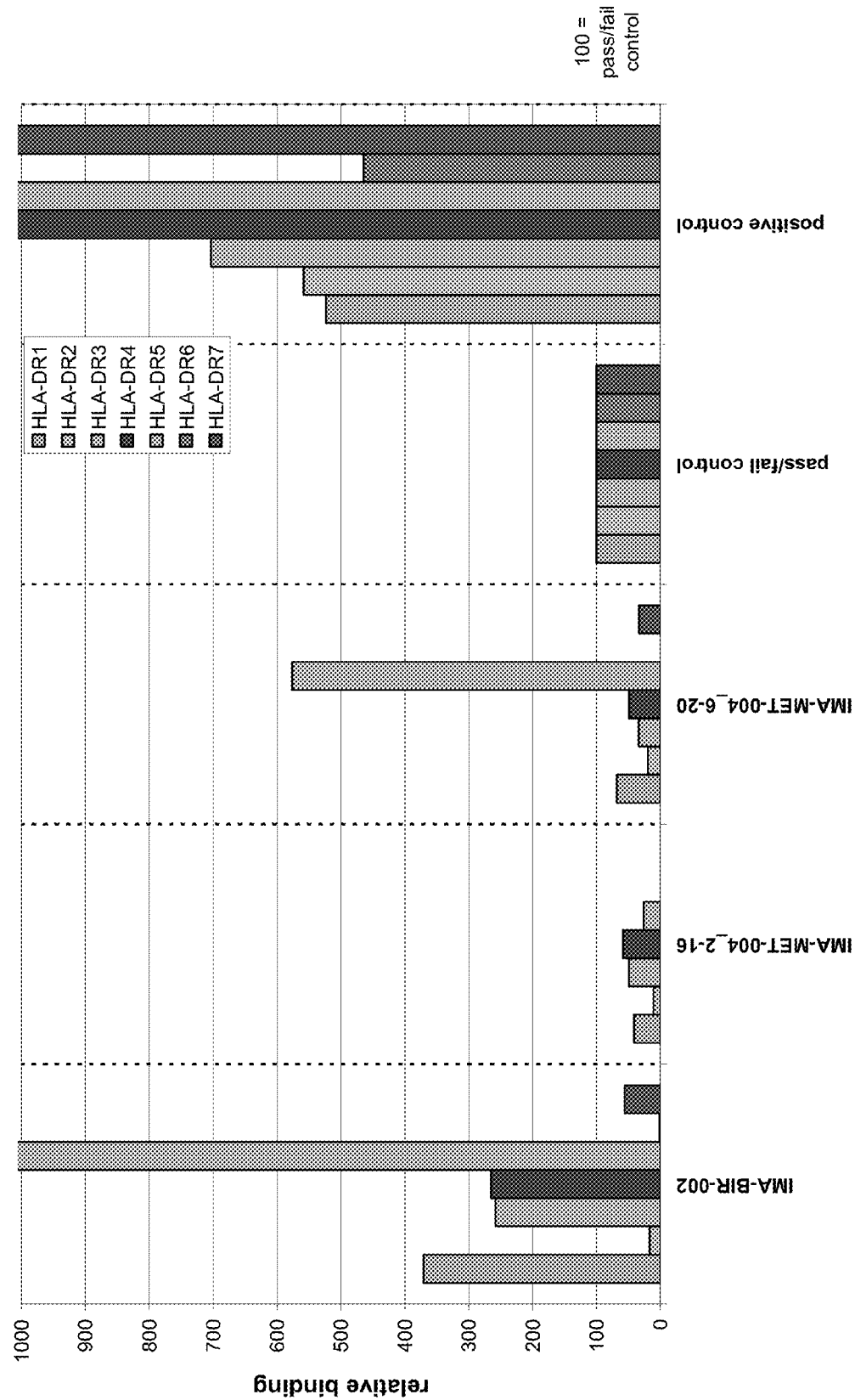

FIG. 2: Affinity of HLA class I peptides of the invention to the MHC molecule coded by the HLA-A*0201 allele. Dissociation constants (KD) of IMA950 HLA class I TUMAPs, control peptides IMA-MUC-001 (intermediate binder) and the viral marker peptide HBV-001 (strong binder) were measured by an ELISA-based MHC refolding assay. The assay was repeated three times with similar results.

Figure 3:
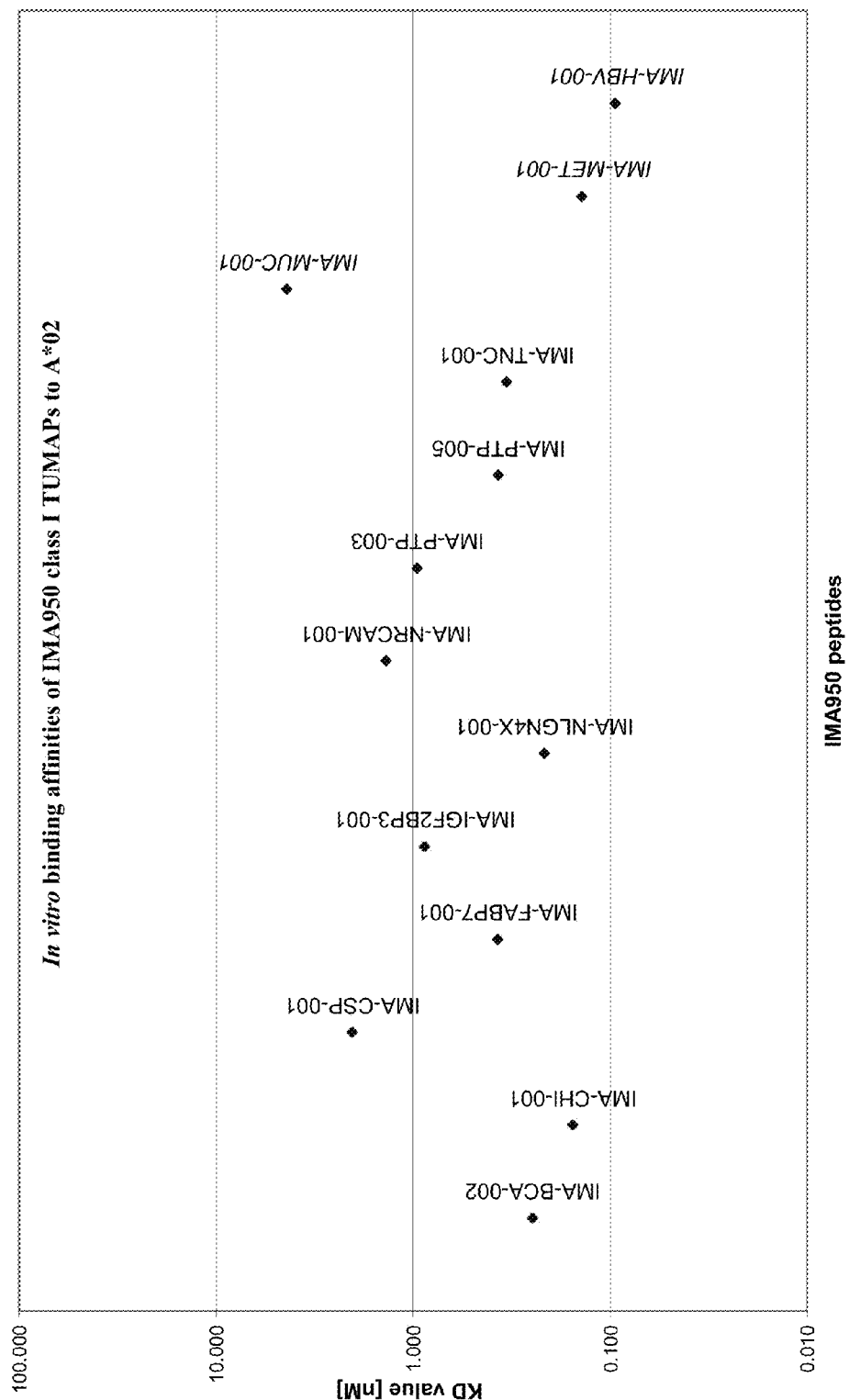

FIG. 3: Relative in vitro binding of IMA-BIR-002 and IMA-MET-005 derived 15-mers to the most frequent HLA-DR alleles. The ProImmune REVEAL™ technology employs in vitro HLA-DR assembly assays to determine the on-rates for the MHC:peptide complex as one major determinant of the binding constant of individual peptides. The assay was performed by ProImmune (Oxford, UK). At a fixed time point, the amount of intact MHC:peptide complexes is measured and compared with the amount for a pass/fail control (relative weak binder). A strong, promiscuous HLA-DR binder is included as positive control. Values indicate amount of binding for the individual peptides and HLA-DR molecules relative to the pass/fail control. As the REVEAL™ technology is limited to 15-mers, two overlapping 15-mers (position 2-16; 6-20) were tested instead of full-length MET-005.

Figure 4A:
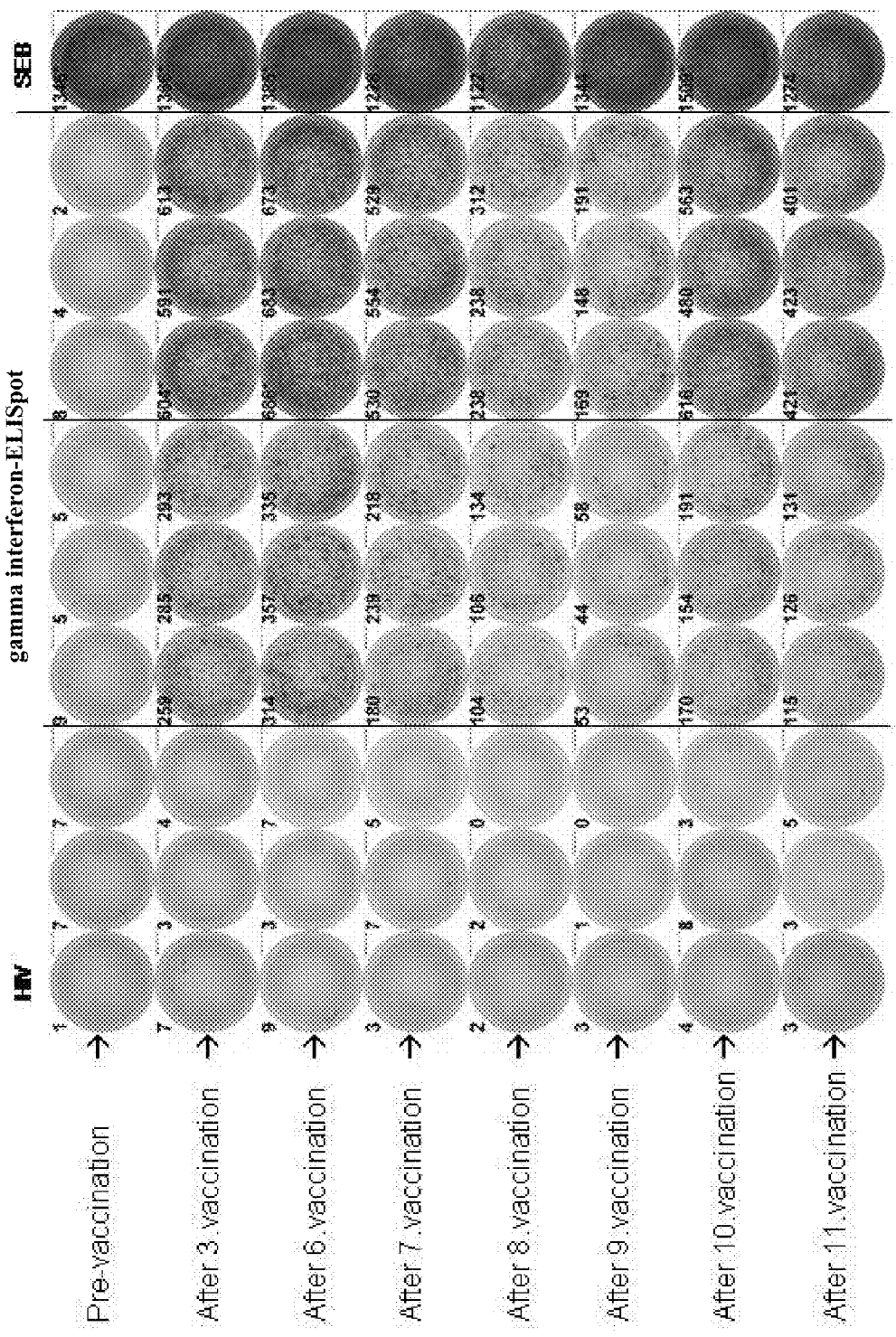
Figure 4B:
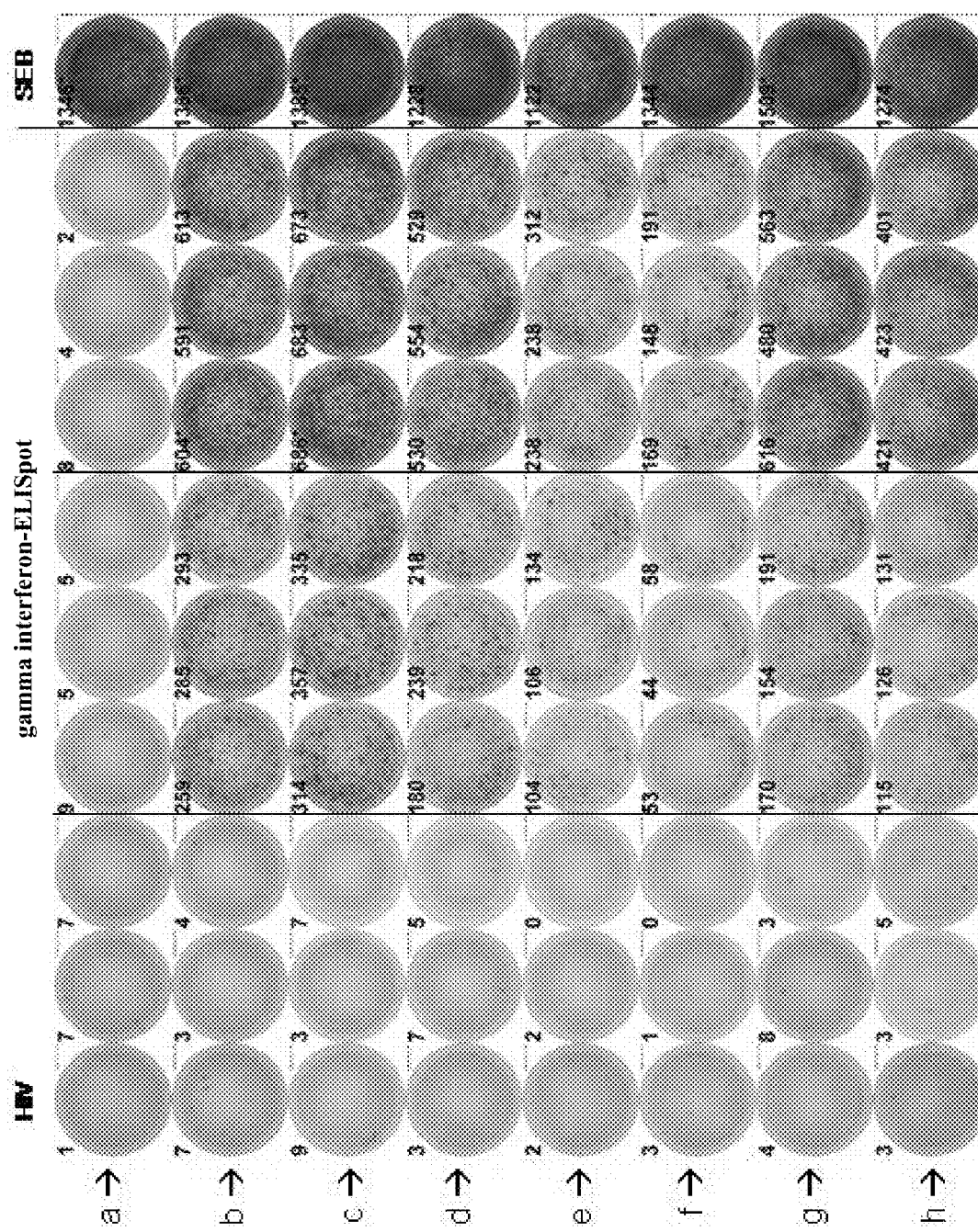

FIGS. 4a and 4b depict the presence of PSMA and Survivin-specific IFN-secreting CD4+ T-cells in peripheral blood mononuclear cells (PBMC) from different time points of a vaccinated patient which were determined using an IFN-EliSpot. Time points: pre-vaccination (a) and after 3.(b), 6.(c), 7.(d), 8.(e), 9.(f), 10.(g), 11.(h) vaccination.

Figure 5A:
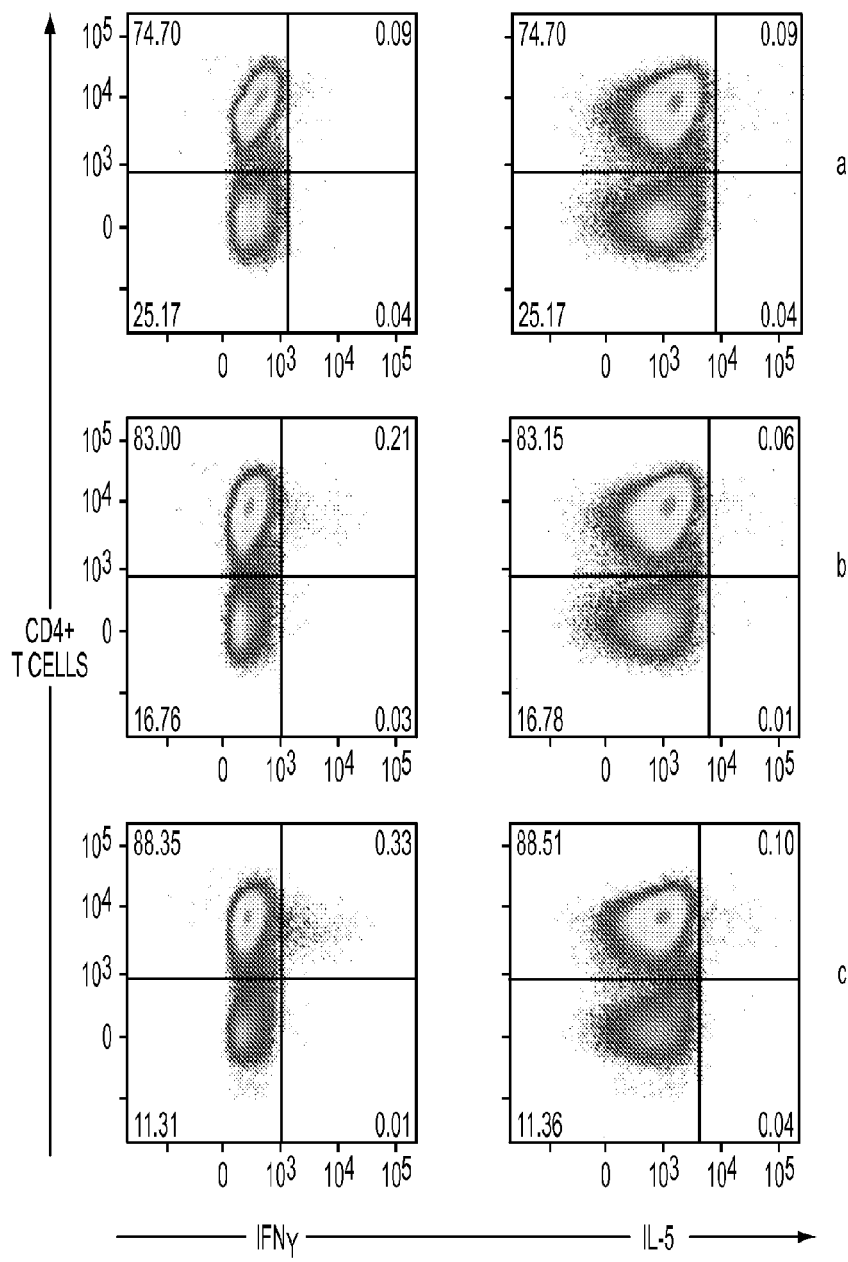
Figure 5B:
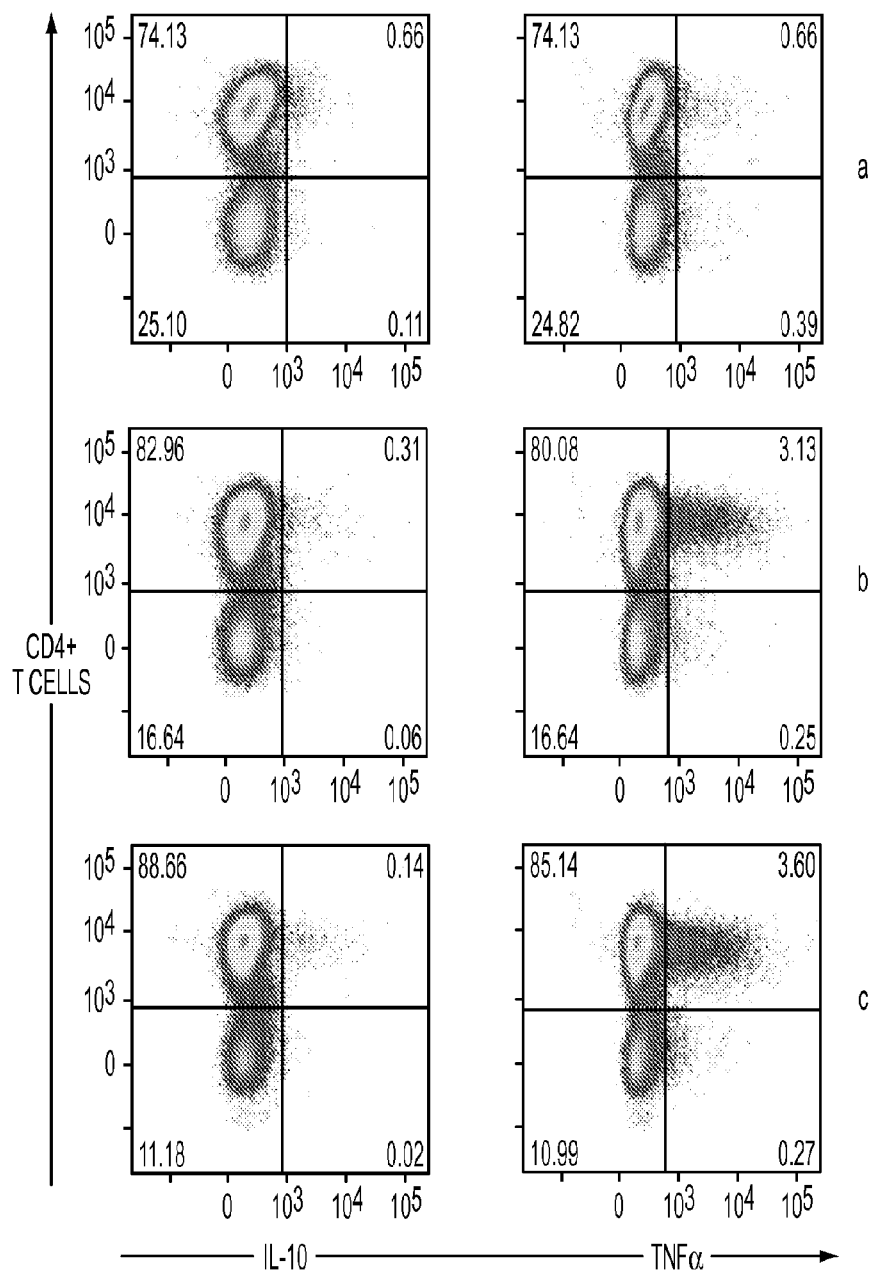

FIG. 5 shows the presence of Survivin-specific IFN-, IL-5, IL-10, TNFα-secreting CD4+ T-cells in PBMC from three different time points of a vaccinated patient which were determined via the Intracellular staining-Assay (ICS). Time points: after 1.(a), 3.(b), 7.(c), vaccinations.

EXAMPLES

1. Synthesis

Peptides were synthesized by standard and well-established solid phase synthesis using Fmoc chemistry. After purification by preparative HPLC, ion-exchange procedure was performed to incorporate physiologically compatible counter ions (for example acetate, ammonium or chloride). Finally, white to off white solids were obtained after lyophilisation. All TUMAPs are preferably administered as acetate salts, other salt-forms are also possible.

Importantly, identity and purity of the peptides can be determined easily and with high accuracy using mass spectrometry, amino acid analysis and analytical HPLC. According to analytical results, all peptides used for the IMA950 vaccine show the correct structure with purities ≥95%.

The peptides FTELTLGEF (HLA-A1; PolyPeptide Laboratories, Wolfenbüttel, Germany), LMLGEFLKL (HLA-A2; Clinalfa, Sissach, Switzerland), and EPDLAQCFY (HLA-B35; PolyPeptide Laboratories) were obtained in pharmaceutical quality.

TABLE 5

Physico-chemical characteristics of peptides in IMA950

| No. | Peptide ID | Peptide length (no of amino acids) | Salt form | Physical form | Hygro-scopicity |
|---|---|---|---|---|---|
| 1 | CSP-001 | 9 | acetate | White to off-white lyophilisate | Stored as freeze dried powder. Lyophilized peptides generally have hygroscopic properties. |
| 2 | FABP7-001 | 9 | acetate | | |
| 3 | NLGN4X-001 | 9 | acetate | | |
| 4 | TNC-001 | 9 | acetate | | |
| 5 | NRCAM-001 | 9 | acetate | | |
| 6 | IGF2BP3-001 | 9 | acetate | | |
| 7 | BCA-002 | 9 | acetate | | |
| 8 | MET-005 | 17 | acetate | | |
| 9 | PTP-003 | 9 | acetate/ammonium | | |
| 10 | PTP-005 | 9 | acetate | | |
| 11 | CHI-001 | 9 | acetate | | |
| 12 | BIR-002 | 15 | acetate | | |
| 13 | (HBV-001) | 10 | acetate | | |

2. Components of the Exemplary Pharmaceutical Composition IMA950

IMA950 is composed of a cocktail of synthetic tumor associated peptides (TUMAPs) of which the majority has been identified on primary colorectal cancer cells. The TUMAPs include 10 HLA class I-binding peptides with the capacity to activate cytotoxic T cells (CD8+ T cells), 1 HLA class II-binding peptide with the capacity to activate T helper cells (CD4+ T cells), and 1 elongated HLA class I-binding peptide with both capacities. T helper cells play a crucial role in assisting the function of cytotoxic T cells by releasing cytokines which enhance the killer function of CD8+ T cells and may also act directly against tumor cells (Knutson and Disis, 2005). In addition to these 12 TUMAPs IMA950 contains one viral control peptide.

Samples from surgically removed malignant and normal tissue from GBM patients and blood from healthy donors were analyzed in a stepwise approach:

First, genome-wide mRNA expression analysis by microarrays was used to identify genes overexpressed in the malignant tissue compared with a range of normal organs and tissues. In a second step, HLA ligands from the malignant material were identified by mass spectrometry. Subsequently identified HLA ligands were compared to gene expression data. Peptides encoded by selectively expressed or overexpressed genes as detected in step 1 were considered suitable candidate TUMAPs for a multi-peptide vaccine.

Finally, peripheral CD8+ T cells of healthy individuals were tested for reactivity against the tumor-associated HLA ligands using several immunoassays (in vitro T-cell assays).

TABLE 6

IMA950 TUMAP composition.
Exemplary IMA950 contains 10 HLA-A*02-binding peptides (class I), 1 HLA-DR-binding peptide (class II), and 1 elongated HLA-A*02 peptide. In addition, the viral marker peptide HBV-001 will be included which is not listed here.
Table 6: Functions of the proteins, the TUMAPs are derived from

| TUMAP ID | Name | Function/Comments |
|---|---|---|
| HLA-A*02 TUMAPs | | |
| BCA-002 | Brevican | Brain-specific ECM molecule involved in invasion; overexpressed and specifically deglycosylated in glioma; stem-cell niche associated. |
| CHI-001 | Chitinase 3-like 2 | Extracellular protein with unclear function; highly overexpressed in glioblastoma. |
| CSP-001 | Chondroitin sulfate proteoglycan 4 | Transmembrane proteoglycan, role in neovascularization; overexpressed by tumor cells and pericytes on blood vessels of malignant brain tumors. |
| FABP7-001 | Fatty acid binding protein 7, brain | Cytoplasmic protein involved in fatty acid metabolism; associated with increased motility of GBM cells into surrounding tissue and with short survival; highly overexpressed in GBM. |
| IGF2BP3-001 | Insulin-like growth factor 2 mRNA binding protein 3 | Function in mRNA turnover and translational control; oncofetal protein; described as overexpressed in several cancers where it is associated with poor survival. |
| NLGN4X-001 | Neuroligin 4, X-linked | Cell-adhesion molecule; few literature; highly immunogenic; high overexpression in GBM and GIST; role in invasion and tumorigenesis. |
| NRCAM-001 | Neuronal cell adhesion molecule | Involved in beta-catenin signaling pathway; major role in invasion, tumor growth and tumorigenesis; high expression levels are correlated to poor survival. |
| PTP-003 PTP-005 | Protein tyrosine phosphatase, receptor-type, Z polypeptide 1 | Type I transmembrane protein; highly overexpressed in glioblastoma, oligodendroglioma, and other tumors; functional role in tumorigenesis; gene amplification occurs frequently in GBM and other tumor entities. |
| TNC-001 | Tenascin C | Role in angiogenesis; key player in several pathways involved in tumor transformation and proliferation; overexpressed in tumor-supplying blood vessels; cancer stem-cell niche associated. |

TABLE 6-continued

IMA950 TUMAP composition.
Exemplary IMA950 contains 10 HLA-A*02-binding peptides (class I), 1 HLA-DR-binding peptide (class II), and 1 elongated HLA-A*02 peptide. In addition, the viral marker peptide HBV-001 will be included which is not listed here.
Table 6: Functions of the proteins, the TUMAPs are derived from

| TUMAP ID | Name | Function/Comments |
|---|---|---|
| HLA-DR TUMAP | | |
| BIR-002 | Survivin | Tumor survival antigen involved in regulation of apoptosis and proliferation; overexpression in gliomas and other tumor entities correlates with poor prognosis. |
| elongated HLA-A*02 TUMAP | | |
| MET-005 | Met proto-oncogene | Hepatocyte growth factor receptor; involved in malignant transformation, invasiveness and angiogenesis; reported as GBM stem-cell associated. |

3. Presentation of Tumor Associated Peptides (TUMAPs) Contained in IMA950 on Tumor Samples.

Tissue Samples

Patients' tumor tissues were provided by Hôpitaux Universitaires de Genève (Medical Oncology Laboratory of Tumor Immunology) and Neurochirurgische Universitäts-Klinik Heidelberg (Molekularbiologisches Labor). Written informed consents of all patients had been given before surgery. Tissues were shock-frozen in liquid nitrogen immediately after surgery and stored until isolation of TUMAPs at −80° C.

Isolation of HLA Peptides from Tissue Samples

HLA peptide pools from shock-frozen tissue samples were obtained by immune precipitation from solid tissues according to a slightly modified protocol (Falk, K. et al 1991; Seeger, F. H. et al. T 1999) using the HLA-A*02-specific antibody BB7.2 or the HLA-A, -B, -C-specific antibody W6/32, CNBr-activated sepharose, acid treatment, and ultrafiltration.

Detection of TUMAPs by ESI-Liquid Chromatography Mass Spectrometry (ESI-LCMS)

Method One:

The obtained HLA peptide pools were separated according to their hydrophobicity by reversed-phase chromatography (CapLC, Waters) and the eluting peptides were analyzed in a hybrid quadrupole orthogonal acceleration time of flight tandem mass spectrometer (Q-TOF Ultima, Waters) equipped with an ESI source. Peptide pools were loaded onto a C 18 pre-column for concentration and desalting. After loading, the pre-column was placed in line for separation by a fused-silica micro-capillary column (75 μm i.d.×250 mm) packed with 5 μm C18 reversed-phase material (Dionex). Solvent A was 4 mM ammonium acetate/water. Solvent B was 2 mM ammonium acetate in 80% acetonitrile/water. Both solvents were adjusted to pH 3.0 with formic acid. A binary gradient of 15% to 60% B within 90 minutes was performed, applying a flow rate of 5 μl/min reduced to approximately 200 nl/min by a split-system. A gold coated glass capillary (PicoTip, New Objective) was used for introduction into the micro-ESI source. The integration time for the TOF analyzer was 1.9 s with an interscan delay of 0.1 s. Subsequently, the peptide sequences were revealed by collisionally induced decay (CID) mass spectrometry (ESI-LCMS/MS). The identified TUMAP sequence was assured by comparison of the generated natural TUMAP fragmentation pattern with the fragmentation pattern of a synthetic sequence-identical reference peptide.

Method Two:

The HLA peptide pools as obtained were separated according to their hydrophobicity by reversed-phase chromatography (Acquity UPLC system, Waters) and the eluting peptides were analyzed in an LTQ-Orbitrap hybrid mass spectrometer (ThermoElectron) equipped with an ESI source. Peptide pools were loaded directly onto the analytical fused-silica micro-capillary column (75 μm i.d.×250 mm) packed with 1.7 μm C 18 reversed-phase material (Waters) applying a flow rate of 400 nL per minute. Subsequently, the peptides were separated using a two-step 180 minute-binary gradient from 10% to 33% B at flow rates of 300 nL per minute. The gradient was composed of Solvent A (0.1% formic acid in water) and solvent B (0.1% formic acid in acetonitrile). A gold coated glass capillary (PicoTip, New Objective) was used for introduction into the micro-ESI source. The LTQ-Orbitrap mass spectrometer was operated in the data-dependent mode using a TOPS strategy. In brief, a scan cycle was initiated with a full scan of high mass accuracy in the orbitrap (R=30.000), which was followed by MS/MS scans also in the orbitrap (R=7.500) on the 5 most abundant precursor ions with dynamic exclusion of previously selected ions. Tandem mass spectra were interpreted by SEQUEST and additional manual control. The identified TUMAP sequence was assured by comparison of the generated natural TUMAP fragmentation pattern with the fragmentation pattern of a synthetic sequence-identical reference peptide. FIGS. 1a and b show exemplary spectra obtained from tumor tissue for MHC class I associated TUMAPs.

Table 7 shows the results of an analysis of glioblastoma samples, most from primary GBM tumors. All HLA-A*02 TUMAPs were found on three or more of 18 analyzed sample and 5 of the TUMAPs were detected in more than 50% of analyzed GBM samples.

TABLE 7

Detection of class I TUMAPS in GBM samples

| GBM No | sample | Tumor stage (grade) | IMA-BCA-002 | IMA-CHI-001 | IMA-CSP-001 | IMA-FABP7-001 | IMA-IGF2BP3-001 | IMA-NLGN4X-001 | IMA-NRCAM-001 | IMA-PTP-003 | IMA-PTP-005 | IMA-TNC-001 |
|---|---|---|---|---|---|---|---|---|---|---|---|---|
| 1 | GB6010T | primary GBM (IV) | + | + | + | + | + | + | + | + | + | + |
| 2 | GB1023T | primary GBM (IV) | + | + | + | + | + | + | + | + | + | + |
| 3 | GB1021T | primary GBM (IV) | − | + | + | − | − | − | − | + | − | + |
| 4 | GB6003T# | primary GBM (IV) | − | + | + | − | − | − | − | + | − | + |
| 5 | GB1020T | primary GBM (IV) | − | + | + | − | − | − | + | + | − | + |
| 6 | GB6027T | primary GBM (IV) | + | + | + | − | − | + | − | + | + | + |
| 7 | GB1014T# | second. GBM (IV) | − | − | + | − | − | − | − | + | − | + |
| 8 | GB1012T | primary GBM (IV) | − | − | − | − | − | − | − | + | + | − |
| 9 | GB6019T | primary GBM (IV) | − | − | + | − | − | − | − | + | + | − |
| 10 | GB1002T | primary GBM (IV) | − | + | + | − | − | − | − | + | + | + |
| 11 | GB6024T | primary GBM (IV) | − | + | + | − | − | − | − | + | + | − |
| 12 | GB1006T | primary GBM (IV) | − | − | − | + | − | − | − | + | + | − |
| 13 | GB1004T | primary GBM (IV) | − | + | + | − | − | − | − | + | − | − |
| 14 | GB1008T | primary GBM (IV) | − | + | + | − | − | − | − | + | − | + |
| 15 | GB1011T | primary GBM (IV) | − | + | + | − | − | − | − | + | + | + |
| 16 | GB1005T | primary GBM (IV) | + | + | + | − | − | + | − | + | + | + |
| 17 | GB6015T | primary GBM (IV) | − | − | − | − | − | − | − | + | − | − |
| 18 | GB6016T | primary GBM (IV) | − | − | + | − | − | − | − | + | − | + |

Only tumor samples analyzed for class I ligands were included ("−" = IMA950 class I TUMAP not detected; "+" = IMA950 class I TUMAP detected)

4. In vitro Immunogenicity for IMA950 MHC Class I Presented Peptides

To get information regarding the immunogenicity of peptides included in IMA950, we performed investigations using a well established in vitro stimulation platform already described by (Walter, S, Herrgen, L, Schoor, O, Jung, G, Wernet, D, Buhring, H J, Rammensee, H G, and Stevanovic, S; 2003, Cutting edge: predetermined avidity of human CD8 T cells expanded on calibrated MHC/anti-CD28-coated microspheres, J. Immunol., 171, 4974-4978). This way we could show positive immunogenicity data for 10/10 tested HLA-A*0201 restricted peptides contained in IMA950 demonstrating that these peptides are T-cell epitopes against which CD8+ precursor T cells exist in humans. The immunogenicity of MET-005 could not be tested by this method as it does not bind in the elongated from to HLA-A*02. Therefore, tetramers with MET-005 could not be produced which are indispensable for the in vitro stimulation. However, for the included HLA-A*02 epitope MET-001 (YVDPVITSI, see EP 1507795B1) in vitro immunogenicity has been shown. MET-005 is supposed to stimulate MET-001 specific CTLs after appropriate and naturally occurring processing by APCs. Immunogenicity of MET-001 indicates the presence of MET-001 specific CTLs in healthy donors which is also a prerequisite for the effectiveness of MET-005 as part of a cancer vaccine. Therefore, immunogenicity of MET-001 is a strong indicator for the immunogenicity of MET-005.

In vitro Priming of CD8+ T Cells

To perform in vitro stimulations by artificial antigen presenting cells (aAPC) loaded with peptide-MHC complex (pMHC) and anti-CD28 antibody, first we isolated PBMCs (peripheral blood mononuclear cells) from fresh HLA-A*02+ buffy coats by using standard density gradient separation medium (PAA, Cölbe, Germany). Buffy coats were either obtained from the Blood Bank Tübingen or from the Katharinenhospital Stuttgart. Isolated PBMCs were incubated overnight in T-cell medium (TCM) for human in vitro priming consisting of RPMI-Glutamax (Invitrogen, Karlsruhe, Germany) supplemented with 10% heat inactivated human AB serum (PAA, Cölbe, Germany), 100 U/ml Penicillin/100 µg/ml Streptomycin (Cambrex, Verviers, Belgium), 1 mM sodium pyruvate (CC Pro, Neustadt, Germany) and 20 µg/ml Gentamycin (Cambrex). CD8+ lymphocytes were isolated using the CD8+ MACS positive selection kit (Miltenyi, Bergisch Gladbach, Germany) according to the manufacturer's instructions. Obtained CD8+ T-cells were incubated until use in TCM supplemented with 2.5 ng/ml IL-7 (PromoCell, Heidelberg, Germany) and 10 U/ml IL-2 (Chiron, Munich, Germany). Generation of pMHC/anti-CD28 coated beads, T-cell stimulations and readout was performed as described before (Walter et al., 2003) with minor modifications. Briefly, biotinylated recombinant HLA-A*0201 molecules lacking the transmembrane domain and biotinylated at the carboxy terminus of the heavy chain were produced following a method described by (Altman et al., 1996). The purified co-stimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.60 µm large streptavidin coated polystyrene particles (Bangs Laboratories, Illinois/USA). pMHC used as positive and negative controls were A*0201/MLA-001 (peptide ELA-GIGILTV from modified Melan-A/MART-1) and A*0201/DDX5-001 (YLLPAIVHI from DDX5) or A*0201/HBV-001 (FLPSDFFPSV), respectively.

800.000 beads/200 µl were coated in 96-well plates in the presence of 600 ng biotin anti-CD28 plus 200 ng relevant biotin-pMHC (high density beads) or 2 ng relevant plus 200 ng irrelevant (pMHC library) MHC (low density beads). Stimulations were initiated in 96-well plates by co-incubating 1×10⁶ CD8+ T cells with 2×10⁵ washed coated beads in 200 µl TCM supplemented with 5 ng/ml IL-12 (PromoCell) for 3-4 days at 37° C. Half of the medium was then exchanged by fresh TCM supplemented with 80 U/ml IL-2 and incubating was continued for 3-4 days at 37° C. This stimulation cycle was performed for a total of three times. Finally, tetrameric analyses were performed with fluorescent MHC tetramers (produced as described by (Altman et al., 1996) plus antibody CD8-FITC clone SK1 (BD, Heidelberg, Germany) on a four-color FACSCalibur (BD). Peptide specific cells were calculated as percentage of total CD8+ T cells. Evaluation of tetrameric analysis was done using the software FCS Express (De Novo Software). In vitro priming of specific tetramer+ CD8+ lymphocytes was detected by appropriate gating and by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific tetramer+ among CD8+ T-cells and the percentage of specific tetramer+ cells was at least 10× the median of the negative control stimulations).

In vitro Immunogenicity for IMA950 Peptides

For tested HLA class I peptides, in vitro immunogenicity could be demonstrated by generation of peptide specific T-cell lines. A representative staining showing generation of T-cell lines specific for is shown in FIG. 1. The results are summarized in table 8.

TABLE 8

Immunogenicity of HLA class I peptides included in IMA950

| Antigen | Positive donors/donors tested | Positive wells/wells tested |
| --- | --- | --- |
| BCA-002 | 75% | 35% |
| CHI-001 | 100% | 63% |
| CSP-001 | 100% | 57% |
| FABP7-001 | 100% | 27% |
| IGF2BP3-001 | 50% | 21% |
| NLGN4X-001 | 100% | 62% |
| NRCAM-001 | 86% | 39% |
| PTP-003 | 50% | 17% |
| PTP-005 | 100% | 52% |
| TNC-001 | 60% | 30% |
| MET-001 (MET-005) | 67% | 39% |
| HBV-001 | 43% | 12% |

Results of in vitro immunogenicity experiments conducted by immatics for all HLA class I peptides included in IMA950 are summarised here. Results shown have been obtained by stimulation of CD8+ cells with high density beads. As different human serum lots may highly affect the immunogenicity results, only assays in which one and the same serum lot was used, were evaluated together.

In addition to these results obtained from healthy blood donors, the peptides BCA-002, CHI-001, and NLGN4X-001 were also tested in a small number of glioblastoma patients. All peptides proved to be immunogenic to a similar extent compared with healthy donors, demonstrating the existence of precursor T cells in a relevant target population for the vaccine.

5. Immunogenicity of IMA950 Class II TUMAP BIR-002

A clinical study was conducted in order to confirm the immunogenicity of the peptide with the SEQ ID NO:12.

The primary study objective was the investigation of the PSA (prostate-specific antigen)-based response (PSA-R) to the subcutaneous administration of a prostate-specific peptide panel (vaccination therapy) in patients with biochemical relapse after radical prostatectomy without detection of manifest metastatic lesions.

The secondary study objective was the investigation of the tolerability and feasibility of administering vaccination therapy in patients with prostate carcinoma with special consideration of immunological phenomena in terms of a T cell response.

The study was designed as a prospective, randomized Phase I/II study for the indication of "biochemical relapse after radical prostatectomy without detection of manifest metastatic lesions."

Study Population

As part of this Phase I/II study, an attempt was made to induce PSA regression as an indicator of cessation of tumor growth by means of vaccination with a prostate-specific peptide panel in HLA-A*02$^+$ patients with biochemical relapse after radical prostatectomy. A combination of prostate-specific peptides was administered subcutaneously with evaluation of the extent of the respective immune response in the context of various administration forms of the antigenic structures.

In contrast to previous vaccination studies, the planned study targeted the treatment of patients with a small tumor burden not yet detectable by imaging procedures. The patients were all immunized in the same way using known prostate-specific antigenic structures to enhance the immune response to the malignantly transformed cells. Nineteen patients were treated.

TABLE 9

Characteristics of study population

|  | Total | % | Median | Range |
| --- | --- | --- | --- | --- |
| Age | 19 |  | 63 | 55-77 |
| Prior neo-/adjuvant treatment |  |  |  |  |
| None | 11 | 58 |  |  |
| Radiation | 3 | 16 |  |  |
| Intermittent Hormonal Therapy | 2 | 11 |  |  |
| Rad. + Int. Horm. Therapy | 2 | 11 |  |  |
| Rad. + Chemotherapy | 1 | 5 |  |  |
| TNM at RPX |  |  |  |  |
| T2a-c R0 | 6 | 32 |  |  |
| T3a-c R0 | 6 | 32 |  |  |
| T2a-c R1 | 3 | 16 |  |  |
| T3a-c R1 | 3 | 16 |  |  |
| T3aN2 R0 | 1 | 5 |  |  |
| Gleason score |  |  |  |  |
| 5-7 | 10 | 53 |  |  |
| 8-10 | 3 | 16 |  |  |
| unknown | 6 | 32 |  |  |
| RPX prior to vaccination in months |  |  | 41 | 9-124 |
| First relapse post OP in months |  |  | 14 | 1-90 |
| PSA at vaccination start |  |  | 0.76 | 0.14-10.8 |

Treatment Plan

After rule-out of manifest metastatic lesions using computed tomography and skeletal scintigraphy, the prostate-specific peptide vaccine was subcutaneously administered according to the different administration forms to patients with detected PSA relapse after prior radical prostatectomy (PSA increase in terms of a 50% elevated value during two measurements at least 14 days apart). The vaccine was administered 8× on days 0, 7, 14, 28, 42, and 56 (approximately 100 micrograms per peptide and injection each time). After each vaccination treatment and again on day 70, PSA was measured to evaluate the therapeutic response.

If a tumor response (complete remission [PSA-CR], partial remission [PSA-PR], or stable clinical course [no change, PSA-NC]) is detected, the patient received the vaccine once a month as maintenance therapy according to the selected administration form. The patient's response to vaccination therapy was evaluated in detail as follows:

Complete remission (PSA-CR): Normalization of an initially elevated PSA level, confirmed by measurement after an interval of at least 4 weeks. Normalization is defined as a PSA nadir of <0.2 ng/ml, which would be expected after radical prostatectomy with complete tumor or prostate extirpation.

Partial remission: a) PSA-PR ≤80% (Reduction in an initially elevated PSA level by 80%, confirmed by measurement after an interval of at least 4 weeks); and b) PSA-PR ≤50% (Reduction in an initially elevated PSA level by 50%, confirmed by measurement after an interval of at least 4 weeks.)

Stable disease (PSA-SD): No significant change over a period of at least four weeks. This includes stabilization and a reduction of less than 50% and an increase of less than 10%, confirmed by measurement after an interval of at least 4 weeks.

Progression (PSA-PD): Increase in the PSA level by more than 10%. In the event of PSA progression, the study was terminated.

After enrollment of the patients into the study, the epitope-specific vaccine was used (; the proteins specifically expressed in prostatic epithelial cells (e.g., PSMA/PSCA) were taken into account. In addition to investigating the general efficacy of the administered vaccine with respect to monitoring the growth of residual tumor fractions as evaluated by PSA monitoring, this study investigated the effects of various vaccination methods with respect to efficient modulation of the immune system. In addition to simple subcutaneous administration of the peptides alone, various combinations with adjuvants were also used. In particular, depot and adjuvant activity for peptide vaccines of Montanide (a formulation of the classical incomplete Freund's adjuvant suitable for use in humans), which has recently been described very favorably, was used. For this purpose, 500 μl of the peptide solution was mixed with 500 μl of Montanide and administered. Thereby, a water-in-oil emulsion is built that slowly releases the antigen contained in the aqueous phase over weeks. The physical stability of the emulsion is very high, as at 4° C. it can be stored for more than 3 months without significant phase separation. The depot function of Montanide has been exploited in several vaccination trials with good results (Oka et al., 2004).

One study arm investigated the efficacy of vaccination during concomitant stimulation of the immune system by growth factors, GM-CSF, Leukine® solution for injection. GM-CSF is a very commonly used adjuvant in peptide vaccination trials with several thereof reporting enhanced clinical and T-cell responses. Initially, GM-CSF is a dendritic cell recruitment and differentiation factor that is thought to enhance the number of dendritic cell at the vaccines' injection site. Although GM-CSF does not by itself activate antigen presenting cells as dendritic cells and macrophages an indirect activation in vivo has been reported (Molenkamp et al., 2005).

Another study arm investigated the efficacy of vaccination during concomitant activation of dendritic cells by epicutaneous use of imiquimod. Imiquimod was administered as an 5% ointment (Aldara). It has a strong immunostimulatory via its effect on TLR7 positive cells (e.g. plasmacytoid DCs, Langerhans cells, dermal DCs), activates the MyD88-dependent pathway. Activated APCs release T-cell stimulating and inflammatory cytokines, upregulate co-stimulation and migrate to draining lymph nodes. The potential of imiquimod to enhance peptide-induced CTL response by mixing the antigens into the ointment or by application of Aldara over the s.c. or i.d. injection site for the antigens has been demonstrated in animal models.

Another study arm investigated the efficacy of vaccination during concomitant activation of dendritic cells by mixing them with protamine-stabilized mRNA encoding mucin-1 to activate TLR 7/8. mRNA shows a broad activation of mouse and human immune cell populations. The presence of the poly-basic protein protamine in the formulation increases the half-life of the mRNA and induces the formation of potentially depot-forming particles. This adjuvant may therefore combine depot-forming and APC-activating properties.

In summary, the administration forms of the vaccine included the following approaches:

Subcutaneous administration of the peptide vaccine emulsified in Montanide

Subcutaneous administration of the peptide vaccine emulsified in 500 μl of Montanide in combination with topical administration of 225 μl of GM-CSF with the objective of achieving a stronger immune response triggered by concomitant administration of growth factors Subcutaneous administration of the peptide vaccine emulsified in 500 μl of Montanide in combination with local hyperthermia, the latter given with the objective of achieving a thermally induced stronger immune response Subcutaneous administration of the peptide vaccine emulsified in 500 μl of Montanide in combination with epicutaneous imiquimod in order to activate dendritic cells via TLR 7

Subcutaneous administration of the peptide vaccine emulsified in 500 μl of Montanide together with 55 μl of mucin-1 mRNA/protamine in order to activate dendritic cells via TLR 7/8

Schedule: The Entire Duration of the Study was 3 Years.

Prostate-specific peptide vaccines were administered to patients on days 0, 7, 14, 28, 42, and 56. In patients with stable disease or an objective tumor response (PSA-CR or PSA-PR), the vaccinations was received once a month i.d. until detectable progression occurs. On the basis of the experience available thus far, peptide injections are tolerated without significant adverse reactions. Because the response to vaccination therapy was evaluated solely serologically on the basis of the PSA measurement, a test was performed at the start of the study to determine whether the administered vaccine interferes with PSA measurement in vitro, which could simulate a clinical response. On days 0, 7, 14, 28, 42, 56, and 70, blood samples was taken for laboratory tests, PSA levels, differential blood count, FACS analysis, and cytokines. If treatment is continued past Day 70, 6-week PSA monitoring was performed in order to detect treatment failure in a timely manner.

Treatment was ended if documented progression of the disease occurred in terms of a continuous PSA elevation.

Beginning on day 84, immunization therapy was continued at 4-week intervals until documented progression or up to day 420 (15 months). Decisions regarding continuation of therapy (in successful cases) outside of this study were made on a case-by-case basis. Unexpected adverse reactions did not occur in this study.

The laboratory tests included coagulation, electrolytes, LDH, β2-M, CK, hepatic enzymes, bilirubin, creatinine, uric acid, total protein, coagulation, CRP, differential blood count with smear, PSA level, cytokines, FACS, Elispot.

Analysis of the cutaneous reaction to defined bacterial and fungal antigens (48-72 hours after administration, delayed type hypersensitivity (DTH), T cell-mediated, will serve as an analysis of the patient's cellular immune system before the start of the study).

The peptides required for the study (nona-peptides) was manufactured in the laboratory of PD Dr. Stefan Stevanovic in the department of Prof. H.-G. Rammensee. These peptides was purified by HPLC and analyzed by mass spectrometry. The purity of the peptides can also be checked by HPLC, mass spectrometry, and Edman sequencing. Using these methods, purity of up to 98% can be documented (which must be regarded as the maximum according to the current state of the methods). The synthesized peptides was dissolved in DMSO (CryoSure, WAK Chemie Medical GmbH; 10 mg/ml), diluted to 1:10 in Ampuwa (Fresenius Kabi), and aliquoted under sterile conditions.

Clinical Response

In two patients PET-CT scan could reveal local recurrence after local tumor was detected by continuous digital rectal examination. In the remaining 17 patients the location of disease activity could not be verified at study termination.

Repeated laboratory evaluation of differential blood count or extensive clinical chemistry did not reveal any abnormalities or changes during the study.

Of the 19 patients 16 patients reacted to the Survivin II peptide (IFN-g ELISPOT, +/−ICS) according to SEQ ID NO:12. Among them, were 12 patients with induction of an anti-survivin T-cell response upon vaccination, 2 with pre existing anti-Survivin T cells and 2 patients of whom it was not determined, whether pre existing anti-Survivin T cells were abundant.

Biochemical Response

Complete response was considered as a non-detectable PSA value according to the lowest value detectable of the laboratory collaborating after initially elevated PSA. The measurement had to be confirmed after an interval of at least four weeks. A PR >80% and >50% had to be reevaluated after four weeks accordingly. A PSA within the range of less than 50% decrease or less than 10% increase reflected stable disease if at least confirmed after four weeks. Progressive disease was considered any increase of more than 10% of PSA at treatment start.

Biochemical response in patients who terminated the study was followed until they received further treatment with local radiation or antihormonal therapy.

19 patients consented to participate and the data was analyzed with the longest follow-up lasting about 3.75 years.

PSA Stability and DT Increase

PSA values of two patients (10.2%) exhibited stability according to the above mentioned criteria of biochemical response which state that no rise of the PSA value greater than 10% at treatment start had occurred at study end (FIG. 6, Tables 10, 11, and 12). Follow up in those two cases was conducted 14 and 16 months after the last vaccine application. Average duration of stability was 24 months (28 and 31) at data cut-off with an average of 18 vaccinations (14 and 20) applied.

Out of these two patients, one patient showed partial response >50% for a period of 9 months, followed by a period of slow PSA rise with a doubling time of 20.5 compared to 9.8 months prior vaccination. Initial PSA relapse started 18 months post surgery for a pT2pN0 Gleason 5 tumor.

At data analysis Patient 8 exhibited stable disease since the beginning of the vaccination program 28 months ago. He had stopped treatment due to an allergic reaction after 10 months and the 14th vaccination. He had an unfavorable pT3b Gleason 3+4 situation with a PSA nadir after radical prostatectomy not below 0.6 ng/ml and PSA progression without timely delay after initial decline postoperatively. Doubling time slowed from 6.6 months to 148 months.

These two patients received dermal Imiquimod at the application site at each peptide vaccination.

PSA DT Increase without PSA Stability

PSA DT of Patient 11 was increased from 1.5 to 10.1 months during six month on study. Since he started with a PSA of 10.8 ng/ml and progressed to 17.8 ng/ml he terminated study procedures to receive antiandrogen monotherapy without any malignant lesions visualized in PET-CT. He received Aldara as adjuvant.

Patient 16 started into vaccine treatment plus Mucin-1-mRNA/protamine with a doubling time of 6.1 months. PSA velocity declined into a half life time of 2.7 months for five months followed by a statistically calculated rise of PSA DT of 14.4 months which is continuing 16 months after treatment start. With an initial PSA of 0.29 ng/ml, he dropped to 0.19 ng/ml during the first 5 months on study treatment, rose to 0.4 ng/ml within the following 8 months and terminated the study per protocol with 0.41 ng/ml 19 months after treatment start.

PSA Progression

Patient 5 progressed during the study according to the estimated PSA doubling time before vaccination. However, he experienced a PSA decline with a half-time life of 20.2 months after treatment end for a continuing period of 10 months at data cut-off. He still was not receiving any secondary treatment after vaccination end. He was vaccinated with montanide as the only adjuvant.

TABLE 10

PSA Doubling Time in months

| | Total | % | Geometric Mean | Range of DT |
|---|---|---|---|---|
| PSA DT prior vaccination in months | 19 | | 8.3 | 1.5-44.8 |
| PSA DT at study end or at end of follow-up | 18* | | 11.2 | 2.2-148 |
| No change of PSA DT during vaccination | 11 | 58 | | 2.2-44.8 |
| Increased PSA DT continuing at end of study | 4 | 21 | | |
| No change of PSA DT during vacc but decline after | 1 | 5 | | |
| Interim PSA decline or DT increase followed by DT decrease | 3 | 16 | | |

*PSA DT at study end or end of follow-up was not included for Pat. 5 due to PSA decline 7. Binding of HLA Class I-restricted Peptides of the Invention to HLA-A*0201

Objective and Summary

The objective of this analysis was to evaluate the affinity of the HLA class I peptides to the MHC molecule coded by the HLA-A*0201 allele as this is an important parameter for the mode of action of IMA950. Affinities to HLA-A*0201 were medium to high for all 10 HLA class I-restricted peptide in IMA950 and MET-001, dissociations constants (1(D) being in the range from 0.14 (MET-001) to 2.05 nM (CSP-001). All values are in the range between 0.1 for the strong binder HBV-001 and 4.4 for the intermediate binder MUC-001. These results confirmed the strong binding affinity of all HLA class I peptides of the IMA950 vaccine candidate and the MET-005 derived MET-001 to HLA-A*02.

Principle of Test

Stable HLA/peptide complexes consist of three molecules: HLA heavy chain, beta-2 microglobulin (b2m) and the peptidic ligand. The activity of denatured recombinant HLA-A*0201 heavy chain molecules alone can be preserved making them functional equivalents of "empty HLA-A*0201 molecules". When diluted into aqueous buffer containing b2m and an appropriate peptide, these molecules fold rapidly and efficiently in an entirely peptide-dependent manner. The availability of these molecules is used in an ELISA-based assay to measure the affinity of interaction between peptide and HLA class I molecule (Sylvester-Hvid et al., 2002).

Purified recombinant HLA-A*0201 molecules were incubated together with b2m and graded doses of the peptide of interest. Instead of full-length MET-005 that does not possess HLA class I binding capacities, the proven A*0-binding product MET-001 was included into the analysis that is generated in vivo from MET-005 by naturally occurring antigen processing. The amount of de novo-folded HLA/peptide complexes was determined by a quantitative ELISA. Dissociation constants (KD values) were calculated using a standard curve recorded from dilutions of a calibrant HLA/peptide complex.
Results Results are shown in FIG. 2. A lower KD value reflects higher affinity to HLA-A*0201. Most of the IMA950 peptides had similar and strong affinities to HLA-A*0201 within the range from 0.1 (HBV-001, strong binder) to 44.4 nM (MUC-001, intermediate binder). Thereby, all IMA950 class I TUMAPs have a medium to strong binding affinity to the MHC molecule A*02.

8. Binding of HLA Class II-restricted Peptides of the Invention to HLA-DR

Objective and Summary

Class II TUMAPs activate helper T cells which play a crucial role in assisting the function of CTLs triggered by class I-restricted TUMAPs. Binding of the IMA950 class II peptides to several different HLA class II molecules (promiscuous binding) is important to ensure that the majority of patients treated with the vaccine candidate IMA950 are able to benefit from a supportive helper T cell response. HLA-DR for example, the most dominantly expressed human HLA class II molecule, is highly polymorphic with several hundreds of known alleles. Based on known allele frequencies for HLA-DRB1 haplotypes and well-established binding algorithms, it can be predicted that both HLA class II ligands in IMA950—IMA-BIR-002 and IMA-MET-005—are promiscuous HLA-DR binding peptides. In detail, the probability that an HLA-A*02-positive Caucasian expresses at least one suitable HLA-DR allele is >90% for both IMA950 class II TUMAPs. As the remaining human class II alleles HLA-DQ and -DP were omitted from this calculation due to the lack of frequency data or binding prediction algorithms, the real promiscuity is most likely even higher. The calculated promiscuity of the two IMA950 class II TUMAPs is in the same range as for the known pan-DR epitope (PADRE, genotypic frequency $F_{projected}$=93.1%). In addition, the promiscuous binding of these peptides was confirmed experimentally by in vitro binding assays. Moreover, for IMA-BIR-002 a high in vivo immunogenicity could be demonstrated (see above). Summarizing, these results confirm that MET-005 and BIR-002 are promiscuous HLA-DR binding peptides.

Principle of Binding Prediction

Using the SYFPEITHI algorithm developed at the University of Tübingen (Rammensee et al., 1997; Rammensee et al., 1999), binding of IMA950 class II TUMAPs to several common HLA-DR alleles was ranked. The algorithm has already been successfully used to identify class I and class II epitopes from a wide range of antigens, e.g. from the human tumor-associated antigens TRP2 (class I) (Sun et al., 2000) and SSX2 (class II) (Neumann et al., 2004). The threshold for binding was defined at a score of 18 based on the analysis of binding scores of known published promiscuous HLA-DR ligands.

Published HLA-DR haplotype frequencies among the HLA-A*02 positive Caucasian population (Mori et al., 1997) and frequencies of high-resolution haplotypes (Chanock et al., 2004) were used (see Table 2). The haplotype frequency is the frequency of a distinct allele on an individual chromosome. Due to the diploid set of chromosomes within mammalian cells, the frequency of genotypic occurrence of this allele is higher and can be calculated employing the Hardy-Weinberg principle (haplotype frequency $G_f$ results in a genotypic occurrence F ($F=2G_f-G_f^2$]).

The sum of frequency of DRB1-haplotypes with known SYFPEITHI matrix and known individual frequency among the A*02+ Caucasian population is 47.8%. Therefore, the predicted binding distribution of class II TUMAPs to these alleles was projected to the remaining 52.2% of DRB1-alleles for which these data are not available.

Finally, promiscuous binding is defined as binding of a peptide to several HLA-DR alleles with the probability that one of these is expressed in the Caucasian population being at least 50%.

Principle of In vitro Binding Assay (ProImmune REVEAL™)

IMA-BIR-002 and IMA-MET-005 were assembled with HLA-DR broad antigens (HLA-DR1 to DR7, which comprise also the split antigens HLA-DR11 to -DR15 (Mori et al., 1997)) and analyzed using the REVEAL™ MHC:peptide binding assay (ProImmune, Oxford, UK) to determine their level of incorporation into MHC molecules. In this assay, binding was compared to that of a pass/fail control binder, and to a positive control peptide for each HLA-DR antigen.

Results

Based on the prediction by the SYFPEITHI algorithm IMA-BIR-002 and IMA-MET-005 are likely to bind to 7/8 respectively 8/8 of HLA-DR alleles with known binding motif (Table 11). The probability that an HLA-A*02 positive Caucasian expresses at least one suitable HLA-DRB1 allele for IMA-BIR-002 or IMA-MET-005 is 92.6% and near 100%, respectively. Therefore, both IMA950 class II peptides are predicted to be promiscuous HLA-DR binders.

If the haplotype frequency of binding HLA-DRB1 alleles was overestimated through this approach by factor two, their genotypic occurrence would still be >50% for all class II TUMAPs in IMA950. In addition, experimental confirmation for promiscuous binding of IMA-BIR-002 to HLA-DR1, 3, 4 and 11 was obtained from in vitro binding data (FIG. 3). For IMA-MET-005 in vitro binding data of two overlapping 15-mers covering the complete sequence suggest a binding to HLA-DR11; however, the ProImmune REVEAL™ is intended as rough screening tool for the identification of potential HLA class II epitopes. Good HLA-DR binders with slow on-rates are potentially reported false negatively as non-binders by this assay. Thus, non-promiscuity of the HLA-DR binding of IMA-MET-005 in vivo can not be deduced from negative in vitro ProImmune REVEAL™ data. Thus, a promiscuous HLA-DR binding of IMA-MET-005 in an IMA950 based vaccination is well possible. As there are no sufficient data of binding properties and frequency for the remaining class II loci, HLA-DQ and -DP, these molecules have been omitted from calculation. Nevertheless, these molecules are further binding opportunities for the IMA950 class II TUMAPs.

As IMA-BIR-002 has proven broad immunogenicity in a clinical trial in prostate cancer patients with different HLA-DR alleles, the promiscuity of this class II peptide has clearly been proven in vivo.

In conclusion, in silico analysis of the HLA-DR binding properties of the two class II peptides contained in IMA950 and additional experimental evidence from in vitro assays and from a clinical trial with BIR-002 strongly suggest that these TUMAPs are promiscuous binders of human class II HLA molecules.

TABLE 11

Binding scores of IMA950 class II TUMAPs to HLA-DR alleles with known binding motif. Shown are the SYFPEITHI binding scores for the most common HLA-DRB1 alleles in the Caucasian population. p gives the haplotype frequencies among HLA-A*02 positive Caucasians. The peptide was considered as binding to an HLA molecule if the score was equal to or higher than 18. Accumulation of the p values for binding DRB1 alleles results in the minimal haplotype frequency $p_{min}$. Extrapolation of these frequencies to all DRB1 alleles including those with incomplete binding prediction matrix or frequency data gives the projected haplotype frequency $p_{projected}$ that corresponds to the frequency of genotypic occurrence $F_{projected}$.

| DRB1* allele | 0101 | 0301 | 0401 | 0404 | 0701 | 1101 | 1104 | 1501 |
|---|---|---|---|---|---|---|---|---|
| IMA-BIR-002 | | | | | | | | |
| SYFPEITHI score | 28 | 29 | 28 | 24 | 14 | 32 | 24 | 30 |
| p | 6.6% | 5.9% | 9.6% | 6.0% | 13.0% | 4.4% | 2.3% | n.d. |
| predicted binding | yes | yes | yes | yes | no | yes | yes | yes |
| $p_{min}$ | | | | | | | | 34.8% |
| Haplotypic frequency $p_{projected}$ | | | | | | | | 72.8% |
| Genotypic frequency $F_{projected}$ | | | | | | | | 92.6% |
| IMA-MET-005 | | | | | | | | |
| SYFPEITHI score | 28 | 20 | 26 | 26 | 28 | 20 | 22 | 22 |
| p | 6.6% | 5.9% | 9.6% | 6.0% | 13.0% | 4.4% | 2.3% | n.d. |
| predicted binding | yes | yes | yes | yes | yes | yes | yes | yes |
| $p_{min}$ | | | | | | | | 47.8% |
| Haplotypic frequency $p_{projected}$ | | | | | | | | 100.0% |
| Genotypic frequency $F_{projected}$ | | | | | | | | 100.0% | n.d. = no data

REFERENCE LIST

Aitkenhead M, Wang S J, Nakatsu M N, Mestas J, Heard C, Hughes C C (2002). Identification of endothelial cell genes expressed in an in vitro model of angiogenesis: induction of ESM-1, (beta)ig-h3, and NrCAM. Microvasc. Res. 63, 159-171.

Al-Joudi F S, Iskandar Z A, Imran A K (2007). Survivin expression correlates with unfavourable prognoses in invasive ductal carcinoma of the breast. Med J Malaysia 62, 6-8.

Altman J D, Moss P A, Goulder P J, Barouch D H, Heyzer-Williams M G, Bell J I, McMichael A J, Davis M M (1996). Phenotypic analysis of antigen-specific T lymphocytes. Science 274, 94-96.

Angileri F F, Aguennouz M, Conti A, La T D, Cardali S, Crupi R, Tomasello C, Germano A, Vita G, Tomasello F (2008). Nuclear factor-kappaB activation and differential expression of survivin and Bcl-2 in human grade 2-4 astrocytomas. Cancer.

Ariyama T, Hasegawa K, Inazawa J, Mizuno K, Ogimoto M, Katagiri T, Yakura H (1995). Assignment of the human protein tyrosine phosphatase, receptor-type, zeta (PTPRZ) gene to chromosome band 7q31.3. Cytogenet. Cell Genet. 70, 52-54.

Banchereau J, Palucka A K, Dhodapkar M, Burkeholder S, Taquet N, Rolland A, Taquet S, Coquery S, Wittkowski K M, Bhardwaj N, Pineiro L, Steinman R, Fay J (2001). Immune and clinical responses in patients with metastatic melanoma to CD34(+) progenitor-derived dendritic cell vaccine. Cancer Res. 61, 6451-6458.

Barnea G, Silvennoinen O, Shaanan B, Honegger A M, Canoll P D, D'Eustachio P, Morse B, Levy J B, Laforgia S, Huebner K, (1993). Identification of a carbonic anhydrase-like domain in the extracellular region of RPTP gamma defines a new subfamily of receptor tyrosine phosphatases. Mol. Cell. Biol. 13, 1497-1506.

Bartsch S, Bartsch U, Dorries U, Faissner A, Weller A, Ekblom P, Schachner M (1992). Expression of tenascin in the developing and adult cerebellar cortex. J. Neurosci. 12, 736-749.

Beilmann M, Vande Woude G F, Dienes H P, Schirmacher P (2000). Hepatocyte growth factor-stimulated invasiveness of monocytes. Blood 95, 3964-3969.

Bertoletti A, Chisari F V, Penna A, Guilhot S, Galati L, Missale G, Fowler P, Schlicht H J, Vitiello A, Chesnut R C, (1993). Definition of a minimal optimal cytotoxic T-cell epitope within the hepatitis B virus nucleocapsid protein. J. Virol. 67, 2376-2380.

Bladt F, Riethmacher D, Isenmann S, Aguzzi A, Birchmeier C (1995). Essential role for the c-met receptor in the migration of myogenic precursor cells into the limb bud. Nature 376, 768-771.

Blum R, Jacob-Hirsch J, Rechavi G, Kloog Y (2006). Suppression of survivin expression in glioblastoma cells by the Ras inhibitor farnesylthiosalicylic acid promotes caspase-dependent apoptosis. Mol. Cancer. Ther. 5, 2337-2347.

Bolliger M F, Frei K, Winterhalter K H, Gloor S M (2001). Identification of a novel neuroligin in humans which binds to PSD-95 and has a widespread expression. Biochem. J. 356, 581-588.

Bottaro D P, Rubin J S, Faletto D L, Chan A M, Kmiecik T E, Vande Woude G F, Aaronson S A (1991). Identification of the hepatocyte growth factor receptor as the c-met proto-oncogene product. Science 251, 802-804.

Bourdon M A, Wikstrand C J, Furthmayr H, Matthews T J, Bigner D D (1983). Human glioma-mesenchymal extracellular matrix antigen defined by monoclonal antibody. Cancer Res. 43, 2796-2805.

Bowen A R, Hanks A N, Murphy K J, Florell S R, Grossman D (2004). Proliferation, apoptosis, and survivin expression in keratinocytic neoplasms and hyperplasias. Am J. Dermatopathol. 26, 177-181.

Brekke C, Lundervold A, Enger P O, Brekken C, Stalsett E, Pedersen T B, Haraldseth O, Kruger P G, Bjerkvig R, Chekenya M (2006). NG2 expression regulates vascular morphology and function in human brain tumours. Neuroimage. 29, 965-976.

Campoli M R, Chang C C, Kageshita T, Wang X, McCarthy J B, Ferrone S (2004). Human high molecular weightmelanoma-associated antigen (HMW-MAA): a melanoma cell surface chondroitin sulfate proteoglycan (MSCP) with biological and clinical significance. Crit. Rev. Immunol. 24, 267-296.

Casati C, Dalerba P, Rivoltini L, Gallino G, Deho P, Rini F, Belli F, Mezzanzanica D, Costa A, Andreola S, Leo E, Parmiani G, Castelli C (2003). The apoptosis inhibitor protein survivin induces tumor-specific CD8+ and CD4+ T cells in colorectal cancer patients. Cancer Res. 63, 4507-4515.

Chakravarti A, Noll E, Black P M, Finkelstein D F, Finkelstein D M, Dyson N J, Loeffler J S (2002). Quantitatively determined survivin expression levels are of prognostic value in human gliomas. J Clin Oncol 20, 1063-1068.

Chanock S J, Foster C B, Miller F W, O'Hanlon T P (2004). HLA-A, -B, -Cw, -DQA1 and -DRB1 Alleles in a Caucasian Population from Bethesda, USA. Hum. Immunol. 65, 1211-1223.

Chekenya M, Enger P O, Thorsen F, Tysnes B B, Al-Sarraj S, Read T A, Furmanek T, Mahesparan R, Levine J M, Butt A M, Pilkington G J, Bjerkvig R (2002a). The glial precursor proteoglycan, NG2, is expressed on tumour neovasculature by vascular pericytes in human malignant brain tumours. Neuropathol. Appl. Neurobiol. 28, 367-380.

Chekenya M, Hjelstuen M, Enger P O, Thorsen F, Jacob A L, Probst B, Haraldseth O, Pilkington G, Butt A, Levine J M, Bjerkvig R (2002b). NG2 proteoglycan promotes angiogenesis-dependent tumor growth in CNS by sequestering angiostatin. FASEB J 16, 586-588.

Chekenya M, Immervoll H (2007). NG2/HMP proteoglycan as a cancer therapeutic target. Methods Mol. Biol. 361, 93-117.

Chekenya M, Krakstad C, Svendsen A, Netland I A, Staalesen V, Tysnes B B, Selheim F, Wang J, Sakariassen P O, Sandal T, Lonning P E, Flatmark T, Enger P O, Bjerkvig R, Sioud M, Stallcup W B (2008). The progenitor cell marker NG2/MPG promotes chemoresistance by activation of integrin-dependent PI3K/Akt signaling. Oncogene.

Chekenya M, Pilkington G J (2002). NG2 precursor cells in neoplasia: functional, histogenesis and therapeutic implications for malignant brain tumours. J. Neurocytol. 31, 507-521.

Chekenya M, Rooprai H K, Davies D, Levine J M, Butt A M, Pilkington G J (1999). The NG2 chondroitin sulfate proteoglycan: role in malignant progression of human brain tumours. Int J. Dev. Neurosci. 17, 421-435.

Chiquet-Ehrismann R (1993). Tenascin and other adhesion-modulating proteins in cancer. Semin. Cancer Biol. 4, 301-310.

Chiquet-Ehrismann R, Chiquet M (2003). Tenascins: regulation and putative functions during pathological stress. J. Pathol. 200, 488-499.

Conacci-Sorrell M, Kaplan A, Raveh S, Gavert N, Sakurai T, Ben-Ze'ev A (2005). The shed ectodomain of Nr-CAM stimulates cell proliferation and motility, and confers cell transformation. Cancer Res. 65, 11605-11612.

Conacci-Sorrell M E, Ben-Yedidia T, Shtutman M, Feinstein E, Einat P, Ben-Ze'ev A (2002). Nr-CAM is a target gene of the beta-catenin/LEF-1 pathway in melanoma and colon cancer and its expression enhances motility and confers tumorigenesis. Genes Dev. 16, 2058-2072.

Corso S, Migliore C, Ghiso E, De R G, Comoglio P M, Giordano S (2008). Silencing the MET oncogene leads to regression of experimental tumors and metastases. Oncogene 27, 684-693.

Davis J Q, Bennett V (1994) Ankyrin binding activity shared by the neurofascin/L1/NrCAM family of nervous system cell adhesion molecules. J. Biol. Chem. 269, 27163-27166.

Di Renzo M F, Olivero M, Giacomini A, Porte H, Chastre E, Mirossay L, Nordlinger B, Bretti S, Bottardi S, Giordano S, (1995). Overexpression and amplification of the met/HGF receptor gene during the progression of colorectal cancer. Clin. Cancer Res. 1, 147-154.

Di Renzo M F, Olivero M, Martone T, Maffe A, Maggiora P, Stefani A D, Valente G, Giordano S, Cortesina G, Comoglio P M (2000). Somatic mutations of the MET oncogene are selected during metastatic spread of human HNSC carcinomas. Oncogene 19, 1547-1555.

Dong G, Chen Z, Li Z Y, Yeh N T, Bancroft C C, Van W C (2001). Hepatocyte growth factor/scatter factor-induced activation of MEK and PI3K signal pathways contributes to expression of proangiogenic cytokines interleukin-8 and vascular endothelial growth factor in head and neck squamous cell carcinoma. Cancer Res. 61, 5911-5918.

Ebert M, Yokoyama M, Friess H, Buchler M W, Korc M (1994). Coexpression of the c-met proto-oncogene and hepatocyte growth factor in human pancreatic cancer. Cancer Res. 54, 5775-5778.

Eckerich C, Zapf S, Fillbrandt R, Loges S, Westphal M, Lamszus K (2007). Hypoxia can induce c-Met expression in glioma cells and enhance SF/HGF-induced cell migration. Int J Cancer 121, 276-283.

Erfurt C, Sun Z, Haendle I, Schuler-Thurner B, Heirman C, Thielemans K, van der BP, Schuler G, Schultz E S (2007). Tumor-reactive CD4+ T cell responses to the melanoma-associated chondroitin sulphate proteoglycan in melanoma patients and healthy individuals in the absence of autoimmunity. J. Immunol. 178, 7703-7709.

Feng L, Hatten M E, Heintz N (1994). Brain lipid-binding protein (BLBP): a novel signaling system in the developing mammalian CNS. Neuron 12, 895-908.

Feng L, Heintz N (1995). Differentiating neurons activate transcription of the brain lipid-binding protein gene in radial glia through a novel regulatory element. Development 121, 1719-1730.

Ferracini R, Di Renzo M F, Scotlandi K, Baldini N, Olivero M, Lollini P, Cremona O, Campanacci M, Comoglio P M (1995). The Met/HGF receptor is over-expressed in human osteosarcomas and is activated by either a paracrine or an autocrine circuit. Oncogene 10, 739-749.

Fischer J, Palmedo G, von K R, Bugert P, Prayer-Galetti T, Pagano F, Kovacs G (1998). Duplication and overexpression of the mutant allele of the MET proto-oncogene in multiple hereditary papillary renal cell tumours. Oncogene 17, 733-739.

Furge K A, Kiewlich D, Le P, Vo M N, Faure M, Howlett A R, Lipson K E, Woude G F, Webb C P (2001). Suppression of Ras-mediated tumorigenicity and metastasis through inhibition of the Met receptor tyrosine kinase. Proc. Natl. Acad. Sci. U.S. A 98, 10722-10727.

Furge K A, Zhang Y W, Vande Woude G F (2000). Met receptor tyrosine kinase: enhanced signaling through adapter proteins. Oncogene 19, 5582-5589.

Garcion E, Halilagic A, Faissner A, ffrench-Constant C (2004). Generation of an environmental niche for neural stem cell development by the extracellular matrix molecule tenascin C. Development 131, 3423-3432.

Gary S C, Kelly G M, Hockfield S (1998). BEHAB/brevican: a brain-specific lectican implicated in gliomas and glial cell motility. Curr. Opin. Neurobiol. 8, 576-581.

Gary S C, Zerillo C A, Chiang V L, Gaw J U, Gray G, Hockfield S (2000). cDNA cloning, chromosomal localization, and expression analysis of human BEHAB/brevican, a brain specific proteoglycan regulated during cortical development and in glioma. Gene 256, 139-147.

Gebbink M F, van E, I, Hateboer G, Suijkerbuijk R, Beijersbergen R L, Geurts van K A, Moolenaar W H (1991). Cloning, expression and chromosomal localization of a new putative receptor-like protein tyrosine phosphatase. FEBS Lett. 290, 123-130.

Ghosh J C, Dohi T, Kang B H, Altieri D C (2008). Hsp60 regulation of tumor cell apoptosis. J. Biol. Chem. 283, 5188-5194.

Giordano S, Ponzetto C, Di Renzo M F, Cooper C S, Comoglio P M (1989). Tyrosine kinase receptor indistinguishable from the c-met protein. Nature 339, 155-156.

Glass R, Synowitz M, Kronenberg G, Walzlein J H, Markovic D S, Wang L P, Gast D, Kiwit J, Kempermann G, Kettenmann H (2005). Glioblastoma-induced attraction of endogenous neural precursor cells is associated with improved survival. J. Neurosci. 25, 2637-2646.

Glatz J F, Luiken J J, van B M, van d, V (2002). Cellular lipid binding proteins as facilitators and regulators of lipid metabolism. Mol. Cell. Biochem. 239, 3-7.

Glatz J F, Storch J (2001). Unravelling the significance of cellular fatty acid-binding proteins. Curr. Opin. Lipidol. 12, 267-274.

Godbout R, Bisgrove D A, Shkolny D, Day R S, III (1998). Correlation of B-FABP and GFAP expression in malignant glioma. Oncogene 16, 1955-1962.

Grumet M, Mauro V, Burgoon M P, Edelman G M, Cunningham B A (1991). Structure of a new nervous system glycoprotein, Nr-CAM, and its relationship to subgroups of neural cell adhesion molecules. J. Cell Biol. 113, 1399-1412.

Grunda J M, Nabors L B, Palmer C A, Chhieng D C, Steg A, Mikkelsen T, Diasio R B, Zhang K, Allison D, Grizzle W E, Wang W, Gillespie G Y, Johnson M R (2006). Increased expression of thymidylate synthetase (TS), ubiquitin specific protease 10 (USP10) and survivin is associated with poor survival in glioblastoma multiforme (GBM). J. Neurooncol. 80, 261-274.

Gunther H S, Schmidt N O, Phillips H S, Kemming D, Kharbanda S, Soriano R, Modrusan Z, Meissner H, Westphal M, Lamszus K (2008). Glioblastoma-derived stem cell-enriched cultures form distinct subgroups according to molecular and phenotypic criteria. Oncogene 27, 2897-2909.

Harroch S, Furtado G C, Brueck W, Rosenbluth J, Lafaille J, Chao M, Buxbaum J D, Schlessinger J (2002). A critical role for the protein tyrosine phosphatase receptor type Z in functional recovery from demyelinating lesions. Nat. Genet. 32, 411-414.

Hau P, Kunz-Schughart L A, Rummele P, Arslan F, Dorfelt A, Koch H, Lohmeier A, Hirschmann B, Muller A, Bogdahn U, Bosserhoff A K (2006). Tenascin-C protein is induced by transforming growth factor-beta1 but does not correlate with time to tumor progression in high-grade gliomas. J. Neurooncol. 77, 1-7.

Heimberger A B, Hussain S F, Aldape K, Sawaya R, Archer G A, Friedman H, Reardon D, Friedman A, Bigner D D, Sampson J H. Tumor-specific peptide vaccination in newly-diagnosed patients with GBM. Journal of Clinical Oncology, 2006 ASCO Annual Meeting Proceedings Part I Vol 24, No. 18S (June 20 Supplement), 2006: 2529. 20 Jun. 2006.

Herold-Mende C, Mueller M M, Bonsanto M M, Schmitt H P, Kunze S, Steiner H H (2002). Clinical impact and functional aspects of tenascin-C expression during glioma progression. Int. J. Cancer 98, 362-369.

Hoffmann N E, Sheinin Y, Lohse C M, Parker A S, Leibovich B C, Jiang Z, Kwon E D (2008). External validation of IMP3 expression as an independent prognostic marker for metastatic progression and death for patients with clear cell renal cell carcinoma. Cancer 112, 1471-1479.

Hu B, Kong L L, Matthews R T, Viapiano M S (2008). The proteoglycan brevican binds to fibronectin after proteolytic cleavage and promotes glioma cell motility. J. Biol. Chem.

Huang P H, Cavenee W K, Furnari F B, White F M (2007a). Uncovering therapeutic targets for glioblastoma: a systems biology approach. Cell Cycle 6, 2750-2754.

Huang P H, Mukasa A, Bonavia R, Flynn R A, Brewer Z E, Cavenee W K, Furnari F B, White F M (2007b). Quantitative analysis of EGFRvIII cellular signaling networks reveals a combinatorial therapeutic strategy for glioblastoma. Proc Natl. Acad. Sci. U.S. A 104, 12867-12872.

Jamain S, Quach H, Betancur C, Rastam M, Colineaux C, Gillberg I C, Soderstrom H, Giros B, Leboyer M, Gillberg C, Bourgeron T (2003). Mutations of the X-linked genes encoding neuroligins NLGN3 and NLGN4 are associated with autism. Nat. Genet. 34, 27-29.

Jaworski D M, Fager N (2000). Regulation of tissue inhibitor of metalloproteinase-3 (Timp-3) mRNA expression during rat CNS development. J. Neurosci. Res. 61, 396-408.

Jaworski D M, Kelly G M, Hockfield S (1999). Intracranial injury acutely induces the expression of the secreted isoform of the CNS-specific hyaluronan-binding protein BEHAB/brevican. Exp. Neurol. 157, 327-337.

Jaworski D M, Kelly G M, Piepmeier J M, Hockfield S (1996). BEHAB (brain enriched hyaluronan binding) is expressed in surgical samples of glioma and in intracranial grafts of invasive glioma cell lines. Cancer Res. 56, 2293-2298.

Jiang Z, Chu P G, Woda B A, Rock K L, Liu Q, Hsieh C C, Li C, Chen W, Duan H O, McDougal S, Wu C L (2006). Analysis of RNA-binding protein IMP3 to predict metastasis and prognosis of renal-cell carcinoma: a retrospective study. Lancet Oncol 7, 556-564.

Jiang Z, Lohse C M, Chu P G, Wu C L, Woda B A, Rock K L, Kwon E D (2008). Oncofetal protein IMP3: a novel molecular marker that predicts metastasis of papillary and chromophobe renal cell carcinomas. Cancer 112, 2676-2682.

Jung G, Ledbetter J A, Muller-Eberhard H J (1987). Induction of cytotoxicity in resting human T lymphocytes bound to tumor cells by antibody heteroconjugates. Proc Natl Acad Sci USA 84, 4611-4615.

Kajiwara Y, Yamasaki F, Hama S, Yahara K, Yoshioka H, Sugiyama K, Arita K, Kurisu K (2003). Expression of survivin in astrocytic tumors: correlation with malignant grade and prognosis. Cancer 97, 1077-1083.

Kaloshi G, Mokhtari K, Carpentier C, Taillibert S, Lejeune J, Marie Y, Delattre J Y, Godbout R, Sanson M (2007). FABP7 expression in glioblastomas: relation to prognosis, invasion and EGFR status. J. Neurooncol. 84, 245-248.

Kammula U S, Kuntz E J, Francone T D, Zeng Z, Shia J, Landmann R G, Paty P B, Weiser M R (2007). Molecular co-expression of the c-Met oncogene and hepatocyte growth factor in primary colon cancer predicts tumor stage and clinical outcome. Cancer Lett. 248, 219-228.

Kaplan R, Morse B, Huebner K, Croce C, Howk R, Ravera M, Ricca G, Jaye M, Schlessinger J (1990). Cloning of three human tyrosine phosphatases reveals a multigene family of receptor-linked protein-tyrosine-phosphatases expressed in brain. Proc Natl. Acad. Sci. U.S. A 87, 7000-7004.

Kendall S E, Najbauer J, Johnston H F, Metz M Z, Li S, Bowers M, Garcia E, Kim S U, Barish M E, Aboody K S, Glackin C A (2008). Neural Stem Cell Targeting of Glioma is Dependent on PI3K Signaling. Stem Cells.

Kim C H, Bak K H, Kim Y S, Kim J M, Ko Y, Oh S J, Kim K M, Hong E K (2000). Expression of tenascin-C in astrocytic tumors: its relevance to proliferation and angiogenesis. Surg Neurol. 54, 235-240.

Knutson K L, Disis M L (2005). Augmenting T helper cell immunity in cancer. Curr. Drug Targets. Immune. Endocr. Metabol. Disord. 5, 365-371.

Koochekpour S, Jeffers M, Rulong S, Taylor G, Klineberg E, Hudson E A, Resau J H, Vande Woude G F (1997). Met and hepatocyte growth factor/scatter factor expression in human gliomas. Cancer Res. 57, 5391-5398.

Kosari F, Parker A S, Kube D M, Lohse C M, Leibovich B C, Blute M L, Cheville J C, Vasmatzis G (2005). Clear cell renal cell carcinoma: gene expression analyses identify a potential signature for tumor aggressiveness. Clin Cancer Res. 11, 5128-5139.

Krueger N X, Streuli M, Saito H (1990). Structural diversity and evolution of human receptor-like protein tyrosine phosphatases. EMBO J. 9, 3241-3252.

Kucharczak J, Pannequin J, Camby I, Decaestecker C, Kiss R, Martinez J (2001). Gastrin induces over-expression of genes involved in human U373 glioblastoma cell migration. Oncogene 20, 7021-7028.

Kurtz A, Zimmer A, Schnutgen F, Bruning G, Spener F, Muller T (1994). The expression pattern of a novel gene encoding brain-fatty acid binding protein correlates with neuronal and glial cell development. Development 120, 2637-2649.

Lal A, Peters H, St C B, Haroon Z A, Dewhirst M W, Strausberg R L, Kaanders J H, van der Kogel A J, Riggins G J (2001). Transcriptional response to hypoxia in human tumors. J. Natl. Cancer Inst. 93, 1337-1343.

Laumonnier F, Bonnet-Brilhault F, Gomot M, Blanc R, David A, Moizard M P, Raynaud M, Ronce N, Lemonnier E, Calvas P, Laudier B, Chelly J, Fryns J P, Ropers H H, Hamel B C, Andres C, Barthelemy C, Moraine C, Briault S (2004). X-linked mental retardation and autism are associated with a mutation in the NLGN4 gene, a member of the neuroligin family. Am J. Hum. Genet. 74, 552-557.

Lawson-Yuen A, Saldivar J S, Sommer S, Picker J (2008). Familial deletion within NLGN4 associated with autism and Tourette syndrome. Eur. J. Hum. Genet. 16, 614-618.

Levy J B, Canoll P D, Silvennoinen O, Barnea G, Morse B, Honegger A M, Huang J T, Cannizzaro L A, Park S H, Druck T, (1993). The cloning of a receptor-type protein tyrosine phosphatase expressed in the central nervous system. J. Biol. Chem. 268, 10573-10581.

Li G, Schaider H, Satyamoorthy K, Hanakawa Y, Hashimoto K, Herlyn M (2001). Downregulation of E-cadherin and Desmoglein 1 by autocrine hepatocyte growth factor during melanoma development. Oncogene 20, 8125-8135.

Li L, Xu H, Spaulding B O, Cheng L, Simon R, Yao J L, di Sant'agnese P A, Bourne P A, Huang J (2008). Expression of RNA-binding protein IMP3 (KOC) in benign urothelium and urothelial tumors. Hum. Pathol.

Liang Y, Bollen A W, Aldape K D, Gupta N (2006). Nuclear FABP7 immunoreactivity is preferentially expressed in infiltrative glioma and is associated with poor prognosis in EGFR-overexpressing glioblastoma. BMC. Cancer 6, 97.

Liang Y, Diehn M, Watson N, Bollen A W, Aldape K D, Nicholas M K, Lamborn K R, Berger M S, Botstein D, Brown P O, Israel M A (2005). Gene expression profiling reveals molecularly and clinically distinct subtypes of glioblastoma multiforme. Proc. Natl. Acad. Sci. U.S. A 102, 5814-5819.

Liao B, Hu Y, Herrick D J, Brewer G (2005). The RNA-binding protein IMP-3 is a translational activator of insulin-like growth factor II leader-3 mRNA during proliferation of human K562 leukemia cells. J. Biol. Chem. 280, 18517-18524.

Liu X, Chen N, Wang X, He Y, Chen X, Huang Y, Yin W, Zhou Q (2006). Apoptosis and proliferation markers in diffusely infiltrating astrocytomas: profiling of 17 molecules. J. Neuropathol. Exp. Neurol. 65, 905-913.

Livingston B D, Crimi C, Grey H, Ishioka G, Chisari F V, Fikes J, Grey H, Chesnut R W, Sette A (1997). The hepatitis B virus-specific CTL responses induced in humans by lipopeptide vaccination are comparable to those elicited by acute viral infection. J. Immunol. 159, 1383-1392.

Lo M L, Staibano S, Pannone G, Mignogna M D, Mariggio A, Salvatore G, Chieffi P, Tramontano D, De R G, Altieri D C (2001). Expression of the apoptosis inhibitor survivin in aggressive squamous cell carcinoma. Exp. Mol. Pathol. 70, 249-254.

Long I S, Han K, Li M, Shirasawa S, Sasazuki T, Johnston M, Tsao M S (2003). Met receptor overexpression and oncogenic Ki-ras mutation cooperate to enhance tumorigenicity of colon cancer cells in vivo. Mol. Cancer. Res. 1, 393-401.

Lu K V, Jong K A, Kim G Y, Singh J, Dia E Q, Yoshimoto K, Wang M Y, Cloughesy T F, Nelson S F, Mischel P S (2005). Differential induction of glioblastoma migration and growth by two forms of pleiotrophin. J Biol. Chem. 280, 26953-26964.

Mackie E J, Halfter W, Liverani D (1988). Induction of tenascin in healing wounds. J. Cell Biol. 107, 2757-2767.

Mahlamaki E H, Barlund M, Tanner M, Gorunova L, Hoglund M, Karhu R, Kallioniemi A (2002). Frequent amplification of 8q24, 11q, 17q, and 20q-specific genes in pancreatic cancer. Genes Chromosomes. Cancer 35, 353-358.

Maulik G, Kijima T, Ma P C, Ghosh S K, Lin J, Shapiro G I, Schaefer E, Tibaldi E, Johnson B E, Salgia R (2002). Modulation of the c-Met/hepatocyte growth factor pathway in small cell lung cancer. Clin. Cancer Res. 8, 620-627.

Mellai M, Caldera V, Patrucco A, Annovazzi L, Schiffer D (2008). Survivin expression in glioblastomas correlates with proliferation, but not with apoptosis. Anticancer Res. 28, 109-118.

Miller S J, Li H, Rizvi T A, Huang Y, Johansson G, Bowersock J, Sidani A, Vitullo J, Vogel K, Parysek L M, DeClue J E, Ratner N (2003). Brain lipid binding protein in axon-Schwann cell interactions and peripheral nerve tumorigenesis. Mol. Cell. Biol. 23, 2213-2224.

Mita R, Coles J E, Glubrecht D D, Sung R, Sun X, Godbout R (2007). B-FABP-expressing radial glial cells: the malignant glioma cell of origin? Neoplasia. 9, 734-744.

Mizukami Y, Kono K, Daigo Y, Takano A, Tsunoda T, Kawaguchi Y, Nakamura Y, Fujii H (2008). Detection of novel cancer-testis antigen-specific T-cell responses in TIL, regional lymph nodes, and PBL in patients with esophageal squamous cell carcinoma. Cancer Sci.

Mizuno K, Higuchi O, Ihle J N, Nakamura T (1993). Hepatocyte growth factor stimulates growth of hematopoietic progenitor cells. Biochem. Biophys. Res. Commun. 194, 178-186.

Molenkamp B G, Vuylsteke R J, van Leeuwen P A, Meijer S, Vos W, Wijnands P G, Scheper R J, de Gruijl T D (2005). Matched skin and sentinel lymph node samples of melanoma patients reveal exclusive migration of mature dendritic cells. Am. J. Pathol. 167, 1301-1307.

Mondino A, Giordano S, Comoglio P M (1991). Defective posttranslational processing activates the tyrosine kinase encoded by the MET proto-oncogene (hepatocyte growth factor receptor). Mol. Cell. Biol. 11, 6084-6092.

Montesano R, Soriano J V, Malinda K M, Ponce M L, Bafico A, Kleinman H K, Bottaro D P, Aaronson S A (1998). Differential effects of hepatocyte growth factor isoforms on epithelial and endothelial tubulogenesis. Cell Growth Differ. 9, 355-365.

Morales G, Hubert M, Brummendorf T, Treubert U, Tarnok A, Schwarz U, Rathjen F G (1993). Induction of axonal growth by heterophilic interactions between the cell surface recognition proteins F11 and Nr-CAM/Bravo. Neuron 11, 1113-1122.

Mori M, Beatty P G, Graves M, Boucher K M, Milford E L (1997). HLA gene and haplotype frequencies in the North American population: the National Marrow Donor Program Donor Registry. Transplantation 64, 1017-1027.

Moriyama T, Kataoka H, Koono M, Wakisaka S (1999). Expression of hepatocyte growth factor/scatter factor and its receptor c-Met in brain tumors: evidence for a role in progression of astrocytic tumors (Review). Int J. Mol. Med. 3, 531-536.

Mueller-Pillasch F, Lacher U, Wallrapp C, Micha A, Zimmerhackl F, Hameister H, Varga G, Friess H, Buchler M, Beger H G, Vila M R, Adler G, Gress T M (1997). Cloning of a gene highly overexpressed in cancer coding for a novel KH-domain containing protein. Oncogene 14, 2729-2733.

Mulholland P J, Fiegler H, Mazzanti C, Gorman P, Sasieni P, Adams J, Jones T A, Babbage J W, Vatcheva R, Ichimura K, East P, Poullikas C, Collins V P, Carter N P, Tomlinson I P, Sheer D (2006). Genomic profiling identifies discrete deletions associated with translocations in glioblastoma multiforme. Cell Cycle 5, 783-791.

Nakaigawa N, Yao M, Baba M, Kato S, Kishida T, Hattori K, Nagashima Y, Kubota Y (2006). Inactivation of von Hippel-Lindau gene induces constitutive phosphorylation of MET protein in clear cell renal carcinoma. Cancer Res. 66, 3699-3705.

Naldini L, Vigna E, Narsimhan R P, Gaudino G, Zarnegar R, Michalopoulos G K, Comoglio P M (1991). Hepatocyte growth factor (HGF) stimulates the tyrosine kinase activity of the receptor encoded by the proto-oncogene c-MET. Oncogene 6, 501-504.

Nam D H, Kong D S, Kyeung M J, Kim S. c-MET: A Potential Candidate of Glioblastoma Cancer Stem Cell Targeted Marker. The Role of Cancer Stem Cells in the Initiation and Propagation of Tumorigenesis—An AACR Special Conference in Cancer Research, Los Angeles. Conference Proceedings, A45. 12 Feb. 2008. 12-2-0080. Ref Type: Conference Proceeding Neumann F, Wagner C, Kubuschok B, Stevanovic S, Rammensee H G, Pfreundschuh M (2004). Identification of an antigenic peptide derived from the cancer-testis antigen NY-ESO-1 binding to a broad range of HLA-DR subtypes. Cancer Immunol. Immunother. 53, 589-599.

Nutt C L, Matthews R T, Hockfield S (2001). Glial tumor invasion: a role for the upregulation and cleavage of BEHAB/brevican. Neuroscientist. 7, 113-122.

O'Driscoll L, Linehan R, Clynes M (2003). Survivin: role in normal cells and in pathological conditions. Curr. Cancer Drug Targets. 3, 131-152.

Oka Y, Tsuboi A, Taguchi T, Osaki T, Kyo T, Nakajima H, Elisseeva O A, Oji Y, Kawakami M, Ikegame K, Hosen N, Yoshihara S, Wu F, Fujiki F, Murakami M, Masuda T, Nishida S, Shirakata T, Nakatsuka S, Sasaki A, Udaka K, Dohy H, Aozasa K, Noguchi S, Kawase I, Sugiyama H (2004). Induction of WT1 (Wilms' tumor gene)-specific cytotoxic T lymphocytes by WT1 peptide vaccine and the resultant cancer regression. Proc Natl. Acad. Sci. U.S. A 101, 13885-13890.

Olivero M, Valente G, Bardelli A, Longati P, Ferrero N, Cracco C, Terrone C, Rocca-Rossetti S, Comoglio P M, Di Renzo M F (1999). Novel mutation in the ATP-binding site of the MET oncogene tyrosine kinase in a HPRCC family. Int. J. Cancer 82, 640-643.

Pai R, Nakamura T, Moon W S, Tarnawski A S (2003). Prostaglandins promote colon cancer cell invasion; signaling by cross-talk between two distinct growth factor receptors. FASEB J 17, 1640-1647.

Park M, Dean M, Cooper C S, Schmidt M, O'Brien S J, Blair D G, Vande Woude G F (1986). Mechanism of met oncogene activation. Cell 45, 895-904.

Park W S, Dong S M, Kim S Y, Na E Y, Shin M S, Pi J H, Kim B J, Bae J H, Hong Y K, Lee K S, Lee S H, Yoo N J, Jong J J, Pack S, Zhuang Z, Schmidt L, Zbar B, Lee J Y (1999). Somatic mutations in the kinase domain of the Met/hepatocyte growth factor receptor gene in childhood hepatocellular carcinomas. Cancer Res. 59, 307-310.

Perez-Pinera P, Garcia-Suarez O, Menendez-Rodriguez P, Mortimer J, Chang Y, Astudillo A, Deuel T F (2007). The receptor protein tyrosine phosphatase (RPTP)beta/zeta is expressed in different subtypes of human breast cancer. Biochem. Biophys. Res. Commun. 362, 5-10.

Perrin F E, Rathjen F G, Stoeckli E T (2001). Distinct subpopulations of sensory afferents require F11 or axonin-1 for growth to their target layers within the spinal cord of the chick. Neuron 30, 707-723.

Phillips H S, Kharbanda S, Chen R, Forrest W F, Soriano R H, Wu T D, Misra A, Nigro J M, Colman H, Soroceanu L, Williams P M, Modrusan Z, Feuerstein B G, Aldape K (2006). Molecular subclasses of high-grade glioma predict prognosis, delineate a pattern of disease progression, and resemble stages in neurogenesis. Cancer Cell 9, 157-173.

Piesche M, Hildebrandt Y, Zettl F, Chapuy B, Schmitz M, Wulf G, Trumper L, Schroers R (2007). Identification of a promiscuous HLA DR-restricted T-cell epitope derived from the inhibitor of apoptosis protein survivin. Hum. Immunol. 68, 572-576.

Ponzetto C, Bardelli A, Maina F, Longati P, Panayotou G, Dhand R, Waterfield M D, Comoglio P M (1993). A novel recognition motif for phosphatidylinositol 3-kinase binding mediates its association with the hepatocyte growth factor/scatter factor receptor. Mol. Cell. Biol. 13, 4600-4608.

Prakash S, Sarran L, Socci N, DeMatteo R P, Eisenstat J, Greco A M, Maki R G, Wexler L H, LaQuaglia M P, Besmer P, Antonescu C R (2005). Gastrointestinal stromal tumors in children and young adults: a clinicopathologic, molecular, and genomic study of 15 cases and review of the literature. J. Pediatr. Hematol. Oncol 27, 179-187.

Previsani, N. and Lavanchy, D.: Hepatitis B (internal immatics research report)

Pryor J G, Bourne P A, Yang Q, Spaulding B O, Scott G A, Xu H (2008). IMP-3 is a novel progression marker in malignant melanoma. Mod. Pathol. 21, 431-437.

Qian C N, Guo X, Cao B, Kort E J, Lee C C, Chen J, Wang L M, Mai W Y, Min H Q, Hong M H, Vande Woude G F, Resau J H, Teh B T (2002). Met protein expression level correlates with survival in patients with late-stage nasopharyngeal carcinoma. Cancer Res. 62, 589-596.

Rahimi N, Tremblay E, McAdam L, Park M, Schwall R, Elliott B (1996). Identification of a hepatocyte growth factor autocrine loop in a murine mammary carcinoma. Cell Growth Differ. 7, 263-270.

Ramirez R, Hsu D, Patel A, Fenton C, Dinauer C, Tuttle R M, Francis G L (2000). Over-expression of hepatocyte growth factor/scatter factor (HGF/SF) and the HGF/SF receptor (cMET) are associated with a high risk of metastasis and recurrence for children and young adults with papillary thyroid carcinoma. Clin Endocrinol. (Oxf) 53, 635-644.

Rammensee H G, Bachmann J, Emmerich N P, Bachor O A, Stevanović S (1999). SYFPEITHI: database for MHC ligands and peptide motifs. Immunogenetics 50, 213-219.

Rammensee, H. G., Bachmann, J., and Stevanovic, S. (1997). MHC Ligands and Peptide Motifs. Springer-Verlag, Heidelberg, Germany).

Rammensee H G, Falk K, Rotzschke O (1993). Peptides naturally presented by MHC class I molecules. Annu Rev. Immunol. 11, 213-244.

Rasola A, Fassetta M, De B F, D'Alessandro L, Gramaglia D, Di Renzo M F, Comoglio P M (2007). A positive feedback loop between hepatocyte growth factor receptor and beta-catenin sustains colorectal cancer cell invasive growth. Oncogene 26, 1078-1087.

Reardon D A, Cloughesy T F, Raizer J J, Laterra J, Schiff D, Yang X, Loh E, Wen P Y. Phase II study of AMG 102, a fully human neutralizing antibody against hepatocyte growth factor/scatter factor, in patients with recurrent glioblastoma multiforme. ASCO Meeting Abstracts 26 (May 20 suppl)[2051]. 20 May, 2008.

Rehermann B, Nascimbeni M (2005). Immunology of hepatitis B virus and hepatitis C virus infection. Nat. Rev. Immunol. 5, 215-229.

Reznik T E, Sang Y, Ma Y, Abounader R, Rosen E M, Xia S, Laterra J (2008). Transcription-dependent epidermal growth factor receptor activation by hepatocyte growth factor. Mol. Cancer. Res. 6, 139-150.

Rubin J S, Bottaro D P, Aaronson S A (1993). Hepatocyte growth factor/scatter factor and its receptor, the c-met proto-oncogene product. Biochim. Biophys. Acta 1155, 357-371.

Ruiz C, Huang W, Hegi M E, Lange K, Hamou M F, Fluri E, Oakeley E J, Chiquet-Ehrismann R, Orend G (2004). Growth promoting signaling by tenascin-C [corrected]. Cancer Res. 64, 7377-7385.

Saito T, Arifin M T, Hama S, Kajiwara Y, Sugiyama K, Yamasaki F, Hidaka T, Arita K, Kurisu K (2007). Survivin subcellular localization in high-grade astrocytomas: simultaneous expression in both nucleus and cytoplasm is negative prognostic marker. J. Neurooncol. 82, 193-198.

Sakurai T, Lustig M, Babiarz J, Furley A J, Tait S, Brophy P J, Brown S A, Brown L Y, Mason C A, Grumet M (2001). Overlapping functions of the cell adhesion molecules Nr-CAM and L1 in cerebellar granule cell development. J. Cell Biol. 154, 1259-1273.

Sakurai T, Lustig M, Nativ M, Hemperly J J, Schlessinger J, Peles E, Grumet M (1997). Induction of neurite outgrowth through contactin and Nr-CAM by extracellular regions of glial receptor tyrosine phosphatase beta. J. Cell Biol. 136, 907-918.

Sasaki T, Lopes M B, Hankins G R, Helm G A (2002). Expression of survivin, an inhibitor of apoptosis protein, in tumors of the nervous system. Acta Neuropathol. 104, 105-109.

Sato F, Abraham J M, Yin J, Kan T, Ito T, Mori Y, Hamilton J P, Jin Z, Cheng Y, Paun B, Berki A T, Wang S, Shimada Y, Meltzer S J (2006). Polo-like kinase and survivin are esophageal tumor-specific promoters. Biochem. Biophys. Res. Commun. 342, 465-471.

Schmidt C, Bladt F, Goedecke S, Brinkmann V, Zschiesche W, Sharpe M, Gherardi E, Birchmeier C (1995). Scatter factor/hepatocyte growth factor is essential for liver development. Nature 373, 699-702.

Schmidt L, Duh F M, Chen F, Kishida T, Glenn G, Choyke P, Scherer S W, Zhuang Z, Lubensky I, Dean M, Allikmets R, Chidambaram A, Bergerheim U R, Feltis J T, Casadevall C, Zamarron A, Bernues M, Richard S, Lips C J, Walther M M, Tsui L C, Geil L, Orcutt M L, Stackhouse T, Lipan J, Slife L, Brauch H, Decker J, Niehans G, Hughson M D, Moch H, Storkel S, Lerman M I, Linehan W M, Zbar B (1997). Germline and somatic mutations in the tyrosine kinase domain of the MET proto-oncogene in papillary renal carcinomas. Nat. Genet. 16, 68-73.

Schmidt L, Junker K, Weirich G, Glenn G, Choyke P, Lubensky I, Zhuang Z, Jeffers M, Vande W G, Neumann H, Walther M, Linehan W M, Zbar B (1998). Two North American families with hereditary papillary renal carcinoma and identical novel mutations in the MET proto-oncogene. Cancer Res. 58, 1719-1722.

Sehgal A, Boynton A L, Young R F, Vermeulen S S, Yonemura K S, Kohler E P, Aldape H C, Simrell C R, Murphy G P (1998). Cell adhesion molecule Nr-CAM is over-expressed in human brain tumors. Int J Cancer 76, 451-458.

Sehgal A, Ricks S, Warrick J, Boynton A L, Murphy G P (1999). Antisense human neuroglia related cell adhesion molecule hNr-CAM, reduces the tumorigenic properties of human glioblastoma cells. Anticancer Res. 19, 4947-4953.

Seyfried T N (2001). Perspectives on brain tumor formation involving macrophages, glia, and neural stem cells. Perspect. Biol. Med. 44, 263-282.

Shimizu F, Watanabe T K, Shinomiya H, Nakamura Y, Fujiwara T (1997). Isolation and expression of a cDNA for human brain fatty acid-binding protein (B-FABP). Biochim. Biophys. Acta 1354, 24-28.

Sitnikova L, Mendese G, Liu Q, Woda B A, Lu D, Dresser K, Mohanty S, Rock K L, Jiang Z (2008). IMP3 predicts aggressive superficial urothelial carcinoma of the bladder. Clin Cancer Res. 14, 1701-1706.

Span P N, Sweep F C, Wiegerinck E T, Tjan-Heijnen V C, Manders P, Beex L V, de Kok J B (2004). Survivin is an independent prognostic marker for risk stratification of breast cancer patients. Clin Chem. 50, 1986-1993.

Stoeckli E T, Landmesser L T (1995). Axonin-1, Nr-CAM, and Ng-CAM play different roles in the in vivo guidance of chick commissural neurons. Neuron 14, 1165-1179.

Sun Y, Song M, Stevanovic S, Jankowiak C, Paschen A, Rammensee H G, Schadendorf D (2000). Identification of a new HLA-A(*)0201-restricted T-cell epitope from the tyrosinase-related protein 2 (TRP2) melanoma antigen. Int. J. Cancer 87, 399-404.

Takeuchi H, Bilchik A, Saha S, Turner R, Wiese D, Tanaka M, Kuo C, Wang H J, Hoon D S (2003). c-MET expression level in primary colon cancer: a predictor of tumor invasion and lymph node metastases. Clin Cancer Res. 9, 1480-1488.

Tan H Y, Liu J, Wu S M, Luo H S (2005). Expression of a novel apoptosis inhibitor-survivin in colorectal carcinoma. World J. Gastroenterol. 11, 4689-4692.

Trusolino L, Comoglio P M (2002). Scatter-factor and semaphorin receptors: cell signalling for invasive growth. Nat. Rev. Cancer 2, 289-300.

Tso C L, Freije W A, Day A, Chen Z, Merriman B, Perlina A, Lee Y, Dia E Q, Yoshimoto K, Mischel P S, Liau L M, Cloughesy T F, Nelson S F (2006). Distinct transcription profiles of primary and secondary glioblastoma subgroups. Cancer Res. 66, 159-167.

Tuck A B, Park M, Sterns E E, Boag A, Elliott B E (1996). Coexpression of hepatocyte growth factor and receptor (Met) in human breast carcinoma. Am. J. Pathol. 148, 225-232.

Uematsu M, Ohsawa I, Aokage T, Nishimaki K, Matsumoto K, Takahashi H, Asoh S, Teramoto A, Ohta S (2005). Prognostic significance of the immunohistochemical index of survivin in glioma: a comparative study with the MIB-1 index. J. Neurooncol. 72, 231-238.

van der Voort R, Taher T E, Keehnen R M, Smit L, Groenink M, Pals S T (1997). Paracrine regulation of germinal center B cell adhesion through the c-met-hepatocyte growth factor/scatter factor pathway. J. Exp. Med. 185, 2121-2131.

Veerkamp J H, Zimmerman A W (2001). Fatty acid-binding proteins of nervous tissue. J. Mol. Neurosci. 16, 133-142.

Viapiano M S, Bi W L, Piepmeier J, Hockfield S, Matthews R T (2005). Novel tumor-specific isoforms of BEHAB/brevican identified in human malignant gliomas. Cancer Res. 65, 6726-6733.

Viapiano M S, Hockfield S, Matthews R T (2008). BEHAB/brevican requires ADAMTS-mediated proteolytic cleavage to promote glioma invasion. J. Neurooncol.

Viapiano M S, Matthews R T (2006). From barriers to bridges: chondroitin sulfate proteoglycans in neuropathology. Trends Mol. Med. 12, 488-496.

Volkmer H, Leuschner R, Zacharias U, Rathjen F G (1996). Neurofascin induces neurites by heterophilic interactions with axonal NrCAM while NrCAM requires F11 on the axonal surface to extend neurites. J. Cell Biol. 135, 1059-1069.

Walter S, Herrgen L, Schoor O, Jung G, Wernet D, Buhring H J, Rammensee H G, Stevanovic S (2003). Cutting edge: predetermined avidity of human CD8 T cells expanded on calibrated MHC/anti-CD28-coated microspheres. J. Immunol. 171, 4974-4978.

Wang V, Davis D A, Hague M, Huang L E, Yarchoan R (2005). Differential gene up-regulation by hypoxia-inducible factor-1alpha and hypoxia-inducible factor-2alpha in HEK293T cells. Cancer Res. 65, 3299-3306.

Wiranowska M, Ladd S, Smith S R, Gottschall P E (2006). CD44 adhesion molecule and neuro-glial proteoglycan NG2 as invasive markers of glioma. Brain Cell Biol. 35, 159-172.

Wu C W, Kao H L, Li A F, Chi C W, Lin W C (2006). Protein tyrosine-phosphatase expression profiling in gastric cancer tissues. Cancer Lett. 242, 95-103.

Xie D, Zeng Y X, Wang H J, Wen J M, Tao Y, Sham J S, Guan X Y (2006). Expression of cytoplasmic and nuclear Survivin in primary and secondary human glioblastoma. Br. J. Cancer 94, 108-114.

Yamashita S, Masuda Y, Kurizaki T, Haga Y, Murayama T, Ikei S, Kamei M, Takeno S, Kawahara K (2007). Survivin expression predicts early recurrence in early-stage breast cancer. Anticancer Res. 27, 2803-2808.

Yang J, Price M A, Neudauer C L, Wilson C, Ferrone S, Xia H, Iida J, Simpson M A, McCarthy J B (2004). Melanoma chondroitin sulfate proteoglycan enhances FAK and ERK activation by distinct mechanisms. J. Cell Biol. 165, 881-891.

Yantiss R K, Cosar E, Fischer A H (2008). Use of IMP3 in identification of carcinoma in fine needle aspiration biopsies of pancreas. Acta Cytol. 52, 133-138.

Yantiss R K, Woda B A, Fanger G R, Kalos M, Whalen G F, Tada H, Andersen D K, Rock K L, Dresser K (2005). KOC (K homology domain containing protein overexpressed in cancer): a novel molecular marker that distinguishes between benign and malignant lesions of the pancreas. Am J Surg Pathol. 29, 188-195.

Zacharias U, Norenberg U, Rathjen F G (1999). Functional interactions of the immunoglobulin superfamily member F11 are differentially regulated by the extracellular matrix proteins tenascin-R and tenascin-C. J. Biol. Chem. 274, 24357-24365.

Zarnegar R, Michalopoulos G K (1995). The many faces of hepatocyte growth factor: from hepatopoiesis to hematopoiesis. J. Cell Biol. 129, 1177-1180.

Zeng Z, Weiser M R, D'Alessio M, Grace A, Shia J, Paty P B (2004). Immunoblot analysis of c-Met expression in human colorectal cancer: overexpression is associated with advanced stage cancer. Clin Exp. Metastasis 21, 409-417.

Zhang H, Kelly G, Zerillo C, Jaworski D M, Hockfield S (1998). Expression of a cleaved brain-specific extracellular matrix protein mediates glioma cell invasion In vivo. J. Neurosci. 18, 2370-2376.

Zhen H N, Zhang X, Hu P Z, Yang T T, Fei Z, Zhang J N, Fu L A, He X S, Ma F C, Wang X L (2005). Survivin expression and its relation with proliferation, apoptosis, and angiogenesis in brain gliomas. Cancer 104, 2775-2783.

Zheng W, Yi X, Fadare O, Liang S X, Martel M, Schwartz P E, Jiang Z (2008). The oncofetal protein IMP3: a novel biomarker for endometrial serous carcinoma. Am J Surg Pathol. 32, 304-315.

Ziu M, Schmidt N O, Cargioli T G, Aboody K S, Black P M, Carroll R S (2006). Glioma-produced extracellular matrix influences brain tumor tropism of human neural stem cells. J. Neurooncol. 79, 125-133.

We claim:

1. A pharmaceutical composition, comprising: (i) at least two immunogenic peptides from 8 to 100 amino acids in length, one of said peptides comprising an amino acid sequence that is at least 80% identical to SEQ ID NO: 7 and (ii) a pharmaceutically acceptable carrier.

2. The pharmaceutical composition according to claim 1, wherein another of said peptides comprises an amino acid sequence that is at least 80% identical to a sequence selected from the group consisting of SEQ ID NO: 9 to SEQ ID NO: 20.

3. The pharmaceutical composition according to claim 2, wherein the second peptide is selected from the group consisting of SEQ ID NO: 1 to SEQ ID NO: 20.

4. The pharmaceutical composition according to claim 1, wherein at least one of the at least two peptides includes non-peptide bonds.

5. The pharmaceutical composition of claim 1, where the first peptide comprises SEQ ID NO: 7.

6. The pharmaceutical composition of claim 1, wherein the first peptide consists of a core sequence consisting of SEQ ID NO: 7 with extensions of 1 to 10 amino acids on the C-terminal and/or the N-terminal of the core sequence.

7. The pharmaceutical composition of claim 1, wherein the first peptide consists of SEQ ID NO: 7.

8. The pharmaceutical composition according to claim 1, further comprising at least one suitable adjuvant.

9. The pharmaceutical composition according to claim 8, wherein the adjuvant is selected from the group consisting of colony-stimulating factors, GM-CSF, imiquimod, and resiquimod.

10. The pharmaceutical composition according to claim 8, comprising two to four adjuvants.

11. The pharmaceutical composition according to claim 10, wherein least two of the adjuvants are selected from the group consisting of CP-870,893, CpG7909, GM-CSF, imiquimod, and resiquimod.

12. The pharmaceutical composition according to claim 1, additionally comprising at least one antigen presenting cell.

13. The pharmaceutical composition according to claim 12, wherein the antigen presenting cell is a dendritic cell.

14. The pharmaceutical composition according to claim 12, wherein the at least one antigen presenting cell:
  a) is pulsed or loaded with the peptide; or
  b) comprises an expression construct encoding the peptide.

15. The pharmaceutical composition of claim 1, wherein the composition is administered intravenously, intra-arterially, intra-peritoneally, intramuscularly, intradermally, intra-tumorally, orally, dermally, nasally, buccally, rectally, vaginally, by inhalation, or by topical administration.

16. A method for treating and/or preventing a cancer in a patient, the method comprising administering to the patient a therapeutically effective amount of the pharmaceutical composition of claim 1.

17. The method according to claim 16, wherein the pharmaceutical composition is an anti-cancer vaccine.

18. The method of claim 17, wherein the cancer is one or more of cancer of the buccal cavity or pharynx, cancer of the digestive tract, cancer of the colon, rectum, or anus, cancer of the respiratory tract, breast cancer, cancer of the cervix uteri, vagina, or vulva, cancer of the uterine corpus or ovary, cancer of the male genital tract, cancer of the urinary tract, bone or soft tissue cancer, Kaposi sarcoma, melanoma of the skin, ocular melanoma, non-melanoma eye cancer, cancer of the brain and central nervous system, cancer of the thyroid and other endocrine glands, Hodgkin Lymphoma, Non-Hodgkin Lymphoma, myeloma, renal cancer, colorectal cancer, lung cancer, breast cancer, pancreatic cancer, prostate cancer, gastric cancer, GIST or glioblastoma.

19. The method according to claim 18, wherein the cancer is colorectal cancer.

20. The method according to claim 18, wherein the cancer is glioblastoma.

\* \* \* \* \*

SEQUENCE LISTING

```
<160> NUMBER OF SEQ ID NOS: 20

<210> SEQ ID NO 1
<211> LENGTH: 9
<212> TYPE: PRT
<213> ORGANISM: Homo sapiens

<400> SEQUENCE: 1

Thr Met Leu Ala Arg Leu Ala Ser Ala
1               5

<210> SEQ ID NO 2
<211> LENGTH: 9
```

```
<212> TYPE: PRT
<213> ORGANISM: Homo sapiens

<400> SEQUENCE: 2

Leu Thr Phe Gly Asp Val Val Ala Val
1               5

<210> SEQ ID NO 3
<211> LENGTH: 9
<212> TYPE: PRT
<213> ORGANISM: Homo sapiens

<400> SEQUENCE: 3

Asn Leu Asp Thr Leu Met Thr Tyr Val
1               5

<210> SEQ ID NO 4
<211> LENGTH: 9
<212> TYPE: PRT
<213> ORGANISM: Homo sapiens

<400> SEQUENCE: 4

Ala Met Thr Gln Leu Leu Ala Gly Val
1               5

<210> SEQ ID NO 5
<211> LENGTH: 9
<212> TYPE: PRT
<213> ORGANISM: Homo sapiens

<400> SEQUENCE: 5

Gly Leu Trp His His Gln Thr Glu Val
1               5

<210> SEQ ID NO 6
<211> LENGTH: 9
<212> TYPE: PRT
<213> ORGANISM: Homo sapiens

<400> SEQUENCE: 6

Lys Ile Gln Glu Ile Leu Thr Gln Val
1               5

<210> SEQ ID NO 7
<211> LENGTH: 9
<212> TYPE: PRT
<213> ORGANISM: Homo sapiens

<400> SEQUENCE: 7

Ala Leu Trp Ala Trp Pro Ser Glu Leu
1               5

<210> SEQ ID NO 8
<211> LENGTH: 17
<212> TYPE: PRT
<213> ORGANISM: Homo sapiens

<400> SEQUENCE: 8

Thr Phe Ser Tyr Val Asp Pro Val Ile Thr Ser Ile Ser Pro Lys Tyr
1               5                   10                  15

Gly

<210> SEQ ID NO 9
<211> LENGTH: 9
```

```
<212> TYPE: PRT
<213> ORGANISM: Homo sapiens

<400> SEQUENCE: 9

Ala Ile Ile Asp Gly Val Glu Ser Val
1               5

<210> SEQ ID NO 10
<211> LENGTH: 9
<212> TYPE: PRT
<213> ORGANISM: Homo sapiens

<400> SEQUENCE: 10

Lys Val Phe Ala Gly Ile Pro Thr Val
1               5

<210> SEQ ID NO 11
<211> LENGTH: 9
<212> TYPE: PRT
<213> ORGANISM: Homo sapiens

<400> SEQUENCE: 11

Ser Leu Trp Ala Gly Val Val Val Leu
1               5

<210> SEQ ID NO 12
<211> LENGTH: 15
<212> TYPE: PRT
<213> ORGANISM: Homo sapiens

<400> SEQUENCE: 12

Thr Leu Gly Glu Phe Leu Lys Leu Asp Arg Glu Arg Ala Lys Asn
1               5                   10                  15

<210> SEQ ID NO 13
<211> LENGTH: 10
<212> TYPE: PRT
<213> ORGANISM: Homo sapiens

<400> SEQUENCE: 13

Phe Leu Pro Ser Asp Phe Phe Pro Ser Val
1               5                   10

<210> SEQ ID NO 14
<211> LENGTH: 16
<212> TYPE: PRT
<213> ORGANISM: Homo sapiens

<400> SEQUENCE: 14

Asp Asp Pro Ser Thr Ile Glu Lys Leu Ala Lys Asn Lys Gln Lys Pro
1               5                   10                  15

<210> SEQ ID NO 15
<211> LENGTH: 17
<212> TYPE: PRT
<213> ORGANISM: Homo sapiens

<400> SEQUENCE: 15

Asn Lys Gln Lys Pro Ile Thr Pro Glu Thr Ala Glu Lys Leu Ala Arg
1               5                   10                  15

Asp

<210> SEQ ID NO 16
<211> LENGTH: 17
```

```
<212> TYPE: PRT
<213> ORGANISM: Homo sapiens

<400> SEQUENCE: 16

Asn Gly Ala Tyr Lys Ala Ile Pro Val Ala Gln Asp Leu Asn Ala Pro
1               5                   10                  15

Ser

<210> SEQ ID NO 17
<211> LENGTH: 15
<212> TYPE: PRT
<213> ORGANISM: Homo sapiens

<400> SEQUENCE: 17

Thr Leu Gly Glu Phe Leu Lys Leu Asp Arg Glu Arg Ala Lys Asp
1               5                   10                  15

<210> SEQ ID NO 18
<211> LENGTH: 9
<212> TYPE: PRT
<213> ORGANISM: Homo sapiens

<400> SEQUENCE: 18

Phe Thr Glu Leu Thr Leu Gly Glu Phe
1               5

<210> SEQ ID NO 19
<211> LENGTH: 9
<212> TYPE: PRT
<213> ORGANISM: Homo sapiens

<400> SEQUENCE: 19

Leu Met Leu Gly Glu Phe Leu Lys Leu
1               5

<210> SEQ ID NO 20
<211> LENGTH: 9
<212> TYPE: PRT
<213> ORGANISM: Homo sapiens

<400> SEQUENCE: 20

Glu Pro Asp Leu Ala Gln Cys Phe Tyr
1               5
```